United States Patent
Donohue et al.

(10) Patent No.: US 9,657,293 B2
(45) Date of Patent: May 23, 2017

(54) BIOLOGICAL CONTROL OF COLEOPTERAN PESTS

(71) Applicant: Syngenta Participations AG, Basel (CH)

(72) Inventors: Kevin Donohue, Research Triangle Park, NC (US); Renshui Liu, Research Triangle Park, NC (US); Jeng Shong Chen, Research Triangle Park, NC (US)

(73) Assignee: Sygenta Participations AG, Basel (CH)

( * ) Notice: Subject to any disclaimer, the term of this patent is extended or adjusted under 35 U.S.C. 154(b) by 0 days.

(21) Appl. No.: 14/410,441

(22) PCT Filed: Jun. 19, 2013

(86) PCT No.: PCT/US2013/046450
§ 371 (c)(1),
(2) Date: Dec. 22, 2014

(87) PCT Pub. No.: WO2013/192256
PCT Pub. Date: Dec. 27, 2013

(65) Prior Publication Data
US 2015/0337302 A1    Nov. 26, 2015

Related U.S. Application Data

(60) Provisional application No. 61/662,958, filed on Jun. 22, 2012.

(51) Int. Cl.
| | | |
|---|---|---|
| C12N 15/113 | (2010.01) | |
| A01N 57/16 | (2006.01) | |
| A01N 63/02 | (2006.01) | |
| C07K 14/435 | (2006.01) | |
| C12N 15/82 | (2006.01) | |

(52) U.S. Cl.
CPC ............ *C12N 15/113* (2013.01); *A01N 57/16* (2013.01); *A01N 63/02* (2013.01); *C07K 14/43563* (2013.01); *C12N 15/1135* (2013.01); *C12N 15/8218* (2013.01); *C12N 15/8286* (2013.01); *C12N 2310/14* (2013.01); *C12N 2310/141* (2013.01); *C12N 2310/3519* (2013.01); *C12N 2310/531* (2013.01)

(58) Field of Classification Search
CPC .......................... C12N 15/113; C12N 15/8286
See application file for complete search history.

(56) References Cited

U.S. PATENT DOCUMENTS

| | | | |
|---|---|---|---|
| 9,051,569 B2* | 6/2015 | Niimi | A01N 43/90 |
| 2006/0200878 A1* | 9/2006 | Lutfiyya | C12N 15/8216 800/285 |
| 2008/0313773 A1* | 12/2008 | Chua | C12N 15/113 800/278 |
| 2009/0307803 A1* | 12/2009 | Baum | A01N 63/02 800/298 |

FOREIGN PATENT DOCUMENTS

| | | |
|---|---|---|
| CN | 102212522 A | 10/2011 |
| WO | 2005/049841 A1 | 6/2005 |
| WO | 2005/110068 A2 | 11/2005 |
| WO | 2007/035650 A2 | 3/2007 |
| WO | 2007/095496 A2 | 8/2007 |

OTHER PUBLICATIONS

Notification of Transmittal of the International Search Report and the Written Opinion of the International Searching Authority, or the Declaration in corresponding International Application No. PCT/US2013/046450 mailed Nov. 19, 2013 (17 pp).

* cited by examiner

*Primary Examiner* — J. E. Angell
(74) *Attorney, Agent, or Firm* — Yoshimi D. Barron

(57) ABSTRACT

Disclosed are double stranded RNA molecules that are toxic to coleopteran insects. In particular, dsRNA molecules that capable of interfering with pest IAP genes and that are toxic to the target pest are provided. Further, methods of making and using the interfering RNA, for example in transgenic plants to confer protection from insect damage are disclosed.

17 Claims, 7 Drawing Sheets

Alignment: Global DNA alignment against reference molecule
Parameters: Scoring matrix: Linear (Mismatch 2, OpenGap 4, ExtGap 1)

Reference molecule: wcrIAP1, Region 1-1050
Number of sequences to align: 3

| Pos | Sequence | Start | End | Length | Matches | %Identity |
|---|---|---|---|---|---|---|
| Ref 1 | wcrIAP1 (SEQ ID NO:3) | 1 | 1050 | 1050 | | |
| 2 | ncrIAP1 (SEQ ID NO:17) | 1 | 1038 | 1038 | 1027 | 97 |
| 3 | scrIAP1 (SEQ ID NO:14) | 1 | 1036 | 1036 | 1005 | 95 |

```
wcrIAP1      1 ATGGCAGTAGTTCAATCAAATTACATTCAAAATATACCTTCTTTTGGATG
ncrIAP1      1 --------...-......................................
scrIAP1      1 .......GTAG..................---.......C...

wcrIAP1     51 TGTAGACCAACCTGACAACGGCTCCAAAACAACAAGAGAATCATTAGTAG
ncrIAP1     42 ..................................................
scrIAP1     48 ........................---........C.........

wcrIAP1    101 AAGTGTCTTCATCACGTCCACGCCAAGAAGACTACTCAGTATATGAGAAC
ncrIAP1     92 .......C..........................................
scrIAP1     95 ...........-----.....T..................G.........

wcrIAP1    151 AGACTGGCATCTTTCACTAACTGGCCCAACACCCAAGTGTCAAGAGAATC
ncrIAP1    142 ..................................................
scrIAP1    139 ..................................................

wcrIAP1    201 ATTAGCTCGAGCTGGTTTTATATATACAGGTCAAGATGACATCGTTATCT
ncrIAP1    192 ..................................................
scrIAP1    189 ........A.........................................

wcrIAP1    251 GCCCTATTTGTAAGATAGAGGGATACCGTTGGGTATCAGGAGACAATCCA
ncrIAP1    242 ..................................................
scrIAP1    239 .T................................................

wcrIAP1    301 ATGGATGATCATCGTGTTTGGAATCCCAACTGCCCCTTTCTTAATAGAAG
ncrIAP1    292 .............A....................................
scrIAP1    289 ........C...................G................
```

Figure 4A

```
wcrIAP1    351 AGATAACATCGAGCACGATCACTCTGTAGGTTCTAGAGACACTTGTGGAC
ncrIAP1    342 .........T........................................
scrIAP1    339 .........T...................T....................

wcrIAP1    401 TTTTTGGCATAGAATTGTTACCAAATTCAGTTCCTGAAGATAATACAAGT
ncrIAP1    392 ..................................................
scrIAP1    389 .....AA...........................................

wcrIAP1    451 AATTTACAAAAATTAGGGATCCAACCTGGAACAGGTCCACAAAATCAAGA
ncrIAP1    442 ...............................G..................
scrIAP1    439 ....................T..........G..................

wcrIAP1    501 CAAAATTACGTTAGAAAGCCGGTTAGCAACATTCCAGGGTTGGCCAAAGA
ncrIAP1    492 .........A........................................
scrIAP1    489 .........A.AT....................................A.

wcrIAP1    551 GCATTAAACAGAGGCCTTCTGAGTTAGCTGAGGCGGGATTTTATTACACA
ncrIAP1    542 ..............G...................................
scrIAP1    539 ..................C...............................

wcrIAP1    601 GGAGCTGGGGACCAAACTGTGTGCTTTTATTGTGGTGGGGGATTAAAAGA
ncrIAP1    592 ........A.........................................
scrIAP1    589 ........A.........................................

wcrIAP1    651 CTGGGATGAAGGAGATGATCCTTGGGAGCAACATGCCCTTTGGTTTAGCA
ncrIAP1    642 ..................................................
scrIAP1    639 ..................................................

wcrIAP1    701 AATGTGTGTTTCTCAATTTGAAAAAGGGCAAAGAATTCATCGATCAAGTA
ncrIAP1    692 .G................................................
scrIAP1    689 .G..C........T........................T..........

wcrIAP1    751 AAGAGGAAGGCTGATCCACAATTTTCAATTCCTGGACCTAGCGGTACTCA
ncrIAP1    742 ..................................................
scrIAP1    739 ..................................................

wcrIAP1    801 AGCCAAAGAGGAACCGACTGCTACTGAATCTTCAAGTGATAAACAAAGTG
ncrIAP1    792 ............................TG...................
scrIAP1    789 .............................---.................

wcrIAP1    851 AAACAGTGAAAACAAAATCAGATAGGGAAAGTTTCGCAACTGACACAACT
ncrIAP1    842 ..................................................
scrIAP1    836 ..................................................

wcrIAP1    901 TTGTGCAAAATTTGCTTTAAAAACGAACTTGGTGTTGTTTTCTTGCCTTG
ncrIAP1    892 ..................................................
scrIAP1    886 ..............A...................................
```

Figure 4B

```
wcrIAP1      951 TGGACATATTGTTGCTTGTGTAGATTGTGCTGCTGCACTAAAAACATGTG
ncrIAP1      942 ..................................................
scrIAP1      936 ..................................................

wcrIAP1     1001 CTGTATGCCGAAAACCTTTAGAGGCCACAGTCAGAGCGTT-CCTATCATA
ncrIAP1      992 ........................................T......---
scrIAP1      986 ........A...............................T.........

wcrIAP1     1050 A
ncrIAP1     1039 -
scrIAP1     1036 .
```

Figure 4C

SEQUENCE LISTING

```
<160> NUMBER OF SEQ ID NOS: 67

<210> SEQ ID NO 1
<211> LENGTH: 1622
<212> TYPE: DNA
<213> ORGANISM: Diabrotica virgifera

<400> SEQUENCE: 1
gagtatcgag tgagaaatcg tcgggtctga gttcgtgtgt ttagttcgtt ctgggtgtta      60
aaaattaagt aaaaatcggg taaaaatggg aaacttatta taaattcaac aagctgcaat     120
atcaatcaga tttcatggta ctaaaatggc agtagttcaa tcaaattaca ttcaaaatat     180
accttctttt ggatgtgtag accaacctga caacggctcc aaaacaacaa gagaatcatt     240
```

```
agtagaagtg tcttcatcac gtccacgcca agaagactac tcagtatatg agaacagact      300
ggcatctttc actaactggc ccaacaccca agtgtcaaga gaatcattag ctcgagctgg      360
ttttatatat acaggtcaag atgacatcgt tatctgccct atttgtaaga tagagggata      420
ccgttgggta tcaggagaca atccaatgga tgatcatcgt gtttggaatc ccaactgccc      480
ctttcttaat agaagagata acatcgagca cgatcactct gtaggttcta gagacacttg      540 tggactttt ggcatagaat tgttaccaaa ttcagttcct gaagataata caagtaattt       600
acaaaaatta gggatccaac ctggaacagg tccacaaaat caagacaaaa ttacgttaga      660
aagccggtta gcaacattcc agggttggcc aaagagcatt aaacagaggc cttctgagtt      720
agctgaggcg ggattttatt acacaggagc tggggaccaa actgtgtgct tttattgtgg      780
tgggggatta aaagactggg atgaaggaga tgatccttgg gagcaacatg ccctttggtt      840
tagcaaatgt gtgtttctca atttgaaaaa gggcaaagaa ttcatcgatc aagtaaagag      900
gaaggctgat ccacaatttt caattcctgg acctagcgt actcaagcca aagaggaacc       960
gactgctact gaatcttcaa gtgataaaca aagtgaaaca gtgaaaacaa atcagatag      1020 ggaaagtttc gcaactgaca caactttgtg caaaatttgc tttaaaaacg aacttggtgt     1080
tgttttcttg ccttgtggac atattgttgc ttgtgtagat tgtgctgctg cactaaaaac     1140
atgtgctgta tgccgaaaac ctttagaggc cacagtcaga gcgttcctat cataaatttt     1200
tattctgtta atagttttc acatttcatg tttcacacat acttagatct agtcaagatt      1260
gttagagttt tggcaaagaa attaaataaa aattctttc ataaaaatca tttctttaat      1320
attacattag agaaaaatta tatttttata ctgagtacaa atttgaacaa gttattaatt     1380
ttaagttaca aaatacgctt ttataggtta acaattatca aagcgcttaa atctaataga     1440
tactacacaa cattaaggac tgcaaaccat atctttcacg aagtaatccc tactagtgac     1500
caattgctcg ctaggagcag atgcaaatta cacaaattta ctataaatct gacattaaaa     1560
cttaggtgta tgtttgtgtg tatgttatgt attgatcata ataatatagt aatttataat     1620
at                                                                    1622
```

<210> SEQ ID NO 2
<211> LENGTH: 1050
<212> TYPE: DNA
<213> ORGANISM: Diabrotica virgifera

<400> SEQUENCE: 2

```
atggcagtag ttcaatcaaa ttacattcaa aatatacctt cttttggatg tgtagaccaa       60
cctgacaacg gctccaaaac aacaagagaa tcattagtag aagtgtcttc atcacgtcca      120
cgccaagaag actactcagt atatgagaac agactgcat ctttcactaa ctggcccaac       180
acccaagtgt caagagaatc attagctcga gctggtttta tatatacagg tcaagatgac      240
atcgttatct gccctatttg taagatagag ggataccgtt gggtatcagg agacaatcca      300
atggatgatc atcgtgtttg gaatcccaac tgccccttc ttaatagaag agataacatc       360
gagcacgatc actctgtagg ttctagagac acttgtggac tttttggcat agaattgtta      420
ccaaattcag ttcctgaaga taatacaagt aatttacaaa aattagggat ccaacctgga     480
acaggtccac aaaatcaaga caaaattacg ttagaaagcc ggttagcaac attccagggt     540
tggccaaaga gcattaaaca gaggccttct gagttagctg aggcgggatt ttattacaca     600
ggagctgggg accaaactgt gtgctttat tgtggtgggg gattaaaaga ctgggatgaa      660
```

```
ggagatgatc cttgggagca acatgcccett tggtttagca aatgtgtgtt tctcaatttg      720
aaaaagggca agaattcat cgatcaagta aagaggaagg ctgatccaca attttcaatt        780
cctggaccta gcggtactca agccaaagag gaaccgactg ctactgaatc ttcaagtgat       840
aaacaaagtg aaacagtgaa aacaaaatca gatgggaaaa gtttcgcaac tgacacaact      900
ttgtgcaaaa tttgctttaa aaacgaactt ggtgttgttt tcttgccttg tggacatatt      960
gttgcttgtg tagattgtgc tgctgcacta aaaacatgtg ctgtatgccg aaaacctta     1020 gaggccacag tcagagcgtt cctatcataa                                       1050

<210> SEQ ID NO 3
<211> LENGTH: 1622
<212> TYPE: RNA
<213> ORGANISM: Diabrotica virgifera

<400> SEQUENCE: 3
gaguaucgag ugagaaaucg ucgggucuga guucgugugu uuaguucguu cuggguguua       60
aaaauuaagu aaaaaucggg uaaaaauggg aaacuuauua uaaauucaac aagcugcaau     120
aucaaucaga uuucaugguga cuaaaauggc aguaguucaa ucaauuuaca uucaaaauau     180
accuucuuuu ggaugugag accaaccuga caacggcucc aaaacaacaa gagaaucauu       240
aguagaagug ucuucaucac guccacgcca agaagacuac ucaguauaug agaacagacu      300
ggcaucuuuc acuaacuggc ccaacaccca agugucaaga gaaucauuag cucgagcugg     360
uuuuauauau acaggucaag augcaucgu uaucugcccu auuuguaaga uagagggaua      420 ccguuggua ucaggagaca auccaaugga ugaucaucgu guuggaauc ccaacugccc       480 cuuucuuaau agaagagaua acaucgagca cgaucacucu uagguucua gagacacuug     540 uggacuuuuu ggcauagaau uguuaccaaa uucaguccu gaagauaaua caaguaauuu     600
acaaaaauua gggauccaac cuggaacagg uccacaaaau caagacaaaa uuacguuaga    660
aagccgguua gcaacauucc aggguuggcc aaagagcauu aaacagaggc cuucgaguu     720 agcugaggcg ggauuuuauu acacaggagc uggggaccaa acugugugcu uuuauugugg    780
ugggggauua aaagacuggg augaaggaga ugauccuugg gagcaacaug cccuuuggu     840 uagcaaaugu uguuucuca auuugaaaaa gggcaaagaa uucaucgauc aaguaaagag     900
gaaggcugau ccacaauuuu caauuccugg accagcggu acucaagcca aagaggaacc     960
gacugcuacu gaaucuucaa gugauaaaca aagugaaaca gugaaaacaa aaucagauag    1020
ggaaaguuuc gcaacugaca caacuuugug caaaauuugc uuuaaaaacg aacuggugu    1080 uguuuucuug ccuuguggac auauuguugc uuguguagau ugcugcugu cacuaaaaac    1140 augugcugua ugccgaaaac cuuuuagaggc cacagucaga gcguuccuau caauauuuu     1200 uauucuguua uaguuuuuc acauucaug uuucacacau acuuagaucu agucaagauu      1260
guuagaguuu uggcaaagaa auuaaauaaa aauucuuuuc auaaaaauca uuucuuuaau   1320
auuacauuag agaaaauua uauuuuuaua cugaguacaa auuugaacaa guauuaauu     1380 uuaaguuaca aaauacgcuu uuauagguua acaauuauca aagcgcuuaa aucuaauaga   1440 acuacacaa cauuaaggac ugcaaaccau ucuuuacg aaguaauccc uacuagugac      1500
caauugcucg cuaggagcag augcaaauua cacaaauuua cuauaaaucu gacauuaaaa   1560
cuuaggugua uguuugugug uauguuaugu auugaucaua auaauauagu aauuuauaau   1620
au                                                                    1622
```

<210> SEQ ID NO 4
<211> LENGTH: 1622
<212> TYPE: RNA
<213> ORGANISM: Diabrotica virgifera

<400> SEQUENCE: 4

| | | | | | |
|---|---|---|---|---|---|
| auauuauaaa | uuacuauauu | auuaugauca | auacauaaca | uacacacaaa | cauacaccua | 60 |
| aguuuuaaug | ucagauuuau | aguaaauuug | uguaauuugc | aucugucccu | agcgagcaau | 120 |
| uggucacuag | uagggauuac | uucgugaaag | auaugguuug | caguccuuaa | uguuguguag | 180 |
| uaucuauuag | auuuaagcgc | uuugauaauu | guuaaccuau | aaaagcguau | uuuguaacuu | 240 |
| aaaauuaaua | acuuguucaa | auuuguacuc | aguauaaaaa | uauaauuuuu | cucuaaugua | 300 |
| auauuaaaga | aaugauuuuu | augaaaagaa | uuuuauuua | auucuuugc | caaaacucua | 360 |
| acaaucuuga | cuagaucuaa | guaugugugu | aacugaaau | gugaaaaacu | auuaacagaa | 420 |
| uaaaauuua | ugauaggaac | gcucugacug | uggccucuaa | agguuuucgg | cauacagcac | 480 |
| auguuuuag | ugcagcagca | caaucuacac | aagcaacaau | augccacaa | ggcaagaaaa | 540 |
| caacaccaag | uucguuuuua | aagcaaauuu | ugcacaaagu | ugugucaguu | gcgaaacuuu | 600 |
| cccuaucuga | uuuuguuuuc | acuguuucac | uuuguuuauc | acuugaagau | ucaguagcag | 660 |
| ucgguuccuc | uuuggcuuga | guaccgcuag | guccaggaau | ugaaaauugu | ggaucagccu | 720 |
| uccucuuuac | uugaucgaug | aauucuuugc | ccuuuucaa | auugagaaac | acacauuugc | 780 |
| uaaaccaaag | ggcauguugc | ucccaaggau | caucuccuuc | aucccagucu | uuuaaucccc | 840 |
| caccacaaua | aaagcacaca | guuuggcccc | cagcuccugu | guaauaaaau | cccgccucag | 900 |
| cuaacucaga | aggccucugu | uuaaugcucu | uuggccaacc | cuggaauguu | gcuaaccggc | 960 |
| uuucuaacgu | aauuugucu | ugauuugug | gaccuguucc | agguuggauc | ccuaauuuuu | 1020 |
| guaaauuacu | uguauuaucu | ucaggaacug | aauuugguaa | caauucuaug | ccaaaaaguc | 1080 |
| cacaaguguc | ucuagaaccu | acagagugau | cgugcucgau | guuaucucuu | cuauuaagaa | 1140 |
| aggggcaguu | gggauuccaa | acacgaugau | cauccauugg | auugucuccu | gauacccaac | 1200 |
| gguaucccuc | uaucuacaa | auagggcaga | uaacgaugc | aucuugaccu | guauauauaa | 1260 |
| aaccagcucg | agcuaaugau | ucucuugaca | cuugggugu | gggccaguua | ugaaagaug | 1320 |
| ccagucuguu | cucauauacu | gaguagucuc | uuggcgugg | acgugaugaa | gacacuucua | 1380 |
| cuaaugauuc | ucuguugu | uggagccgu | ugucagguug | gucuacacau | ccaaaagaag | 1440 |
| guauauuuug | aauguaauuu | gauugaacua | cugccauuuu | aguaccauga | aaucugauug | 1500 |
| auauugcagc | uuguugaauu | uauaauaagu | ucccauuuu | uacccgauuu | uuacuuaauu | 1560 |
| uuuaacaccc | agaacgaacu | aaacacacga | acucagaccc | gacgauuucu | cacucgauac | 1620 |
| uc | | | | | | 1622 |

<210> SEQ ID NO 5
<211> LENGTH: 543
<212> TYPE: RNA
<213> ORGANISM: Diabrotica virgifera

<400> SEQUENCE: 5

| | | | | | |
|---|---|---|---|---|---|
| auggcaguag | uucaaucaaa | uuacauucaa | aauauaccuu | cuuuuggaug | uguagaccaa | 60 |
| ccugacaacg | gcuccaaaac | aacaagagaa | ucauuaguag | aagugucuuc | aucacgucca | 120 |
| cgccaagaag | acuacucagu | auaugagaac | agacuggcau | cuuucacuaa | cuggcccaac | 180 |
| acccaagugu | caagagaauc | auuagcucga | gcugguuuua | uauauacagg | ucaagaugac | 240 |

| | |
|---|---|
| aucguuaucu gcccuauuug uaagauagag ggauaccguu ggguaucagg agacaauccha | 300 |
| auggaugauc aucguguuug gaacccaac ugccccuuuc uuaauagaag agauaacauc | 360 |
| gagcacgauc acucuguagg uucuagagac acuuguggac uuuuuggcau agaauuguua | 420 |
| ccaaauucag uuccugaaga uaauacaagu aauuuacaaa aauuagggau ccaaccugga | 480 |
| acagguccac aaaaucaaga caaaauuacg uuagaaagcc gguuagcaac auuccagggu | 540 |
| ugg | 543 |

<210> SEQ ID NO 6
<211> LENGTH: 543
<212> TYPE: RNA
<213> ORGANISM: Diabrotica virgifera

<400> SEQUENCE: 6

| | |
|---|---|
| ccaacccugg aauguugcua accggcuuuc uaacguaauu uugucuugau uuuguggacc | 60 |
| uguuccaggu uggaucccua auuuuuguaa auuacuugua uuaucuucag gaacugaauu | 120 |
| ugguaacaau ucuaugccaa aaaguccaca agugucucua gaaccuacag agugaucgug | 180 |
| cucgauguua ucucuucuau uaagaaaggg gcaguuggga uuccaaacac gaugaucauc | 240 |
| cauuggauug ucuccugaua cccaacggua ucccucuauc uuacaaauag ggcagauaac | 300 |
| gaugucaucu ugaccuguau auauaaaacc agcucgagcu aaugauucuc uugacacuug | 360 |
| ggguuugggc caguuaguga aagaugccag ucguuucuca uauacugagu agucuucuug | 420 |
| gcguggacgu gaugaagaca cuucuacuaa ugauucucuu guuguuugg agccguuguc | 480 |
| agguuggucu acacauccaa aagaagguau auuuugaaug uaauugauu gaacuacugc | 540 |
| cau | 543 |

<210> SEQ ID NO 7
<211> LENGTH: 507
<212> TYPE: RNA
<213> ORGANISM: Diabrotica virgifera

<400> SEQUENCE: 7

| | |
|---|---|
| ccaaagagca uuaaacagag gccuucugag uuagcugagg cgggauuuua uuacacagga | 60 |
| gcuggggacc aaacuguguug cuuuuauugu gguggggau uaaaagacug ggaugaagga | 120 |
| gaugauccuu gggagcaaca ugcccuuugg uuuagcaaau guguguuucu caauuugaaa | 180 |
| aagggcaaag aauucaucga ucaaguaaag aggaaggcug auccacaauu uucaauuccu | 240 |
| ggaccuagcg uacucaagc caaagaggaa ccgacugcua cugaaucuuc aagugauaaa | 300 |
| caaagugaaa cagugaaaac aaaaucagau agggaaaguu ucgcaacuga cacaacuuug | 360 |
| ugcaaaauuu gcuuuaaaaa cgaacuuggu guuguuucu ugccuugggg acauauuguu | 420 |
| gcuuguguag auugugcugc ugcacuaaaa acaugugcug uagccgaaaa accuuuagag | 480 |
| gccacaguca gagcguuccu aucauaa | 507 |

<210> SEQ ID NO 8
<211> LENGTH: 507
<212> TYPE: RNA
<213> ORGANISM: Diabrotica virgifera

<400> SEQUENCE: 8

| | |
|---|---|
| uuaugauagg aacgcucuga cuguggccuc uaaagguuuu cggcauacag cacauguuuu | 60 |
| uagugcagca gcacaaucua cacaagcaac aauaugucca caaggcaaga aaacaacacc | 120 |
| aaguucguuu uuaaagcaaa uuuugcacaa aguugugca guugcgaaac uuucccuauc | 180 |

| | | |
|---|---|---|
| ugauuuuguu | uucacuguuu cacuuuguuu aucacuugaa gauucaguag cagucgguuc | 240 |
| cucuuuggcu | ugaguaccgc uagguccagg aauugaaaau ugugggaucag ccuuccucuu | 300 |
| uacuugaucg | augaauucuu ugcccuuuuu caaaugaga aacacacauu ugcuaaacca | 360 |
| aagggcaugu | ugcucccaag gaucaucucc uucaucccag ucuuuaauc ccccaccaca | 420 |
| auaaaagcac | acaguuuggu ccccagcucc uguguaauaa aauccccgccu cagcuaacuc | 480 |
| agaaggccuc | uguuuaaugc ucuuugg | 507 |

```
<210> SEQ ID NO 9
<211> LENGTH: 500
<212> TYPE: RNA
<213> ORGANISM: Diabrotica virgifera

<400> SEQUENCE: 9
```

| | | |
|---|---|---|
| aaccuggaac | agguccacaa aaucaagaca aaauuacguu agaaagccgg uuagcaacau | 60 |
| uccaggguug | gccaaagagc auuaaacaga ggccuucuga guuagcugag gcgggauuuu | 120 |
| auuacacagg | agcuggggac caaacugugu gcuuuuauug uggugggga uuaaaagacu | 180 |
| gggaugaagg | agaugauccu ugggagcaac augcccuuug guuuagcaaa ugugugutuc | 240 |
| ucaauuugaa | aaagggcaaa gaauucaucg aucaaguaaa gaggaaggcu gauccacaau | 300 |
| uuucaauucc | uggaccuagc gguacucaag ccaaagagga accgacugcu acugaaucuu | 360 |
| caagugauaa | acaagugaaa acagugaaaa caaaaucaga uagggaaagu uucgcaacug | 420 |
| acacaacuuu | gugcaaaaauu ugcuuuaaaa acgaacuugg uguuguuuuc uugccuugug | 480 |
| gacauauugu | ugcuugugua | 500 |

```
<210> SEQ ID NO 10
<211> LENGTH: 500
<212> TYPE: RNA
<213> ORGANISM: Artificial Sequence
<220> FEATURE:
<223> OTHER INFORMATION: wcrIAP1-C* antisense sequence.

<400> SEQUENCE: 10
```

| | | |
|---|---|---|
| uacacaagca | acaauauguc cacaaggcaa gaaaacaaca ccaaguucgu uuuuaaagca | 60 |
| aauuuugcac | aaaguugugu caguugcgaa acuuucccua ucugauuuug uuuucacugu | 120 |
| uucacuuugu | uuaucacuug aagauucagu agcagucggu uccucuuugg cuugaguacc | 180 |
| gcuaggucca | ggaauugaaa auguggauc agccuuccuc uuuacuugau cgaugaauuc | 240 |
| uuugcccuuu | uucaaauuga gaaacacaca uuugcuaaac caaagggcau guugcuccca | 300 |
| aggaucaucu | ccuucauccc agucuuuuaa uccccccacca caauaaaagc acacaguuug | 360 |
| gucccccagcu | ccuguguaau aaaauccccgc cucagcuaac ucagaaggcc ucuguuuaau | 420 |
| gcucuuuggc | caacccugga auguugcuaa ccggcuuucu aacguaauuu ugucuugauu | 480 |
| uuguggaccu | guuccagguu | 500 |

```
<210> SEQ ID NO 11
<211> LENGTH: 1462
<212> TYPE: DNA
<213> ORGANISM: Diabrotica virgifera virgifera

<400> SEQUENCE: 11
```

| | | |
|---|---|---|
| tcagaatgga | attatggcga tcaagtcatg actagacaca tagctttaaa ccgagattgt | 60 |
| cccttttgtac | tgaatccctc tacctcagga acgttcccta taacatcctc tcgtgtacct | 120 |

```
tccacttcga taaacatgta cagatcgtct gagactagac tggcctcttt tgaaaattgg      180
cctgctgctg atattgttac accagatagt ttggttcaag ctggctttta ctaccttaaa      240
gagggtgata atacacagcg tgccttctgt aaaggcgttg tgagagcttg ggaggttggt      300
gatgatccag atactgaaca ccagagacat tttcctaatt gcccatttgt tatggctgtt      360
attaatccta ggctccaagc aaggagaggt agtaatgata gaaataatcc ggaaaataat      420
caaatcgtta aggattcatt cccaaacatc aatgtagtcg gaaccgaaca aaacctggga      480
gagttgggag ttcaggctca caggggccca agaaatcga attttgctac cgtagaagcc      540
cgactacgtt cctatgttgg gtggtcctcg gatttgattc aaacacctga agtactcgct      600
gaggcaggct tctactatga aggaatgggc gaccaagtta gatgtttcca ttgtgatggg      660
gggctaagaa cgtgggatcc acacgacgac ccatggactg agcacgcgag atggtttccg      720
aattgttcct tcgtgaaatt ggtcaaagga caagatttcg ttacggcttg taccattgga      780
caaactacgg atagtagtgt gagaccttcc gctcaaagaa tacagacgac tcgaattcga      840
agagaagtta ccgaacgaga atccaaagt tacttgacta gtccacaggc gttggccgct       900
ctcagtatag gcctcaatgt cgaaagggta aaacgtgcaa taagagaaaa gttggagcag      960
accggaaggg cctattccca accagacgct ttagtggagg cagctcttaa tctgcaacat     1020
gaggaagagg atcccaattc gcatgagcat tacactccaa tagatcgtag tcttaggaat     1080
gttgtgtgtg cagcaatgga agagtgtatc gatcgcaaac ctgagcaggt gcagcaaccc     1140
gagcctgcac agcaaccaga aatggacgag gcgtttgaag tatcccccac cacagctcca     1200
gatggcactc cgcagttgca ttaccaactg gtaaaaacag tatcgctgga agaagaaat      1260 aggattctga agaagctag gctgtgcaag atttgtatgg acagcgaggt gggaatagtt      1320
ttcctaccgt gcggtcacct agcgacctgc gtcaactgcg cccctaattt agaagattgt     1380
cctgtttgta gatctactat taaagccact gtacgaacgt ttttctcata attattcgat     1440
ggtattaaaa taattgtttc ct                                              1462
```

<210> SEQ ID NO 12
<211> LENGTH: 1462
<212> TYPE: RNA
<213> ORGANISM: Diabrotica virgifera virgifera

<400> SEQUENCE: 12

```
ucagaaugga auuauggcga ucaagucaug acuagacaca uagcuuuaaa ccgagauugu       60
cccuuuguac ugaaucccuc uaccucagga acguuccua uaacauccuc ucguguaccu       120
uccacuucga uaaacaugua cagaucgucu gagacuagac uggccucuuu ugaaaauugg      180
ccugcugcug auauuguuac accagauagu uugguucaag cuggcuuuua cuaccuuaaa      240
gagggugaua auacacagcg ugccuucugu aaaggcguug ugagagcuug ggagguuggu      300
gaugauccag auacugaaca ccagagacau uuuccuaauu gcccauuugu uauggcuguu      360
auuaauccua ggcuccaagc aaggagaggu aguaaugaua gaaauaaucc ggaaaauaau      420
caaaucguua aggauucauu cccaaacauc aauguagucg gaaccgaaca aaaccuggga      480
gaguugggag uucaggcuca caggggccca agaaaucga auuuugcuac cguagaagcc       540
cgacuacguu ccuauguugg ugguccucg gauuugauuc aaacaccuga aguacucgcu       600
gaggcaggcu ucuacuauga aggaaugggc gaccaaguua gauguuucca uugugauggg      660
gggcuaagaa cgugggaucc acacgacgac ccauggacug agcacgcgag augguuuccg      720
aauuguuccu ucgugaaauu ggucaaagga caagauuucg uuacggcuug uaccauugga      780
```

```
caaacuacgg auaguagugu gagaccuucc gcucaaagaa uacagacgac ucgaauucga      840
agagaaguua ccgaacgaga aauccaaagu uacuugacua guccacaggc guuggccgcu      900
cucaguauag gccucaaugu cgaaagggua aaacgugcaa uaagagaaaa guuggagcag      960
accggaaggg ccuauuccca accagacgcu uuaguggagg cagcucuuaa ucugcaacau     1020
gaggaagagg aucccaauuc gcaugagcau uacacuccaa uagaucguag ucuuaggaau     1080
guugugugug cagcaaugga agagucuauc gaucgacaac cugagcaggu gcagcaaccc     1140
gagccugcac agcaaccaga aauggacgag gcguuugaag uaucccccac cacagcucca     1200
gauggcacuc cgcaguugca uuaccaacug guaaaaacag uaucgcugga agaagaaaau     1260
aggauucuga aagaagcuag gcugugcaag auuuguaugg acagcgaggu gggaauaguu     1320
uuccuaccgu gcggucaccu agcgaccugc gucaacugcg cccuaauuu agaagauugu     1380 ccuguuugua gaucuacuau uaaagccacu guacgaacgu uuucucaua auuauucgau     1440 gguauuaaaa uaauuguuuc cu                                             1462

<210> SEQ ID NO 13
<211> LENGTH: 1462
<212> TYPE: RNA
<213> ORGANISM: Artificial Sequence
<220> FEATURE:
<223> OTHER INFORMATION: wcrIAP2* antisense sequence.

<400> SEQUENCE: 13
aggaaacaau uauuuuaaua ccaucgaaua auuaugagaa aaacguucgu acaguggcuu       60
uaauaguaga ucuacaaaca ggacaaucuu cuaaauuagg ggcgcaguug acgcaggucg      120
cuaggugacc gcacgguagg aaaacuauuc ccaccucgcu guccauacaa aucuugcaca      180
gccuagcuuc uuucagaauc cuauuuucuu cuuccagcga uacuguuuuu accaguuggu      240
aaugcaacug cggagugcca ucuggagcug ugguggggga uacuucaaac gccucgucca      300
uuucugguug cugugcaggc ucgggugcu gcaccugcuc agguugucga ucgauacacu      360
cuuccauugc ugcacacaca acauuccuaa gacuacgauc uauuggagug uaaugcucau      420
gcgaauuggg auccucuucc ucauguugca gauuaagagc ugccuccacu aaagcgucug      480
guugggaaua ggcccuuccg gucugcucca acuuuucucu uauugcacgu uuuacccuuu      540
cgacauugag gccauacug agagcggcca acgccguggg acuagucaag uaacuuggga      600
uuucucguuc gguaacuucu cuucgaauuc gagucgucug uauucuuuga gcggaagguc      660
ucacacuacu auccguaguu uguccaaugg uacaagccgu aacgaaaucu uguccuuuga      720
ccaauuucac gaaggaacaa uucggaaacc aucucgcgug cucaguccau ggucgucgu      780 gugauccca cguucuuagc cccccaucac aauggaaaca ucuaacuugg ucgcccauuc      840
cuucauagua gaagccugcc ucagcgagua cuucaggugu uugaaucaaa uccgaggacc      900
acccaacaua ggaacuaguu cgggcuucua cgguagcaaa auucgauuuc uuugggcccc      960
ugugagccug aacucccaac ucucccaggu uuuguucggu uccgacuaca uugauguuug     1020
ggaaugaauc cuuaacgauu ugauuauuuu ccggauuauu ucuaucauua cuaccucucc     1080
uugcuuggag ccuaggauua auaacagcca uaacaauggg gcaauuagga aaugucucu     1140 gguguucagu aucuggauca ucaccaaccu cccaagcucu cacaacgccu uuacagaagg     1200
cacgcugugu auuaucaccc ucuuuaaggu aguaaaagcc agcuugaacc aaacuaucug     1260
guguaacaau aucagcagca ggccaauuuu caaaagaggc cagucuaguc ucagacgauc     1320
```

| | |
|---|---:|
| uguacauguu uaucgaagug aagguacac gagaggaugu auaggaacg uuccugagg | 1380 |
| uagagggauu caguacaaag ggacaaucuc gguuaaagc uauguguuca gucaugacuu | 1440 |
| gaucgccaua auuccauucu ga | 1462 |

<210> SEQ ID NO 14
<211> LENGTH: 1036
<212> TYPE: DNA
<213> ORGANISM: Diabrotica undecimpunctata

<400> SEQUENCE: 14

| | |
|---|---:|
| atggcaggta gtcaatcaaa ttacattcaa aatatatctt ttgcatgtgt agaccaacct | 60 |
| gacaacggct ccaaaacaag agaaccatta gtagaagtgt cttcaccacg tcaagaagac | 120 |
| tactcagtgt atgagaacag actggcatct ttcactaact ggcccaacac ccaagtgtca | 180 |
| agagaatcat tagctcaagc tggttttata tatacaggtc aagatgacat cgttatctgt | 240 |
| cctatttgta agatagaggg ataccgttgg gtatcaggag acaatccaat ggatgaccat | 300 |
| cgtgttttgga atcccaactg cccgtttctt aatagaagag ataacattga gcacgatcac | 360 |
| tctgtagttt ctagagacac ttgtggactt tttaacatag aattgttacc aaattcagtt | 420 |
| cctgaagata atacaagtaa tttacaaaaa ttagggattc aacctggaac gggtccacaa | 480 |
| aatcaagaca aaattacata tgaaagccgg ttagcaacat tccagggttg gccaaaaagc | 540 |
| attaaacaga ggccttccga gttagctgag gcgggatttt attacacagg agctggagac | 600 |
| caaactgtgt gcttttattg tggtgggggga ttaaaagact gggatgaagg agatgatcct | 660 |
| tgggagcaac atgccctttg gtttagcaag tgcgtgtttc ttaatttgaa aaagggcaaa | 720 |
| gaattcattg atcaagtaaa gaggaaggct gatccacaat tttcaattcc tggacctagc | 780 |
| ggtactcaag ccaaagagga accgactgct actgaatctt caagtgataa agtgaaaca | 840 |
| gtgaaaacaa aatcagatag ggaaagtttc gcaactgaca caactttgtg caaaatttgc | 900 |
| tataaaaacg aacttggtgt tgtttttcttg ccttgtggac atattgttgc ttgtgtagat | 960 |
| tgtgctgctg cactaaaaac atgtgctgta tgcagaaaac ctttagaggc cacagtcaga | 1020 |
| gcgtttccta tcataa | 1036 |

<210> SEQ ID NO 15
<211> LENGTH: 1036
<212> TYPE: RNA
<213> ORGANISM: Diabrotica undecimpunctata

<400> SEQUENCE: 15

| | |
|---|---:|
| auggcaggua gucaaucaaa uuacauucaa aauauaucuu uugcaugugu agaccaaccu | 60 |
| gacaacggcu ccaaaacaag agaaccauua guagaagugu cuucaccacg ucaagaagac | 120 |
| uacucagugu augagaacag acuggcaucu uucacuaacu ggcccaacac ccaagugcua | 180 |
| agagaaucau uagcucaagc ugguuuuaua uauacagguc aagaugacau cguuaucugu | 240 |
| ccuauuugua agauagaggg auaccguugg guaucaggag acaauccaau ggaugaccau | 300 |
| cguguuugga aucccaacug cccguuucuu aauagaagag auaacauuga gcacgaucac | 360 |
| ucuguaguuu cuagagacac uuguggacuu uuuaacauag aauuguuacc aaauucaguu | 420 |
| ccugaagaua auacaaguaa uuuacaaaaa uuagggauuc aaccuggaac ggguccacaa | 480 |
| aaucaagaca aaauuacaua ugaaagccgg uuagcaacau uccaggguug gccaaaaagc | 540 |
| auuaaacaga ggccuuccga guuagcugag gcgggauuuu auuacacagg agcuggagac | 600 |
| caaacuguau gcuuuuauug ugguggggga uuaaaagacu gggaugaagg agaugauccu | 660 |

```
ugggagcaac augcccuuug guuuagcaag ugcguguuuc uuaauuugaa aaagggcaaa      720
gaauucauug aucaaguaaa gaggaaggcu gauccacaau uuucaauucc uggaccuagc      780
gguacucaag ccaaagagga accgacugcu acugaaucuu caagugauaa agugaaaca      840 gugaaaacaa aaucagauag ggaaaguuuc gcaacugaca caacuuugug caaaauuugc      900
uauaaaaacg aacuuggugu guuuucuug ccuugggac auauuguugc uguguagau        960 ugcugcugcu cacuaaaaac augugcugua ugcagaaaac cuuuagaggc cacagucaga    1020
gcguuuccua ucauaa                                                   1036
```

<210> SEQ ID NO 16
<211> LENGTH: 1036
<212> TYPE: RNA
<213> ORGANISM: Artificial Sequence
<220> FEATURE:
<223> OTHER INFORMATION: scrIAP1* antisense sequence.

<400> SEQUENCE: 16

```
uuaugauagg aaacgcucug acuguggccu cuaaagguuu ucugcauaca gcacauguuu      60
uuagugcagc agcacaaucu acacaagcaa caauaugucc acaaggcaag aaaacaacac     120
caaguucguu uuauagcaa auuuugcaca aaguugaguc aguugcgaaa cuuucccuau     180
cugauuuugu uuucacuguu ucacuuuuau cacuugaaga uucaguagca gucgguuccu     240
cuuuggcuug aguaccgcua ggccaggaa uugaaaauug uggaucagcc uuccucuuua     300
cuugaucaau gaauucuuug cccuuuuuca aauuaagaaa cacgcacuug cuaaaccaaa    360
gggcauguug cucccaagga ucaucuccuu caucccaguc uuuuaauccc ccaccacaau    420
aaaagcacac aguuuggucu ccagcuccug uguaauaaaa ucccgcccuca gcuaacucgg    480 aaggccucug uuuaaugcuu uuuggccaac ccuggaaugu ugcuaaccgg cuuucauaug    540
uaauuuuguc uugauuuugu ggacccguuc cagguugaau cccuaauuuu uguaaauuac    600
uuguauuauc uucaggaacu gaauuuggua acaauucuau guuaaaaagu ccacaagugu    660
cucuagaaac uacagaguga ucgugcucaa uguauucucu ucuauuaaga aacgggcagu    720
ugggauucca aacacgaugg ucauccauug gauugucucc ugauacccaa cgguauccccu  780 cuaucuuuaca aauaggacag auaacgaugu caucuugacc uguauauaua aaaccagcuu    840
gagcuaauga uucucuugac acuugggugu ugggccaguu agugaaagau gccagucugu    900
ucucauacac ugaguagucu cuugacgug gugaagacac uucacuaau gguucucuug    960 uuuuggagcc guugucaggu ugggcuacac augcaaaaga uauauuuga auguaauuug    1020 auugacuacc ugccau                                                   1036
```

<210> SEQ ID NO 17
<211> LENGTH: 1038
<212> TYPE: DNA
<213> ORGANISM: Diabrotica barberi

<400> SEQUENCE: 17

```
agtcaatcaa attacattca aaatataacct tcttttggat gtgtagacca acctgacaac     60
ggctccaaaa caacaagaga atcattagta gaagtgtcct catcacgtcc acgccaagaa   120
gactactcag tatatgagaa cagactggca tctttcacta actggcccaa cacccaagtg   180
tcaagagaat cattagctcg agctggtttt atatatacag gtcaagatga catcgttatc   240
tgccctattt gtaagataga gggataccgt tgggtatcag gagacaatcc aatggatgat   300
```

```
catcgagttt ggaatcccaa ctgccccttt cttaatagaa gagataacat tgagcacgat    360
cactctgtag gttctagaga cacttgtgga cttttttggca tagaattgtt accaaattca    420
```

```
catcgagttt ggaatcccaa ctgccccttt cttaatagaa gagataacat tgagcacgat     360
cactctgtag gttctagaga cacttgtgga ctttttggca tagaattgtt accaaattca     420
gttcctgaag ataatacaag taatttacaa aaattaggga tccaacctgg aacgggtcca     480
caaaatcaag acaaaattac attagaaagc cggttagcaa cattccaggg ttggccaaag     540
agcattaaac agaggccgtc tgagttagct gaggcgggat tttattacac aggagctgga     600
gaccaaactg tgtgctttta ttgtggtggg ggattaaaag actgggatga aggagatgat     660
ccttgggagc aacatgccct ttggtttagc aagtgtgtgt ttctcaattt gaaaagggc      720 aaagaattca tcgatcaagt aaagaggaag gctgatccac aatttcaat tcctggacct     780 agcggtactc aagccaaaga ggaaccgact gctactgaat ctttgagtga taaacaaagt    840
gaaacagtga aaacaaaatc agatagggaa agtttcgcaa ctgacacaac tttgtgcaaa    900 atttgctttta aaacgaact tggtgttgtt ttcttgcctt gtggacatat tgttgcttgt     960
gtagattgtg ctgctgcact aaaaacatgt gctgtatgcc gaaaaccttt agaggccaca   1020
gtcagagcgt ttcctatc                                                 1038
```

<210> SEQ ID NO 18  
<211> LENGTH: 1038  
<212> TYPE: RNA  
<213> ORGANISM: Diabrotica barberi

<400> SEQUENCE: 18

```
agucaaucaa auuacauuca aaauauaccu ucuuuuggau guguagacca accugacaac    60
ggcuccaaaa caacaagaga aucauuagua gaaguguccu caucacgucc acgccaagaa   120
gacuacucag uauaugagaa cagacuggca ucuuucacua acuggcccaa cacccaagug   180
ucaagagaau cauugcucg agcugguuuu auauauacag gucaagauga caucguuauc   240
ugcccuauuu guaagauaga gggauaccgu uggguaucag gagacaaucc aauggaugau   300
caucgaguuu ggaaucccaa cugccccuuu cuuaauagaa gagauaacau ugagcacgau   360
cacucuguag guucuagaga cacuugugga cuuuuuggca uagaauuguu accaaauuca   420
guuccugaag auaauacaag uaauuuacaa aaauuaggga uccaaccugg aacgggucca   480
caaaaucaag acaaaauuac auuagaaagc cgguuagcaa cauuccaggg uuggccaaag   540
agcauuaaac agaggccguc ugaguuagcu gaggcgggau uuuauuacac aggagcugga   600
gaccaaacug ugugcuuuua uugugguggg ggauuaaaag acugggauga aggagaugau   660
ccuuggaagc aacaugcccu uugguuuagc aagugugugu uucucaauuu gaaaagggc    720 aaagaauuca ucgaucaagu aaagaggaag gcugauccac aauuuucaau uccuggaccu   780
agcgguacuc aagccaaaga ggaaccgacu gcuacugaau cuuugaguga uaaacaaagu   840
gaaacaguga aaacaaauc agauagggaa aguuucgcaa cugacacaac uuugugcaaa   900
auuugcuuua aaacgaacu uggguguguu uucuugccuu guggacauau uguugcuugu    960
guagauugug cugcugcacu aaaaacaugu gcuguaugcc gaaaaccuuu agaggccaca  1020
gucagagcgu uuccuauc                                                 1038
```

<210> SEQ ID NO 19  
<211> LENGTH: 1038  
<212> TYPE: RNA  
<213> ORGANISM: Artificial Sequence  
<220> FEATURE:  
<223> OTHER INFORMATION: ncrIAP1* antisense sequence.

<400> SEQUENCE: 19

```
gauaggaaac gcucugacug uggccucuaa agguuucgg cauacagcac auguuuuuag      60
ugcagcagca caaucuacac aagcaacaau augucacaa ggcaagaaaa caacaccaag     120
uucguuuuua aagcaaauuu ugcacaaagu ugucaguu gcgaaacuuu cccuaucuga     180 uuuuguuuc acuguucac uuuguuuauc acucaaagau cagagcag ucgguccuc        240 uuuggcuuga guaccgcuag guccaggaau ugaaauugu ggaucagccu uccucuuuac    300
uugaucgaug aauucuuugc ccuuuucaa auugagaaac acacacuugc uaaaccaag     360 ggcauguugc ucccaaggau caucccuuc aucccagucu uuaauccc caccacaaua      420 aaagcacaca guuggucuc cagcccugu guaauaaaau cccgccucag cuaaucaga      480 cggccucugu uuaaugcucu uuggccaacc cuggaauguu gcuaaccggc uuucuaaugu   540 aauuugucu ugauuugug dacccguucc agguuggauc ccuaauuuuu guaaauuacu    600
uguauuaucu ucaggaacug aauuugguaa caauucuaug ccaaaaaguc cacaagugc    660 ucuagaaccu acagagugau cgugcucaau guuaucucuu cuauuaagaa aggggcaguu   720
gggauuccaa acucgaugau caucauugg auugucuccu gaucccaac gguaucccuc    780 uaucuuacaa auagggcaga uaacgauguc aucuugaccu guauauauaa aaccagcucg  840
agcuaaugau ucucuugaca cuuggguguu gggccaguua ugaaagaug ccagucuguu   900 cucauauacu gaguagucuu cuuggcgugg acgugaugag dacacuucua cuaaugauuc  960 ucuuguugguu uuggagccgu ugucagguug gucuacacau ccaaaagaag guauauuuug 1020
aauguaauuu gauugacu                                                1038
```

<210> SEQ ID NO 20
<211> LENGTH: 349
<212> TYPE: PRT
<213> ORGANISM: Diabrotica virgifera
<400> SEQUENCE: 20

```
Met Ala Val Val Gln Ser Asn Tyr Ile Gln Asn Ile Pro Ser Phe Gly
1               5                   10                  15

Cys Val Asp Gln Pro Asp Asn Gly Ser Lys Thr Thr Arg Glu Ser Leu
            20                  25                  30

Val Glu Val Ser Ser Ser Arg Pro Arg Gln Glu Asp Tyr Ser Val Tyr
        35                  40                  45

Glu Asn Arg Leu Ala Ser Phe Thr Asn Trp Pro Asn Thr Gln Val Ser
    50                  55                  60

Arg Glu Ser Leu Ala Arg Ala Gly Phe Ile Tyr Thr Gly Gln Asp Asp
65                  70                  75                  80

Ile Val Ile Cys Pro Ile Cys Lys Ile Glu Gly Tyr Arg Trp Val Ser
                85                  90                  95

Gly Asp Asn Pro Met Asp Asp His Arg Val Trp Asn Pro Asn Cys Pro
            100                 105                 110

Phe Leu Asn Arg Arg Asp Asn Ile Glu His Asp His Ser Val Gly Ser
        115                 120                 125

Arg Asp Thr Cys Gly Leu Phe Gly Ile Glu Leu Leu Pro Asn Ser Val
    130                 135                 140

Pro Glu Asp Asn Thr Ser Asn Leu Gln Lys Leu Gly Ile Gln Pro Gly
145                 150                 155                 160

Thr Gly Pro Gln Asn Gln Asp Lys Ile Thr Leu Glu Ser Arg Leu Ala
                165                 170                 175

Thr Phe Gln Gly Trp Pro Lys Ser Ile Lys Gln Arg Pro Ser Glu Leu
```

```
                180             185             190
Ala Glu Ala Gly Phe Tyr Tyr Thr Gly Ala Gly Asp Gln Thr Val Cys
            195                 200                 205

Phe Tyr Cys Gly Gly Gly Leu Lys Asp Trp Asp Glu Gly Asp Asp Pro
        210                 215                 220

Trp Glu Gln His Ala Leu Trp Phe Ser Lys Cys Val Phe Leu Asn Leu
225                 230                 235                 240

Lys Lys Gly Lys Glu Phe Ile Asp Gln Val Lys Arg Lys Ala Asp Pro
                245                 250                 255

Gln Phe Ser Ile Pro Gly Pro Ser Gly Thr Gln Ala Lys Glu Glu Pro
            260                 265                 270

Thr Ala Thr Glu Ser Ser Asp Lys Gln Ser Glu Thr Val Lys Thr
        275                 280                 285

Lys Ser Asp Arg Glu Ser Phe Ala Thr Asp Thr Leu Cys Lys Ile
        290                 295                 300

Cys Phe Lys Asn Glu Leu Gly Val Val Phe Leu Pro Cys Gly His Ile
305                 310                 315                 320

Val Ala Cys Val Asp Cys Ala Ala Ala Leu Lys Thr Cys Ala Val Cys
                325                 330                 335

Arg Lys Pro Leu Glu Ala Thr Val Arg Ala Phe Leu Ser
                340                 345

<210> SEQ ID NO 21
<211> LENGTH: 476
<212> TYPE: PRT
<213> ORGANISM: Diabrotica virgifera

<400> SEQUENCE: 21

Ser Glu Trp Asn Tyr Gly Asp Gln Val Met Thr Arg His Ile Ala Leu
1               5                   10                  15

Asn Arg Asp Cys Pro Phe Val Leu Asn Pro Ser Thr Ser Gly Asn Val
            20                  25                  30

Pro Ile Thr Ser Ser Arg Val Pro Ser Thr Ser Ile Asn Met Tyr Arg
        35                  40                  45

Ser Ser Glu Thr Arg Leu Ala Ser Phe Glu Asn Trp Pro Ala Ala Asp
    50                  55                  60

Ile Val Thr Pro Asp Ser Leu Val Gln Ala Gly Phe Tyr Tyr Leu Lys
65                  70                  75                  80

Glu Gly Asp Asn Thr Gln Arg Ala Phe Cys Lys Gly Val Val Arg Ala
                85                  90                  95

Trp Glu Val Gly Asp Asp Pro Asp Thr Glu His Gln Arg His Phe Pro
            100                 105                 110

Asn Cys Pro Phe Val Met Ala Val Ile Asn Pro Arg Leu Gln Ala Arg
        115                 120                 125

Arg Gly Ser Asn Asp Arg Asn Asn Pro Glu Asn Asn Gln Ile Val Lys
    130                 135                 140

Asp Ser Phe Pro Asn Ile Asn Val Val Gly Thr Glu Gln Asn Leu Gly
145                 150                 155                 160

Glu Leu Gly Val Gln Ala His Arg Gly Pro Lys Lys Ser Asn Phe Ala
                165                 170                 175

Thr Val Glu Ala Arg Leu Arg Ser Tyr Val Gly Trp Ser Ser Asp Leu
            180                 185                 190

Ile Gln Thr Pro Glu Val Leu Ala Glu Ala Gly Phe Tyr Tyr Glu Gly
        195                 200                 205
```

Met Gly Asp Gln Val Arg Cys Phe His Cys Asp Gly Leu Arg Thr
210                 215                 220

Trp Asp Pro His Asp Asp Pro Trp Thr Glu His Ala Arg Trp Phe Pro
225                 230                 235                 240

Asn Cys Ser Phe Val Lys Leu Val Lys Gly Gln Asp Phe Val Thr Ala
            245                 250                 255

Cys Thr Ile Gly Gln Thr Thr Asp Ser Ser Val Arg Pro Ser Ala Gln
            260                 265                 270

Arg Ile Gln Thr Thr Arg Ile Arg Arg Glu Val Thr Glu Arg Glu Ile
            275                 280                 285

Gln Ser Tyr Leu Thr Ser Pro Gln Ala Leu Ala Ala Leu Ser Ile Gly
290                 295                 300

Leu Asn Val Glu Arg Val Lys Arg Ala Ile Arg Glu Lys Leu Glu Gln
305                 310                 315                 320

Thr Gly Arg Ala Tyr Ser Gln Pro Asp Ala Leu Val Glu Ala Ala Leu
                325                 330                 335

Asn Leu Gln His Glu Glu Glu Asp Pro Asn Ser His Glu His Tyr Thr
            340                 345                 350

Pro Ile Asp Arg Ser Leu Arg Asn Val Val Cys Ala Ala Met Glu Glu
            355                 360                 365

Cys Ile Asp Arg Gln Pro Glu Gln Val Gln Gln Pro Glu Pro Ala Gln
370                 375                 380

Gln Pro Glu Met Asp Glu Ala Phe Glu Val Ser Pro Thr Thr Ala Pro
385                 390                 395                 400

Asp Gly Thr Pro Gln Leu His Tyr Gln Leu Val Lys Thr Val Ser Leu
                405                 410                 415

Glu Glu Glu Asn Arg Ile Leu Lys Glu Ala Arg Leu Cys Lys Ile Cys
            420                 425                 430

Met Asp Ser Glu Val Gly Ile Val Phe Leu Pro Cys Gly His Leu Ala
            435                 440                 445

Thr Cys Val Asn Cys Ala Pro Asn Leu Glu Asp Cys Pro Val Cys Arg
            450                 455                 460

Ser Thr Ile Lys Ala Thr Val Arg Thr Phe Phe Ser
465                 470                 475

<210> SEQ ID NO 22
<211> LENGTH: 344
<212> TYPE: PRT
<213> ORGANISM: Diabrotica undecimpunctata

<400> SEQUENCE: 22

Met Ala Gly Ser Gln Ser Asn Tyr Ile Gln Asn Ile Ser Phe Ala Cys
1               5                   10                  15

Val Asp Gln Pro Asp Asn Gly Ser Lys Thr Arg Glu Pro Leu Val Glu
            20                  25                  30

Val Ser Ser Pro Arg Gln Glu Asp Tyr Ser Val Tyr Glu Asn Arg Leu
        35                  40                  45

Ala Ser Phe Thr Asn Trp Pro Asn Thr Gln Val Ser Arg Glu Ser Leu
    50                  55                  60

Ala Gln Ala Gly Phe Ile Tyr Thr Gly Gln Asp Ile Val Ile Cys
65                  70                  75                  80

Pro Ile Cys Lys Ile Glu Gly Tyr Arg Trp Val Ser Gly Asp Asn Pro
                85                  90                  95

Met Asp Asp His Arg Val Trp Asn Pro Asn Cys Pro Phe Leu Asn Arg
            100                 105                 110

```
Arg Asp Asn Ile Glu His Asp His Ser Val Ser Arg Asp Thr Cys
            115                 120                 125

Gly Leu Phe Asn Ile Glu Leu Leu Pro Asn Ser Val Pro Glu Asp Asn
130                 135                 140

Thr Ser Asn Leu Gln Lys Leu Gly Ile Gln Pro Gly Thr Gly Pro Gln
145                 150                 155                 160

Asn Gln Asp Lys Ile Thr Tyr Glu Ser Arg Leu Ala Thr Phe Gln Gly
                165                 170                 175

Trp Pro Lys Ser Ile Lys Gln Arg Pro Ser Glu Leu Ala Glu Ala Gly
                180                 185                 190

Phe Tyr Tyr Thr Gly Ala Gly Asp Gln Thr Val Cys Phe Tyr Cys Gly
                195                 200                 205

Gly Gly Leu Lys Asp Trp Asp Glu Gly Asp Pro Trp Glu Gln His
            210                 215                 220

Ala Leu Trp Phe Ser Lys Cys Val Phe Leu Asn Leu Lys Lys Gly Lys
225                 230                 235                 240

Glu Phe Ile Asp Gln Val Lys Arg Lys Ala Asp Pro Gln Phe Ser Ile
                245                 250                 255

Pro Gly Pro Ser Gly Thr Gln Ala Lys Glu Glu Pro Thr Ala Thr Glu
                260                 265                 270

Ser Ser Ser Asp Lys Ser Glu Thr Val Lys Thr Lys Ser Asp Arg Glu
            275                 280                 285

Ser Phe Ala Thr Asp Thr Thr Leu Cys Lys Ile Cys Tyr Lys Asn Glu
            290                 295                 300

Leu Gly Val Val Phe Leu Pro Cys Gly His Ile Val Ala Cys Val Asp
305                 310                 315                 320

Cys Ala Ala Ala Leu Lys Thr Cys Ala Val Cys Arg Lys Pro Leu Glu
                325                 330                 335

Ala Thr Val Arg Ala Phe Pro Ile
            340

<210> SEQ ID NO 23
<211> LENGTH: 346
<212> TYPE: PRT
<213> ORGANISM: Diabrotica barberi

<400> SEQUENCE: 23

Ser Gln Ser Asn Tyr Ile Gln Asn Ile Pro Ser Phe Gly Cys Val Asp
1               5                   10                  15

Gln Pro Asp Asn Gly Ser Lys Thr Thr Arg Glu Ser Leu Val Glu Val
                20                  25                  30

Ser Ser Ser Arg Pro Arg Gln Glu Asp Tyr Ser Val Tyr Glu Asn Arg
            35                  40                  45

Leu Ala Ser Phe Thr Asn Trp Pro Asn Thr Gln Val Ser Arg Glu Ser
50                  55                  60

Leu Ala Arg Ala Gly Phe Ile Tyr Thr Gly Gln Asp Ile Val Ile
65                  70                  75                  80

Cys Pro Ile Cys Lys Ile Glu Gly Tyr Arg Trp Val Ser Gly Asp Asn
                85                  90                  95

Pro Met Asp Asp His Arg Val Trp Asn Pro Asn Cys Pro Phe Leu Asn
                100                 105                 110

Arg Arg Asp Asn Ile Glu His Asp His Ser Val Gly Ser Arg Asp Thr
            115                 120                 125

Cys Gly Leu Phe Gly Ile Glu Leu Leu Pro Asn Ser Val Pro Glu Asp
```

```
            130                 135                 140
Asn Thr Ser Asn Leu Gln Lys Leu Gly Ile Gln Pro Gly Thr Gly Pro
145                 150                 155                 160

Gln Asn Gln Asp Lys Ile Thr Leu Glu Ser Arg Leu Ala Thr Phe Gln
                165                 170                 175

Gly Trp Pro Lys Ser Ile Lys Gln Arg Pro Ser Glu Leu Ala Glu Ala
            180                 185                 190

Gly Phe Tyr Tyr Thr Gly Ala Gly Asp Gln Thr Val Cys Phe Tyr Cys
                195                 200                 205

Gly Gly Gly Leu Lys Asp Trp Asp Glu Gly Asp Asp Pro Trp Glu Gln
            210                 215                 220

His Ala Leu Trp Phe Ser Lys Cys Val Phe Leu Asn Leu Lys Lys Gly
225                 230                 235                 240

Lys Glu Phe Ile Asp Gln Val Lys Arg Lys Ala Asp Pro Gln Phe Ser
                245                 250                 255

Ile Pro Gly Pro Ser Gly Thr Gln Ala Lys Glu Glu Pro Thr Ala Thr
            260                 265                 270

Glu Ser Leu Ser Asp Lys Gln Ser Glu Thr Val Lys Thr Lys Ser Asp
            275                 280                 285

Arg Glu Ser Phe Ala Thr Asp Thr Thr Leu Cys Lys Ile Cys Phe Lys
            290                 295                 300

Asn Glu Leu Gly Val Val Phe Leu Pro Cys Gly His Ile Val Ala Cys
305                 310                 315                 320

Val Asp Cys Ala Ala Ala Leu Lys Thr Cys Ala Val Cys Arg Lys Pro
                325                 330                 335

Leu Glu Ala Thr Val Arg Ala Phe Pro Ile
                340                 345

<210> SEQ ID NO 24
<211> LENGTH: 438
<212> TYPE: PRT
<213> ORGANISM: Drosophila melanogaster

<400> SEQUENCE: 24

Met Ala Ser Val Val Ala Asp Leu Pro Ser Tyr Gly Pro Ile Ala Phe
1               5                   10                  15

Asp Gln Val Asp Asn Asn Thr Asn Ala Thr Gln Leu Phe Lys Asn Asn
                20                  25                  30

Ile Asn Lys Thr Arg Met Asn Asp Leu Asn Arg Glu Glu Thr Arg Leu
            35                  40                  45

Lys Thr Phe Thr Asp Trp Pro Leu Asp Trp Leu Asp Lys Arg Gln Leu
50                  55                  60

Ala Gln Thr Gly Met Tyr Phe Thr His Ala Gly Asp Lys Val Lys Cys
65                  70                  75                  80

Phe Phe Cys Gly Val Glu Ile Gly Cys Trp Glu Gln Glu Asp Gln Pro
                85                  90                  95

Val Pro Glu His Gln Arg Trp Ser Pro Asn Cys Pro Leu Leu Arg Arg
            100                 105                 110

Arg Thr Thr Asn Asn Val Pro Ile Asn Ala Glu Ala Leu Asp Arg Ile
            115                 120                 125

Leu Pro Pro Ile Ser Tyr Asp Ile Cys Gly Ala Asn Asp Ser Thr Leu
            130                 135                 140

Glu Met Arg Glu His Ala Tyr Ala Glu Gly Val Ile Pro Met Ser Gln
145                 150                 155                 160
```

-continued

```
Leu Ile Gln Ser Ile Gly Met Asn Ala Val Asn Ala Ala Gly Ser Val
                165                 170                 175
Thr Gly Thr Ala Ala Pro Gln Pro Arg Val Thr Val Ala Thr His Ala
            180                 185                 190
Ser Thr Ala Thr Gln Ala Thr Gly Asp Val Gln Pro Glu Thr Cys Arg
        195                 200                 205
Pro Ser Ala Ala Ser Gly Asn Tyr Phe Pro Gln Tyr Pro Glu Tyr Ala
    210                 215                 220
Ile Glu Thr Ala Arg Leu Arg Thr Phe Glu Ala Trp Pro Arg Asn Leu
225                 230                 235                 240
Lys Gln Lys Pro His Gln Leu Ala Glu Ala Gly Phe Phe Tyr Thr Gly
                245                 250                 255
Val Gly Asp Arg Val Arg Cys Phe Ser Cys Gly Gly Gly Leu Met Asp
            260                 265                 270
Trp Asn Asp Asn Asp Glu Pro Trp Glu Gln His Ala Leu Trp Leu Ser
        275                 280                 285
Gln Cys Arg Phe Val Lys Leu Met Lys Gly Gln Leu Tyr Ile Asp Thr
    290                 295                 300
Val Ala Ala Lys Pro Val Leu Ala Glu Glu Lys Glu Glu Ser Ser Ser
305                 310                 315                 320
Ile Gly Gly Val Ala Val Ala Ser Thr Gln Ala Ser Glu Glu Glu Gln
                325                 330                 335
Gln Thr Ser Leu Ser Ser Glu Glu Ala Val Ser Gly Asp Val Ala Pro
            340                 345                 350
Ser Val Ala Pro Thr Ala Ala Thr Arg Ile Phe Asn Lys Ile Val Glu
        355                 360                 365
Ala Thr Ala Val Ala Thr Pro Ser Thr Asn Ser Ser Gly Ser Thr Ser
    370                 375                 380
Ile Pro Glu Glu Lys Leu Cys Lys Ile Cys Tyr Gly Ala Glu Tyr Asn
385                 390                 395                 400
Thr Ala Phe Leu Pro Cys Gly His Val Val Ala Cys Ala Lys Cys Ala
                405                 410                 415
Ser Ser Val Thr Lys Cys Pro Leu Cys Arg Lys Pro Phe Thr Asp Val
            420                 425                 430
Met Arg Val Tyr Phe Ser
        435

<210> SEQ ID NO 25
<211> LENGTH: 19
<212> TYPE: RNA
<213> ORGANISM: Diabrotica virgifera

<400> SEQUENCE: 25
gaguaucgag ugagaaauc                                                 19

<210> SEQ ID NO 26
<211> LENGTH: 19
<212> TYPE: RNA
<213> ORGANISM: Diabrotica virgifera

<400> SEQUENCE: 26
aguaucgagu gagaaaucg                                                 19

<210> SEQ ID NO 27
<211> LENGTH: 19
<212> TYPE: RNA
<213> ORGANISM: Diabrotica virgifera
```

<400> SEQUENCE: 27
guaucgagug agaaaucgu                                                    19

<210> SEQ ID NO 28
<211> LENGTH: 19
<212> TYPE: RNA
<213> ORGANISM: Diabrotica virgifera

<400> SEQUENCE: 28
auauaguaau uuauaauau                                                    19

<210> SEQ ID NO 29
<211> LENGTH: 19
<212> TYPE: RNA
<213> ORGANISM: Diabrotica virgifera

<400> SEQUENCE: 29
ucagaaugga auuauggcg                                                    19

<210> SEQ ID NO 30
<211> LENGTH: 19
<212> TYPE: RNA
<213> ORGANISM: Diabrotica virgifera

<400> SEQUENCE: 30
cagaauggaa uuauggcga                                                    19

<210> SEQ ID NO 31
<211> LENGTH: 19
<212> TYPE: RNA
<213> ORGANISM: Diabrotica virgifera

<400> SEQUENCE: 31
agaauggaau uauggcgau                                                    19

<210> SEQ ID NO 32
<211> LENGTH: 19
<212> TYPE: RNA
<213> ORGANISM: Diabrotica virgifera

<400> SEQUENCE: 32
auuaaaauaa uuguuuccu                                                    19

<210> SEQ ID NO 33
<211> LENGTH: 19
<212> TYPE: RNA
<213> ORGANISM: Diabrotica virgifera

<400> SEQUENCE: 33
auggcaggua gucaaucaa                                                    19

<210> SEQ ID NO 34
<211> LENGTH: 19
<212> TYPE: RNA
<213> ORGANISM: Diabrotica virgifera

<400> SEQUENCE: 34
uggcagguag ucaaucaaa                                                    19

<210> SEQ ID NO 35
<211> LENGTH: 19
<212> TYPE: RNA

```
<213> ORGANISM: Diabrotica virgifera

<400> SEQUENCE: 35
ggcagguagu cgauuucuca cucgauacu                                            19

<210> SEQ ID NO 43
<211> LENGTH: 19
<212> TYPE: RNA
<213> ORGANISM: Artificial Sequence
<220> FEATURE:
<223> OTHER INFORMATION: Third 19-mer antisense sequence of SEQ ID NO:4.

<400> SEQUENCE: 43
acgauuucuc acucgauac                                            19

<210> SEQ ID NO 44
<211> LENGTH: 19
<212> TYPE: RNA
<213> ORGANISM: Artificial Sequence
<220> FEATURE:
<223> OTHER INFORMATION: Last 19-mer antisense sequence of SEQ ID NO:4.

<400> SEQUENCE: 44
auauuauaaa uuacuauau                                            19

<210> SEQ ID NO 45
<211> LENGTH: 19
<212> TYPE: RNA
<213> ORGANISM: Artificial Sequence
<220> FEATURE:
<223> OTHER INFORMATION: First 19-mer antisense sequence of SEQ ID
      NO:13.

<400> SEQUENCE: 45
cgccauaauu ccauucuga                                            19

<210> SEQ ID NO 46
<211> LENGTH: 19
<212> TYPE: RNA
<213> ORGANISM: Artificial Sequence
<220> FEATURE:
<223> OTHER INFORMATION: Second 19-mer antisense sequence of SEQ ID
      NO:13.

<400> SEQUENCE: 46
ucgccauaau uccauucug                                            19

<210> SEQ ID NO 47
<211> LENGTH: 19
<212> TYPE: RNA
<213> ORGANISM: Artificial Sequence
<220> FEATURE:
<223> OTHER INFORMATION: Third 19-mer antisense sequence of SEQ ID
      NO:13.

<400> SEQUENCE: 47
aucgccauaa uuccauucu                                            19

<210> SEQ ID NO 48
<211> LENGTH: 19
<212> TYPE: RNA
<213> ORGANISM: Artificial Sequence
<220> FEATURE:
<223> OTHER INFORMATION: Last 19-mer antisense sequence of SEQ ID NO:13.

<400> SEQUENCE: 48
aggaaacaau uauuuaau                                             19

<210> SEQ ID NO 49

```
<211> LENGTH: 19
<212> TYPE: RNA
<213> ORGANISM: Artificial Sequence
<220> FEATURE:
<223> OTHER INFORMATION: First 19-mer antisense sequence of SEQ ID
      NO:16.

<400> SEQUENCE: 49
uugauugacu accugccau                                                   19

<210> SEQ ID NO 50
<211> LENGTH: 19
<212> TYPE: RNA
<213> ORGANISM: Artificial Sequence
<220> FEATURE:
<223> OTHER INFORMATION: Second 19-mer antisense sequence of SEQ ID
      NO:16.

<400> SEQUENCE: 50
uuugauugac uaccugcca                                                   19

<210> SEQ ID NO 51
<211> LENGTH: 19
<212> TYPE: RNA
<213> ORGANISM: Artificial Sequence
<220> FEATURE:
<223> OTHER INFORMATION: Third 19-mer antisense sequence of SEQ ID
      NO:16.

<400> SEQUENCE: 51
auuugauuga cuaccugcc                                                   19

<210> SEQ ID NO 52
<211> LENGTH: 19
<212> TYPE: RNA
<213> ORGANISM: Artificial Sequence
<220> FEATURE:
<223> OTHER INFORMATION: Last 19-mer antisense sequence of SEQ ID NO:16.

<400> SEQUENCE: 52
ugauaggaaa cgcucugac                                                   19

<210> SEQ ID NO 53
<211> LENGTH: 19
<212> TYPE: RNA
<213> ORGANISM: Artificial Sequence
<220> FEATURE:
<223> OTHER INFORMATION: First 19-mer antisense sequence of SEQ ID
      NO:19.

<400> SEQUENCE: 53
gaauguaauu ugauugacu                                                   19

<210> SEQ ID NO 54
<211> LENGTH: 19
<212> TYPE: RNA
<213> ORGANISM: Artificial Sequence
<220> FEATURE:
<223> OTHER INFORMATION: Second 19-mer antisense sequence of SEQ ID
      NO:19.

<400> SEQUENCE: 54
ugaauguaau uugauugac                                                   19

<210> SEQ ID NO 55
<211> LENGTH: 19
<212> TYPE: RNA
```

```
<213> ORGANISM: Artificial Sequence
<220> FEATURE:
<223> OTHER INFORMATION: Third 19-mer antisense sequence of SEQ ID
      NO:19.

<400> SEQUENCE: 55
uugaauguaa uuugauuga                                                    19

<210> SEQ ID NO 56
<211> LENGTH: 19
<212> TYPE: RNA
<213> ORGANISM: Artificial Sequence
<220> FEATURE:
<223> OTHER INFORMATION: Last 19-mer antisense sequence of SEQ ID NO:19.

<400> SEQUENCE: 56
gauaggaaac gcucugacu                                                    19

<210> SEQ ID NO 57
<211> LENGTH: 22
<212> TYPE: DNA
<213> ORGANISM: Artificial Sequence
<220> FEATURE:
<223> OTHER INFORMATION: Forward primer sequence.

<400> SEQUENCE: 57
agagcattaa acagaggcct tc                                                22

<210> SEQ ID NO 58
<211> LENGTH: 22
<212> TYPE: DNA
<213> ORGANISM: Artificial Sequence
<220> FEATURE:
<223> OTHER INFORMATION: Reverse primer sequence.

<400> SEQUENCE: 58
tgataggaac gctctgactg tg                                                22

<210> SEQ ID NO 59
<211> LENGTH: 27
<212> TYPE: DNA
<213> ORGANISM: Artificial Sequence
<220> FEATURE:
<223> OTHER INFORMATION: Forward primer sequence.

<400> SEQUENCE: 59
atggcagtag ttcaatcaaa ttacatt                                           27

<210> SEQ ID NO 60
<211> LENGTH: 19
<212> TYPE: DNA
<213> ORGANISM: Artificial Sequence
<220> FEATURE:
<223> OTHER INFORMATION: Reverse primer sequence

<400> SEQUENCE: 60
gccaaccctg gaatgttgc                                                    19

<210> SEQ ID NO 61
<211> LENGTH: 20
<212> TYPE: DNA
<213> ORGANISM: Artificial Sequence
<220> FEATURE:
<223> OTHER INFORMATION: Forward primer sequence

<400> SEQUENCE: 61
```
ttgtggtggg ggattaaaag               20

<210> SEQ ID NO 62
<211> LENGTH: 20
<212> TYPE: DNA
<213> ORGANISM: Artificial Sequence
<220> FEATURE:
<223> OTHER INFORMATION: Reverse primer sequence.

<400> SEQUENCE: 62
catttgctaa accaaagggc               20

<210> SEQ ID NO 63
<211> LENGTH: 1426
<212> TYPE: DNA
<213> ORGANISM: Artificial Sequence
<220> FEATURE:
<223> OTHER INFORMATION: hpwcrIAP1C/wcrIAP1C*

<400> SEQUENCE: 63
aacctggaac aggtccacaa aatcaagaca aaattacgtt agaaagccgg ttagcaacat     60
tccagggttg gccaaagagc attaaacaga ggccttctga gttagctgag gcgggatttt    120
attacacagg agctggggac caaactgtgt gcttttattg tggtggggga ttaaaagact    180
gggatgaagg agatgatcct tgggagcaac atgcccttg gtttagcaaa tgtgtgtttc     240
tcaatttgaa aaagggcaaa gaattcatcg atcaagtaaa gaggaaggct gatccacaat    300
tttcaattcc tggacctagc ggtactcaag ccaaagagga accgactgct actgaatctt    360
caagtgataa acaagtgaa acagtgaaaa caaaatcaga tagggaaagt ttcgcaactg      420
acacaacttt gtgcaaaatt tgctttaaaa acgaacttgg tgttgttttc ttgccttgtg    480
gacatattgt tgcttgtgta ggtaccaagc tgcgaatctt cgttttttta aggaattctc    540
gatctttatg gtgtataggc tctgggtttt ctgtttttg tatctcttag gatttttgtaa    600
attccagatc tttctatggc cacttagtag tatatttcaa aaattctcca atcgagttct    660
tcattcgcat tttcagtcat tttctcttcg acgttgtttt taagcctggg tattactcct    720
atttagttga actctgcagc aatcttagaa aattagggtt ttgaggtttc gatttctcta    780
ggtaaccgat ctattgcatt catctgaatt tctgcatata tgtcttagat ttctgataag    840
cttacgatac gttaggtgta attgaagttt attttttcaag agtgttattt tttgtttctg    900
aatttttcag tcactccatg gcctagtaca caagcaacaa tatgtccaca aggcaagaaa    960
acaacaccaa gttcgttttt aaagcaaatt ttgcacaaag ttgtgtcagt tgcgaaactt   1020
tccctatctg attttgtttt cactgtttca ctttgtttat cacttgaaga ttcagtagca   1080
gtcggttcct ctttggcttg agtaccgcta ggtccaggaa ttgaaaattg tggatcagcc   1140
ttcctctta cttgatcgat gaattctttg ccctttttca aattgagaaa cacacatttg    1200
ctaaaccaaa gggcatgttg ctcccaagga tcatctcctt catcccagtc ttttaatccc   1260
ccaccacaat aaaagcacac agtttggtcc ccagctcctg tgtaataaaa tcccgcctca   1320
gctaactcag aaggcctctg tttaatgctc tttggccaac cctggaatgt tgctaaccgg   1380
cttttctaacg taattttgtc ttgatttttgt ggacctgttc caggtt                 1426

<210> SEQ ID NO 64
<211> LENGTH: 1426
<212> TYPE: DNA
<213> ORGANISM: Artificial Sequence
<220> FEATURE:
<223> OTHER INFORMATION: hpwcrIAP1-Ca/wcrIAP1-Ca*

<400> SEQUENCE: 64

```
aacctggaac aggtccacaa aatcaagaca aaattacgtt agaaagccgg ttagcaacaa      60
tccaggggttg gccaaagagc actaaacaga ggccttctga gttagctgag gcgggatttt    120
attacacagg agctggggac caaactgtgt gcttttattg tggtggggga ttaaaagact    180
gggctgaagg agctgatcct tgggagcaac gtgcccttttg gtttagcaac tgtgtgtttc    240
tcaatttgaa aaagggcaaa gaattcaccg atcaagtaaa gaggaaggct gatccacaat    300
tttcaattcc tggacctagc ggtactcaag ccaaagagga accgactgct actgaatctt    360
caagtgataa acaaagtgaa acagtgaaaa caaaatcaga tagggaaagt ttcgcaactg    420
acacaacttt gtgcaaaatt tgctttaaaa acgaacttgg tgttgttttc ttgccttgtg    480
gacagattgt tgcttgtgta ggtaccaagc tgcgaatctt cgtttttta aggaattctc     540
gatctttatg gtgtataggc tctgggtttt ctgttttttg tatctcttag gattttgtaa    600
attccagatc tttctatggc cacttagtag tatatttcaa aaattctcca atcgagttct    660
tcattcgcat tttcagtcat tttctcttcg acgttgtttt taagcctggg tattactcct    720
atttagttga actctgcagc aatcttagaa aattagggtt ttgaggtttc gatttctcta    780
ggtaaccgat ctattgcatt catctgaatt tctgcatata tgtcttagat ttctgataag    840
cttacgatac gttaggtgta attgaagttt attttttcaag agtgttattt tttgtttctg    900
aatttttcag tcactccatg gcctagtaca caagcaacaa tctgtccaca aggcaagaaa    960
acaacaccaa gttcgttttt aaagcaaatt ttgcacaaag ttgtgtcagt tgcgaaactt   1020
tccctatctg atttttgtttt cactgtttca ctttgtttat cacttgaaga ttcagtagca   1080
gtcggttcct ctttggcttg agtaccgcta ggtccaggaa ttgaaaattg tggatcagcc   1140
ttcctcttta cttgatcggt gaattctttg ccctttttca aattgagaaa cacacagttg   1200
ctaaaccaaa gggcacgttg ctcccaagga tcagctcctt cagcccagtc ttttaatccc   1260
ccaccacaat aaaagcacac agtttggtcc ccagctcctg tgtaataaaa tcccgcctca   1320
gctaactcag aaggcctctg tttagtgctc tttggccaac cctggattgt tgctaaccgg   1380
ctttctaacg taattttgtc ttgattttgt ggacctgttc caggtt                  1426
```

<210> SEQ ID NO 65
<211> LENGTH: 14342
<212> TYPE: DNA
<213> ORGANISM: Artificial Sequence
<220> FEATURE:
<223> OTHER INFORMATION: pRNA21534

<400> SEQUENCE: 65

```
attcctgtgg ttggcatgca catacaaatg gacgaacgga taaaccttt cacgcccttt      60
taaatatccg attattctaa taaacgctct tttctcttag gtttaccgc caatatatcc    120
tgtcaaacac tgatagttta aactggcact agcctaacgg tgttgactaa ctaggccgct    180
tccctaatta gctaacccgg gggcgcgccg ggacccaagc ttctaattag ctaactgcag    240
tgcagcgtga cccggtcgtg cccctctcta gagataatga gcattgcatg tctaagttat    300
aaaaaattac cacatatttt ttttgtcaca cttgtttgaa gtgcagttta tctatcttta    360
tacatatatt taaactttac tctacgaata atataatcta tagtactaca ataatatcag    420
tgttttagag aatcatataa atgaacagtt agacatggtc taaaggacaa ttgagtattt    480
tgacaacagg actctacagt tttatctttt tagtgtgcat gtgttctcct ttttttttgc    540
```

```
aaatagcttc acctatataa tacttcatcc attttattag tacatccatt tagggtttag    600
ggttaatggt ttttatagac taatttttt agtacatcta ttttattcta ttttagcctc    660
taaattaaga aaactaaaac tctattttag ttttttttatt taataattta gatataaaat    720
agaataaaat aaagtgacta aaaattaaac aaataccctt taagaaatta aaaaaactaa    780
ggaaacattt ttcttgtttc gagtagataa tgccagcctg ttaaacgccg ccgacgagtc    840
taacggacac caaccagcga accagcagcg tcgcgtcggg ccaagcgaag cagacggcac    900
ggcatctctg tcgctgcctc tggacccctc tcgagagttc cgctccaccg ttggacttgc    960
tccgctgtcg gcatccagaa attgcgtggc ggagcggcag acgtgagccg gcacggcagg   1020
cggcctcctc ctcctctcac ggcaccggca gctacggggg attcctttcc caccgctcct   1080
tcgctttccc ttcctcgccc gccgtaataa atagacaccc cctccacacc ctctttcccc   1140
aacctcgtgt tgttcggagc gcacacacac acaaccagat ctcccccaaa tccacccgtc   1200
ggcacctccg cttcaaggta cgccgctcgt cctccccccc cccccctctc taccttctct   1260
agatcggcgt tccggtccat agttagggcc cggtagttct acttctgttc atgtttgtgt   1320
tagatccgtg tttgtgttag atccgtgctg ttagcgttcg tacacggatg cgacctgtac   1380
gtcagacacg ttctgattgc taacttgcca gtgtttctct ttggggaatc ctgggatggc   1440
tctagccgtt ccgcagacgg gatcgatttc atgattttt ttgtttcgtt gcatagggtt   1500
tggtttgccc ttttccttta tttcaatata tgccgtgcac ttgtttgtcg ggtcatcttt   1560
tcatgctttt ttttgtcttg gttgtgatga tgtggtctgg ttgggcggtc gttctagatc   1620
ggagtagaat tctgtttcaa actacctggt ggatttatta attttggatc tgtatgtgtg   1680
tgccatacat attcatagtt acgaattgaa gatgatggat ggaaatatcg atctaggata   1740
ggtatacatg ttgatgcggg ttttactgat gcatatacag agatgctttt tgttcgcttg   1800
gttgtgatga tgtggtgtgg ttgggcggtc gttcattcgt tctagatcgg agtagaatac   1860
tgtttcaaac tacctggtgt atttattaat tttggaactg tatgtgtgtg tcatacatct   1920
tcatagttac gagtttaaga tggatggaaa tatcgatcta ggataggtat acatgttgat   1980
gtgggtttta ctgatgcata tacatgatgg catatgcagc atctattcat atgctctaac   2040
cttgagtacc tatctattat aataaacaag tatgttttat aattattttg atcttgatat   2100
acttggatga tggcatatgc agcagctata tgtggatttt tttagccctg ccttcatacg   2160
ctatttattt gcttggtact gtttcttttg tcgatgctca ccctgttgtt tggtgttact   2220
tctgcaggga tcctagatag ttagaacctg gaacaggtcc acaaaatcaa gacaaaatta   2280
cgttagaaag ccggttagca acaatccagg gttggccaaa gagcactaaa cagaggcctt   2340
ctgagttagc tgaggcggga ttttattaca caggagctgg ggaccaaact gtgtgctttt   2400
attgtggtgg gggattaaaa gactgggctg aaggagctga tccttgggag caacgtgccc   2460
tttggtttag caactgtgtg tttctcaatt tgaaaaaggg caaagaattc accgatcaag   2520
taaagaggaa ggctgatcca caattttcaa ttcctggacc tagcggtact caagccaaag   2580
aggaaccgac tgctactgaa tcttcaagtg ataaacaaag tgaaacagtg aaaacaaaat   2640
cagatagggg aagtttcgca actgacacaa ctttgtgcaa aatttgcttt aaaaacgaac   2700
ttggtgttgt tttcttgcct tgtggacaga ttgttgcttg tgtaggtacc aagctgcgaa   2760
tcttcgtttt tttaaggaat tctcgatctt tatggtgtat aggctctggg ttttctgttt   2820
tttgtatctc ttaggatttt gtaaattcca gatcttctta tggccactta gtagtatatt   2880
tcaaaaattc tccaatcgag ttcttcattc gcattttcag tcattttctc ttcgacgttg   2940
```

```
tttttaagcc tgggtattac tcctatttag ttgaactctg cagcaatctt agaaaattag    3000
ggttttgagg tttcgatttc tctaggtaac cgatctattg cattcatctg aatttctgca    3060
tatatgtctt agatttctga taagcttacg atacgttagg tgtaattgaa gtttattttt    3120
caagagtgtt atttttgtt tctgaatttt tcagtcactc catggcctag tacacaagca     3180
acaatctgtc cacaaggcaa gaaaacaaca ccaagttcgt ttttaaagca aattttgcac    3240
aaagttgtgt cagttgcgaa actttcccta tctgattttg ttttcactgt ttcactttgt    3300
ttatcacttg aagattcagt agcagtcggt tcctctttgg cttgagtacc gctaggtcca    3360
ggaattgaaa attgtggatc agccttcctc tttacttgat cggtgaattc tttgcccttt    3420
ttcaaattga gaaacacaca gttgctaaac caaagggcac gttgctccca aggatcagct    3480
ccttcagccc agtcttttaa tcccccacca caataaaagc acacagtttg tccccagct    3540 cctgtgtaat aaaatcccgc ctcagctaac tcagaaggcc tctgtttagt gctctttggc    3600
caaccctgga ttgttgctaa ccggctttct aacgtaattt tgtcttgatt ttgtggacct    3660
gttccaggtt gagctcgcca tcagtcgttg aagctgctgc tgtatctggg ttatctagtg    3720
tctctgccat tgcccaagga tggtgctgtc tttcaaagta tttgtatggt ttgtgtcgtg    3780
agtcgtgact gagctggttt catggaccag ttgtgttctc gttacccaaa actatcgtgc    3840
gaccgcatat ggcttaatca tgaataaatg ttgtttgaat ttaaactatt cgctgaatat    3900
tgttgttttt tgtcatgtca gttaatgtta ctaaattggt tgccttctaa ttttttgttta   3960 ctggtgtttg tcgcaccta tcttttttact gtatgtttac ttcaggttct ggcagtctca    4020 tttttttgtga ctagttaaaa cttacagcta aaaaaatgca gttttcatt ttcatttgaa    4080 gtttgattag agctattgat acccggacca tcaggttagg ttagttgtgc atagaatcat    4140
aaatattaat catgttttct atgaattaag tcaaacttga aagtctggct gaatatagtt    4200
tctatgaatc atattgatat acatgtttga ttatttgttt tgctattagc tatttacttt    4260
ggtgaatcta tataggctta tgcagaacct ttttttttgt tctatatatc catatcctag    4320
tactcagtag ctctatgttt tctggagact agtggcttgc tttttcgtat gtctaatttt    4380
ttgcttgacc attgcaaaac aaaaattacc tagtgtaatc tctttttata ataatcttgt    4440
aatgcgtcta cctataggtc aaagtaggtt ttgtttggaa cccttagagc taactgttag    4500
ctagttgata aattattagc tgagttaagc tagctaatga actagttttg atattagctg    4560
aggatgtttg aaacctaata attatttttt attagctaac tatactaaat tttagtagag    4620
agattccaaa caggagttaa catgggatca gattggctat gcgtttgcaa tcccatacgg    4680
acccggcgcg ccatttaaat ggtaccggac cgcgatcgct taattaagct tgcatgcctg    4740
cagtgcagcg tgacccggtc gtgcccctct ctagagataa tgagcattgc atgtctaagt    4800
tataaaaaat taccacatat tttttttgtc acacttgttt gaagtgcagt ttatctatct    4860
ttatacatat atttaaactt tactctacga ataatataat ctatagtact acaataatat    4920
cagtgtttta gagaatcata taaatgaaca gttagacatg gtctaaagga caattgagta    4980
ttttgacaac aggactctac agttttatct tttagtgtg catgtgttct ccttttttt     5040 tgcaaatagc ttcacctata taatacttca tccattttat tagtacatcc atttagggtt    5100
tagggttaat ggttttata gactaatttt tttagtacat ctattttatt ctattttagc     5160
ctctaaatta agaaaactaa aactctattt tagttttttt atttaataat ttagatataa    5220
aatagaataa aataaagtga ctaaaaatta aacaaatacc ctttaagaaa ttaaaaaaac    5280
```

```
taaggaaaca ttttctttgt ttcgagtaga aatgccagc ctgttaaacg ccgccgacga      5340
gtctaacgga caccaaccag cgaaccagca gcgtcgcgtc gggccaagcg aagcagacgg      5400
cacggcatct ctgtcgctgc ctctggaccc ctctcgagag ttccgctcca ccgttggact      5460
tgctccgctg tcggcatcca gaaattgcgt ggcggagcgg cagacgtgag ccggcacggc      5520
aggcggcctc ctcctcctct cacggcaccg gcagctacgg gggattcctt tcccaccgct      5580
ccttcgcttt cccttcctcg cccgccgtaa taaatagaca ccccctccac accctctttc      5640
cccaacctcg tgttgttcgg agcgcacaca cacacaacca gatctccccc aaatccaccc      5700
gtcggcacct ccgcttcaag gtacgccgct cgtcctcccc cccccccct ctctaccttc       5760
tctagatcgg cgttccggtc catagttagg gcccggtagt tctacttctg ttcatgtttg      5820
tgttagatcc gtgtttgtgt tagatccgtg ctgttagcgt tcgtacacgg atgcgacctg      5880
tacgtcagac acgttctgat tgctaacttg ccagtgtttc tctttgggga atcctgggat      5940
ggctctagcc gttccgcaga cgggatcgat ttcatgattt ttttgtttc gttgcatagg       6000
gtttggtttg ccctttcct ttatttcaat atatgccgtg cacttgtttg tcgggtcatc       6060
ttttcatgct ttttttgtc ttggttgtga tgatgtggtc tggttgggcg gtcgttctag       6120
atcggagtag aattctgttt caaactacct ggtggattta ttaattttgg atctgtatgt      6180
gtgtgccata catattcata gttacgaatt gaagatgatg gatggaaata tcgatctagg      6240
ataggtatac atgttgatgc gggttttact gatgcatata cagagatgct ttttgttcgc      6300
ttggttgtga tgatgtggtg tggttgggcg gtcgttcatt cgttctagat cggagtagaa      6360
tactgtttca aactacctgg tgtatttatt aattttggaa ctgtatgtgt gtgtcataca      6420
tcttcatagt tacgagttta agatggatgg aaatatcgat ctaggatagg tatacatgtt      6480
gatgtgggtt ttactgatgc atatacatga tggcatatgc agcatctatt catatgctct      6540
aaccttgagt acctatctat tataataaac aagtatgttt tataattatt ttgatcttga      6600
tatacttgga tgatggcata tgcagcagct atatgtggat tttttagcc ctgccttcat       6660
acgctattta tttgcttggt actgtttctt ttgtcgatgc tcaccctgtt gtttggtgtt      6720
acttctgcag ggatctccga tcatgcaaaa actcattaac tcagtgcaaa actatgcctg      6780
gggcagcaaa acggcgttga ctgaacttta tggtatggaa aatccgtcca gccagccgat      6840
ggccgagctg tggatgggcg cacatccgaa aagcagttca cgagtgcaga atgccgccgg      6900
agatatcgtt tcactgcgtg atgtgattga gagtgataaa tcgactctgc tcggagaggc      6960
cgttgccaaa cgctttggcg aactgccttt cctgttcaaa gtattatgcg cagcacagcc      7020
actctccatt caggttcatc caaacaaaca caattctgaa atcggttttg ccaaagaaaa      7080
tgccgcaggt atcccgatgg atgccgccga gcgtaactat aaagatccta accacaagcc      7140
ggagctggtt tttgcgctga cgcctttcct tgcgatgaac gcgtttcgtg aattttccga      7200
gattgtctcc ctactccagc cggtcgcagg tgcacatccg gcgattgctc acttttaca       7260
acagcctgat gccgaacgtt taagcgaact gttcgccagc ctgttgaata tgcagggtga      7320
agaaaaatcc cgcgcgctgg cgattttaaa atcggccctc gatagccagc agggtgaacc      7380
gtggcaaacg attcgtttaa tttctgaatt ttacccggaa gacagcggtc tgttctcccc      7440
gctattgctg aatgtggtga aattgaaccc tggcgaagcg atgttcctgt tcgctgaaac      7500
accgcacgct tacctgcaag gcgtggcgct ggaagtgatg gcaaactccg ataacgtgct      7560
gcgtgcgggt ctgacgccta aatacattga tattccggaa ctggttgcca atgtgaaatt      7620
cgaagccaaa ccggctaacc agttgttgac ccagccggtg aaacaaggtg cagaactgga      7680
```

```
cttcccgatt ccagtggatg attttgcctt ctcgctgcat gaccttagtg ataaagaaac    7740
caccattagc cagcagagtg ccgccatttt gttctgcgtc gaaggcgatg caacgttgtg    7800
gaaaggttct cagcagttac agcttaaacc gggtgaatca gcgtttattg ccgccaacga    7860
atcaccggtg actgtcaaag gccacggccg tttagcgcgt gtttacaaca agctgtaaga    7920
gcttactgaa aaaattaaca tctcttgcta agctgggtca tgggtcgttt aagctgccga    7980
tgtgcctgcg tcgtctggtg ccctctctcc atatggaggt tgtcaaagta tctgctgttc    8040
gtgtcatgag tcgtgtcagt gttggtttaa taatggaccg gttgtgttgt gtgtgcgtac    8100
tacccagaac tatgacaaat catgaataag tttgatgttt gaaattaaag cctgtgctca    8160
ttatgttctg tctttcagtt gtctcctaat atttgcctcc aggtactggc tatctaccgt    8220
ttcttactta ggaggtgttt gaatgcacta aaactaatag ttagtggcta aaattagtta    8280
aaacatccaa acaccatagc taatagttga actattagct attttggaa aattagttaa     8340 tagtgaggta gttatttgtt agctagctaa ttcaactaac aattttagc caactaacaa     8400 ttagtttcag tgcattcaaa caccccctta atgttaacgt ggttctatct accgtctcct    8460
aatatatggt tgattgttcg gtttgttgct atgctattgg gttctgattg ctgctagttc    8520
ttgctgaatc cagaagttct cgtagtatag ctcagattca tattatttat ttgagtgata    8580
agtgatccag gttattacta tgttagctag gttttttta caaggataaa ttatctgtga     8640
tcataattct tatgaaagct ttatgtttcc tggaggcagt ggcatgcaat gcatgacagc    8700
aacttgatca caccagctga ggtagatacg gtaacaaggt tcttaaatct gttcaccaaa    8760
tcattggaga acacacatac acattcttgc cagtcttggt tagagaaatt tcatgacaaa    8820
atgccaaagc tgtcttgact cttcactttt ggccatgagt cgtgacttag tttggtttaa    8880
tggaccggtt ctcctagctt gttctactca aaactgttgt tgatgcgaat aagttgtgat    8940
ggttgatctc tggattttgt tttgctctca atagtggacg agattagata gcctgcaggc    9000
ccgggggcgc gccctaatta gctaacggcc aggatcgccg cgtgagcctt tagcaactag    9060
ctagattaat taacgcaatc tgttattaag ttgtctaagc gtcaatttgt ttacaccaca    9120
atatatcctg ccaccagcca gccaacagct ccccgaccgg cagctcggca caaaatcacc    9180
actcgataca ggcagcccat cagaattaat tctcatgttt gacagcttat catcgactgc    9240
acggtgcacc aatgcttctg gcgtcaggca gccatcggaa gctgtggtat ggctgtgcag    9300
gtcgtaaatc actgcataat tcgtgtcgct caaggcgcac tcccgttctg gataatgttt    9360
tttgcgccga catcataacg gttctggcaa atattctgaa atgagctgtt gacaattaat    9420
catccggctc gtataatgtg tggaattgtg agcggataac aatttcacac aggaaacaga    9480
ccatgaggga agcgttgatc gccgaagtat cgactcaact atcagaggta gttggcgtca    9540
tcgagcgcca tctcgaaccg acgttgctgg ccgtacattt gtacggctcc gcagtggatg    9600
gcggcctgaa gccacacagt gatattgatt tgctggttac ggtgaccgta aggcttgatg    9660
aaacaacgcg gcgagctttg atcaacgacc ttttggaaac ttcggcttcc cctggagaga    9720
gcgagattct ccgcgctgta gaagtcacca ttgttgtgca cgacgacatc attccgtggc    9780
gttatccagc taagcgcgaa ctgcaatttg gagaatggca gcgcaatgac attcttgcag    9840
gtatcttcga gccagccacg atcgacattg atctggctat cttgctgaca aaagcaagag    9900
aacatagcgt tgccttggta ggtccagcgg cggaggaact ctttgatccg gttcctgaac    9960
aggatctatt tgaggcgcta aatgaaacct aacgctatg gaactcgccg cccgactggg   10020
```

```
ctggcgatga gcgaaatgta gtgcttacgt tgtcccgcat ttggtacagc gcagtaaccg    10080
gcaaaatcgc gccgaaggat gtcgctgccg actgggcaat ggagcgcctg ccggcccagt    10140
atcagcccgt catacttgaa gctaggcagg cttatcttgg acaagaagat cgcttggcct    10200
cgcgcgcaga tcagttggaa gaatttgttc actacgtgaa aggcgagatc accaaagtag    10260
tcggcaaata aagctctagt ggatctccgt acccagggat ctggctcgcg cggacgcac     10320 gacgccgggg cgagaccata ggcgatctcc taaatcaata gtagctgtaa cctcgaagcg    10380
tttcacttgt aacaacgatt gagaattttt gtcataaaat tgaaatactt ggttcgcatt    10440
tttgtcatcc gcggtcagcc gcaattctga cgaactgccc atttagctgg agatgattgt    10500
acatccttca cgtgaaaatt tctcaagcgc tgtgaacaag ggttcagatt ttagattgaa    10560
aggtgagccg ttgaaacacg ttcttcttgt cgatgacgac gtcgctatgc ggcatcttat    10620
tattgaatac cttacgatcc acgccttcaa agtgaccgcg gtagccgaca gcacccagtt    10680
cacaagagta ctctcttccg cgacggtcga tgtcgtggtt gttgatctag atttaggtcg    10740
tgaagatggg ctcgagatcg ttcgtaatct ggcggcaaag tctgatattc caatcataat    10800
tatcagtggc gaccgccttg aggagacgga taaagttgtt gcactcgagc taggagcaag    10860
tgattttatc gctaagccgt tcagtatcag agagtttcta gcacgcattc gggttgcctt    10920
gcgcgtgcgc cccaacgttg tccgctccaa agaccgacgg tcttttttgtt ttactgactg    10980 gacacttaat ctcaggcaac gtcgcttgat gtccgaagct ggcggtgagg tgaaacttac    11040
ggcaggtgag ttcaatcttc tcctcgcgtt tttagagaaa ccccgcgacg ttctatcgcg    11100
cgagcaactt ctcattgcca gtcgagtacg cgacgaggag gtttatgaca ggagtataga    11160
tgttctcatt ttgaggctgc gccgcaaact tgaggcagat ccgtcaagcc ctcaactgat    11220
aaaaacagca agaggtgccg gttatttctt tgacgcggac gtgcaggttt cgcacggggg    11280
gacgatggca gcctgagcca attcccagat ccccgaggaa tcggcgtgag cggtcgcaaa    11340
ccatccggcc cggtacaaat cggcgcggcg ctgggtgatg acctggtgga aagttgaag     11400 gccgcgcagg ccgcccagcg gcaacgcatc gaggcagaag cacgccccgg tgaatcgtgg    11460
caagcggccg ctgatcgaat ccgcaaagaa tcccggcaac cgccggcagc cggtgcgccg    11520
tcgattagga agccgcccaa gggcgacgag caaccagatt ttttcgttcc gatgctctat    11580
gacgtgggca cccgcgatag tcgcagcatc atggacgtgg ccgttttccg tctgtcgaag    11640
cgtgaccgac gagctggcga ggtgatccgc tacgagcttc cagacgggca cgtagaggtt    11700
tccgcagggc cggccggcat ggccagtgtg tgggattacg acctggtact gatggcggtt    11760
tcccatctaa ccgaatccat gaaccgatac cgggaaggga agggagacaa gcccggccgc    11820
gtgttccgtc cacacgttgc ggacgtactc aagttctgcc ggcagccgaa tggcggaaag    11880
cagaaagacg acctggtaga aacctgcatt cggttaaaca ccacgcacgt tgccatgcag    11940
cgtacgaaga aggccaagaa cggccgcctg gtgacggtat ccgagggtga agccttgatt    12000
agccgctaca agatcgtaaa gagcgaaacc gggcggccgg agtacatcga atcgagctg     12060 gctgattgga tgtaccgcga gatcacagaa ggcaagaacc cggacgtgct gacggttcac    12120
cccgattact ttttgatcga tcccggcatc ggccgttttc tctaccgcct ggcacgccgc    12180
gccgcaggca aggcagaagc cagatggttg ttcaagacga tctacgaacg cagtggcagc    12240
gccggagagt tcaagaagtt ctgttttcacc gtgcgcaagc tgatcgggtc aaatgacctg    12300
ccggagtacg atttgaagga ggaggcgggg caggctggcc cgatcctagt catgcgctac    12360
cgcaacctga tcgagggcga agcatccgcc ggttcctaat gtacggagca gatgctaggg    12420
```

```
caaattgccc tagcagggga aaaaggtcga aaaggtctct ttcctgtgga tagcacgtac    12480
attgggaacc caaagccgta cattgggaac cggaacccgt acattgggaa cccaaagccg    12540
tacattggga accggtcaca catgtaagtg actgatataa aagagaaaaa aggcgatttt    12600
tccgcctaaa actctttaaa acttattaaa actcttaaaa cccgcctggc ctgtgcataa    12660
ctgtctggcc agcgcacagc cgaagagctg caaaaagcgc ctacccttcg gtcgctgcgc    12720
tccctacgcc ccgccgcttc gcgtcggcct atcgcggccg ctggccgctc aaaaatggct    12780
ggcctacggc caggcaatct accagggcgc ggacaagccg cgccgtcgcc actcgaccgc    12840
cggcgctgag gtctgcctcg tgaagaaggt gttgctgact cataccaggc ctgaatcgcc    12900
ccatcatcca gccagaaagt gagggagcca cggttgatga gagctttgtt gtaggtggac    12960
cagttggtga ttttgaactt ttgctttgcc acggaacggt ctgcgttgtc gggaagatgc    13020
gtgatctgat ccttcaactc agcaaaagtt cgatttattc aacaaagccg ccgtcccgtc    13080
aagtcagcgt aatgctctgc cagtgttaca accaattaac caattctgat tagaaaaact    13140
catcgagcat caaatgaaac tgcaatttat tcatatcagg attatcaata ccatattttt    13200
gaaaaagccg tttctgtaat gaaggagaaa actcaccgag gcagttccat aggatggcaa    13260
gatcctggta tcggtctgcg attccgactc gtccaacatc aatacaacct attaatttcc    13320
cctcgtcaaa aataaggtta tcaagtgaga atcaccatg agtgacgact gaatccggtg    13380
agaatggcaa aagctctgca ttaatgaatc ggccaacgcg cggggagagg cggtttgcgt    13440
attgggcgct cttccgcttc ctcgctcact gactcgctgc gctcggtcgt tcggctgcgg    13500
cgagcggtat cagctcactc aaaggcggta atacggttat ccacagaatc aggggataac    13560
gcaggaaaga acatgtgagc aaaaggccag caaaaggcca ggaaccgtaa aaaggccgcg    13620
ttgctggcgt ttttccatag gctccgcccc cctgacgagc atcacaaaaa tcgacgctca    13680
agtcagaggt ggcgaaaccc gacaggacta taaagatacc aggcgtttcc ccctggaagc    13740
tccctcgtgc gctctcctgt tccgaccctg ccgcttaccg gatacctgtc cgcctttctc    13800
ccttcgggaa gcgtggcgct ttctcatagc tcacgctgta ggtatctcag ttcggtgtag    13860
gtcgttcgct ccaagctggg ctgtgtgcac gaaccccccg ttcagcccga ccgctgcgcc    13920
ttatccggta actatcgtct tgagtccaac ccggtaagac acgacttatc gccactggca    13980
gcagccactg gtaacaggat tagcagagcg aggtatgtag cggtgctac agagttcttg    14040 aagtggtggc ctaactacgg ctacactaga agaacagtat ttggtatctg cgctctgctg    14100
aagccagtta ccttcggaaa aagagttggt agctcttgat ccggcaaaca aaccaccgct    14160
ggtagcggtg gttttttgt ttgcaagcag cagattacgc gcagaaaaaa aggatctcaa    14220
gaagatcctt tgatcttttc tacggggtct gacgctcagt ggaacgaaaa ctcacgttaa    14280
gggattttgg tcatgagatt atcaaaaagg atcttcacct agatccttt gatccggaat    14340 ta                                                                   14342
```

<210> SEQ ID NO 66
<211> LENGTH: 14326
<212> TYPE: DNA
<213> ORGANISM: Artificial Sequence
<220> FEATURE:
<223> OTHER INFORMATION: pRNA21536

<400> SEQUENCE: 66

```
attcctgtgg ttggcatgca catacaaatg gacgaacgga taaacctttt cacgcccttt       60
```

```
taaatatccg attattctaa taaacgctct tttctcttag gtttacccgc caatatatcc        120
tgtcaaacac tgatagttta aactggcact agcctaacgg tgttgactaa ctaggccgct        180
tccctaatta gctaacccgg gggcgcgccg ggacccaagc ttctaattag ctaactgcag        240
tgcagcgtga cccggtcgtg cccctctcta gagataatga gcattgcatg tctaagttat        300
aaaaaattac cacatatttt ttttgtcaca cttgtttgaa gtgcagttta tctatcttta        360
tacatatatt taaactttac tctacgaata atataatcta tagtactaca ataatatcag        420
tgttttagag aatcatataa atgaacagtt agacatggtc taaaggacaa ttgagtattt        480
tgacaacagg actctacagt tttatctttt tagtgtgcat gtgttctcct ttttttttgc        540
aaatagcttc acctatataa tacttcatcc attttattag tacatccatt tagggtttag        600
ggttaatggt ttttatagac taatttttt agtacatcta ttttattcta ttttagcctc        660
taaattaaga aaactaaaac tctattttag tttttttatt taataattta gatataaaat        720
agaataaaat aaagtgacta aaattaaac aatacccctt taagaaatta aaaaaactaa        780
ggaaacattt ttcttgtttc gagtagataa tgccagcctg ttaaacgccg ccgacgagtc        840
taacggacac caaccagcga accagcagcg tcgcgtcggg ccaagcgaag cagacggcac        900
ggcatctctg tcgctgcctc tggacccctc tcgagagttc cgctccaccg ttggacttgc        960
tccgctgtcg gcatccagaa attgcgtggc ggagcggcag acgtgagccg gcacggcagg       1020
cggcctcctc ctcctctcac ggcaccggca gctacggggg attcctttcc caccgctcct       1080
tcgctttccc ttcctcgccc gccgtaataa atagacaccc cctccacacc ctctttcccc       1140
aacctcgtgt tgttcggagc gcacacacac acaaccagat ctcccccaaa tccacccgtc       1200
ggcacctccg cttcaaggta cgccgctcgt cctccccccc cccccctctc taccttctct       1260
agatcggcgt tccggtccat agttagggcc cggtagttct acttctgttc atgtttgtgt       1320
tagatccgtg tttgtgttag atccgtgctg ttagcgttcg tacacggatg cgacctgtac       1380
gtcagacacg ttctgattgc taacttgcca gtgtttctct ttggggaatc ctgggatggc       1440
tctagccgtt ccgcagacgg gatcgatttc atgattttt ttgtttcgtt gcatagggtt       1500
tggtttgccc ttttccttta tttcaatata tgccgtgcac ttgtttgtcg ggtcatctt       1560 tcatgctttt ttttgtcttg gttgtgatga tgtggtctgg ttgggcggtc gttctagatc       1620
ggagtagaat tctgtttcaa actacctggt ggatttatta atttggatc tgtatgtgtg       1680 tgccatacat attcatagtt acgaattgaa gatgatggat ggaaatatcg atctaggata       1740
ggtatacatg ttgatgcggg ttttactgat gcatatacag agatgctttt tgttcgcttg       1800
gttgtgatga tgtggtgtgg ttgggcggtc gttcattcgt tctagatcgg agtagaatac       1860
tgtttcaaac tacctggtgt atttattaat tttggaactg tatgtgtgtg tcatacatct       1920
tcatagttac gagtttaaga tggatggaaa tatcgatcta ggataggtat acatgttgat       1980
gtgggtttta ctgatgcata tacatgatgg catatgcagc atctattcat atgctctaac       2040
cttgagtacc tatctattat aataaacaag tatgttttat aattattttg atcttgatat       2100
acttggatga tggcatatgc agcagctata tgtggatttt tttagccctg ccttcatacg       2160
ctatttattt gcttggtact gtttcttttg tcgatgctca ccctgttgtt tggtgttact       2220
tctgcaggga tccaaaagaa gtgccgagca actcggtggc gagccgagat cgataggaat       2280
actgtgcccg tactagaact gtaacttctt atatgtcgct atttcacttc cctcaaacga       2340
gccgctgctg gcggaacgat tttacctctc gattttaatt gtacgctgtc ggaaggaccc       2400
aaaacatttt atcgaagtat accacgcatt tccgtgctct tactggcggt aagctaggca       2460
```

```
tcctatcact gcatacgccc tctatttta tattgacgtt atgaactctc ggcgacaatt    2520
ctgctactag atggttgtcc tcccgtcact tagggctat tccccgttcg cctactatca    2580
tccatagatc gcatgcgcca ctggtttaat cgtttattgt ggatctcaag gtgaatacct    2640
tcaacttcgc cagcactaaa gagcatatgt atccgttagc tattcggcct gacggatcgt    2700
agtcctaacc aagcactttc tgatagtttt aaaggtacca agctgcgaat cttcgttttt    2760
ttaaggaatt ctcgatcttt atggtgtata ggctctgggt tttctgtttt ttgtatctct    2820
taggattttg taaattccag atctttctat ggccacttag tagtatattt caaaaattct    2880
ccaatcgagt tcttcattcg cattttcagt cattttctct tcgacgttgt ttttaagcct    2940
gggtattact cctatttagt tgaactctgc agcaatctta gaaaattagg gttttgaggt    3000
ttcgatttct ctaggtaacc gatctattgc attcatctga atttctgcat atatgtctta    3060
gatttctgat aagcttacga tacgttaggt gtaattgaag tttattttc aagagtgtta    3120 ttttttgttt ctgaattttt cagtcactcc atggtttaaa actatcagaa agtgcttggt    3180
taggactacg atccgtcagg ccgaatagct aacggataca tatgctcttt agtgctggcg    3240
aagttgaagg tattcacctt gagatccaca ataaacgatt aaaccagtgg cgcatgcgat    3300
ctatggatga tagtaggcga acggggaata gcccctaagt gacgggagga caaccatcta    3360
gtagcagaat tgtcgccgag agttcataac gtcaatataa aaatagaggg cgtatgcagt    3420
gataggatgc ctagcttacc gccagtaaga gcacggaaat gcgtggtata cttcgataaa    3480
atgttttggg tccttccgac agcgtacaat taaaatcgag aggtaaaatc gttccgccag    3540
cagcggctcg tttgagggaa gtgaaatagc gacatataag aagttacagt tctagtacgg    3600
gcacagtatt cctatcgatc tcggctcgcc accgagttgc tcggcacttc ttttgagctc    3660
gccatcagtc gttgaagctg ctgctgtatc tgggttatct agtgtctctg ccattgccca    3720
aggatggtgc tgtctttcaa agtatttgta tggtttgtgt cgtgagtcgt gactgagctg    3780
gtttcatgga ccagttgtgt tctcgttacc caaaactatc gtgcgaccgc atatggctta    3840
atcatgaata aatgttgttt gaatttaaac tattcgctga atattgttgt ttttttgtcat    3900 gtcagttaat gttactaaat tggttgcctt ctaatttttg tttactggtg tttgtcgcac    3960
cttatctttt tactgtatgt ttacttcagg ttctggcagt ctcatttttt gtgactagtt    4020
aaaacttaca gctaaaaaaa tgcagttttt cattttcatt tgaagtttga ttagagctat    4080
tgatacccgg accatcaggt taggttagtt gtgcatagaa tcataaatat taatcatgtt    4140
ttctatgaat taagtcaaac ttgaaagtct ggctgaatat agtttctatg aatcatattg    4200
atatacatgt ttgattattt gttttgctat tagctattta ctttggtgaa tctatatagg    4260
cttatgcaga accttttttt ttgttctata tatccatatc ctagtactca gtagctctat    4320
gttttctgga gactagtggc ttgcttttc gtatgtctaa tttttttgctt gaccattgca    4380 aaacaaaaat tacctagtgt aatctctttt tataataatc ttgtaatgcg tctacctata    4440
ggtcaaagta ggttttgttt ggaacccta gagctaactg ttagctagtt gataaattat    4500
tagctgagtt aagctagcta atgaactagt tttgatatta gctgaggatg tttgaaacct    4560
aataattatt ttttattagc taactatact aaattttagt agagagattc caaacaggag    4620
ttaacatggg atcagattgg ctatgcgttt gcaatcccat acggacccgg cgcgccattt    4680
aaatggtacc ggaccgcgat cgcttaatta agcttgcatg cctgcagtgc agcgtgaccc    4740
ggtcgtgccc ctctctagag ataatgagca ttgcatgtct aagttataaa aaattaccac    4800
```

```
atatttttt tgtcacactt gtttgaagtg cagtttatct atctttatac atatatttaa    4860
actttactct acgaataata taatctatag tactacaata atatcagtgt tttagagaat    4920
catataaatg aacagttaga catggtctaa aggacaattg agtattttga caacaggact    4980
ctacagtttt atcttttttag tgtgcatgtg ttctccttt ttttttgcaaa tagcttcacc    5040
tatataatac ttcatccatt ttattagtac atccatttag ggtttagggt taatggtttt    5100
tatagactaa ttttttttagt acatctattt tattctattt tagcctctaa attaagaaaa    5160
ctaaaactct attttagttt ttttatttaa taatttagat ataaaataga ataaaataaa    5220
gtgactaaaa attaaacaaa taccctttaa gaaattaaaa aaactaagga aacatttttc    5280
ttgtttcgag tagataatgc cagcctgtta aacgccgccg acgagtctaa cggacaccaa    5340
ccagcgaacc agcagcgtcg cgtcgggcca agcgaagcag acggcacggc atctctgtcg    5400
ctgcctctgg accccctctcg agagttccgc tccaccgttg gacttgctcc gctgtcggca    5460
tccagaaatt gcgtggcgga gcggcagacg tgagccggca cggcaggcgg cctcctcctc    5520
ctctcacggc accggcagct acgggggatt ccttccccac cgctccttcg ctttcccttc    5580
ctcgcccgcc gtaataaata gacacccccct ccacaccctc ttttcccaac ctcgtgttgt    5640
tcggagcgca cacacacaca accagatctc ccccaaatcc acccgtcggc acctccgctt    5700
caaggtacgc cgctcgtcct ccccccccccc ccctctctac cttctctaga tcggcgttcc    5760
ggtccatagt tagggcccgg tagttctact tctgttcatg tttgtgttag atccgtgttt    5820
gtgttagatc cgtgctgtta gcgttcgtac acggatgcga cctgtacgtc agacacgttc    5880
tgattgctaa cttgccagtg tttctctttg gggaatcctg ggatggctct agccgttccg    5940
cagacgggat cgatttcatg attttttttg tttcgttgca tagggtttgg tttgcccttt    6000
tcctttatt caatatatgc cgtgcacttg tttgtcgggt catcttttca tgctttttt    6060
tgtcttggtt gtgatgatgt ggtctggttg ggcggtcgtt ctagatcgga gtagaattct    6120
gtttcaaact acctggtgga tttattaatt ttggatctgt atgtgtgtgc catacatatt    6180
catagttacg aattgaagat gatggatgga aatatcgatc taggataggt atacatgttg    6240
atgcgggttt tactgatgca tatacagaga tgcttttttgt tcgcttggtt gtgatgatgt    6300
ggtgtggttg ggcggtcgtt cattcgttct agatcggagt agaatactgt ttcaaactac    6360
ctggtgtatt tattaatttt ggaactgtat gtgtgtgtca tacatcttca tagttacgag    6420
tttaagatgg atggaaatat cgatctagga taggtataca tgttgatgtg ggttttactg    6480
atgcatatac atgatggcat atgcagcatc tattcatatg ctctaacctt gagtacctat    6540
ctattataat aaacaagtat gttttataat tattttgatc ttgatatact tggatgatgg    6600
catatgcagc agctatatgt ggattttttt agccctgcct tcatacgcta tttatttgct    6660
tggtactgtt tcttttgtcg atgctcaccc tgttgtttgg tgttacttct gcagggatct    6720
ccgatcatgc aaaaactcat taactcagtg caaaactatg cctggggcag caaaacggcg    6780
ttgactgaac tttatggtat ggaaaatccg tccagccagc cgatggccga gctgtggatg    6840
ggcgcacatc cgaaaagcag ttcacgagtg cagaatgccg ccggagatat cgtttcactg    6900
cgtgatgtga ttgagagtga taaatcgact ctgctcggag aggccgttgc caaacgcttt    6960
ggcgaactgc cttcctgtt caaagtatta tgcgcagcac agccactctc cattcaggtt    7020
catccaaaca aacacaattc tgaaatcggt tttgccaaag aaaatgccgc aggtatcccg    7080
atggatgccg ccgagcgtaa ctataaagat cctaaccaca agccggagct ggttttgcg    7140
ctgacgcctt tccttgcgat gaacgcgttt cgtgaatttt ccgagattgt ctccctactc    7200
```

```
cagccggtcg caggtgcaca tccggcgatt gctcactttt tacaacagcc tgatgccgaa    7260
cgtttaagcg aactgttcgc cagcctgttg aatatgcagg gtgaagaaaa atcccgcgcg    7320
ctggcgattt aaaatcggc cctcgatagc cagcagggtg aaccgtggca acgattcgt    7380 ttaatttctg aattttaccc ggaagacagc ggtctgttct ccccgctatt gctgaatgtg    7440
gtgaaattga accctggcga agcgatgttc ctgttcgctg aaacaccgca cgcttacctg    7500
caaggcgtgg cgctggaagt gatggcaaac tccgataacg tgctgcgtgc gggtctgacg    7560
cctaaataca ttgatattcc ggaactggtt gccaatgtga aattcgaagc caaaccggct    7620
aaccagttgt tgacccagcc ggtgaaacaa ggtgcagaac tggacttccc gattccagtg    7680
gatgattttg ccttctcgct gcatgacctt agtgataaag aaaccaccat tagccagcag    7740
agtgccgcca ttttgttctg cgtcgaaggc gatgcaacgt tgtggaaagg ttctcagcag    7800
ttacagctta aaccgggtga atcagcgttt attgccgcca acgaatcacc ggtgactgtc    7860
aaaggccacg gccgtttagc gcgtgtttac aacaagctgt aagagcttac tgaaaaaatt    7920
aacatctctt gctaagctgg gtcatgggtc gtttaagctg ccgatgtgcc tgcgtcgtct    7980
ggtgccctct ctccatatgg aggttgtcaa agtatctgct gttcgtgtca tgagtcgtgt    8040
cagtgttggt ttaataatgg accggttgtg ttgtgtgtgc gtactaccca gaactatgac    8100
aaatcatgaa taagtttgat gtttgaaatt aaagcctgtg ctcattatgt tctgtctttc    8160
agttgtctcc taatatttgc ctccaggtac tggctatcta ccgtttctta cttaggaggt    8220
gtttgaatgc actaaaacta atagttagtg gctaaaatta gttaaaacat ccaaacacca    8280
tagctaatag ttgaactatt agctattttt ggaaaattag ttaatagtga ggtagttatt    8340
tgttagctag ctaattcaac taacaatttt tagccaacta acaattagtt tcagtgcatt    8400
caaacacccc cttaatgtta acgtggttct atctaccgtc tcctaatata tggttgattg    8460 ttcggttttgt tgctatgcta ttgggttctg attgctgcta gttcttgctg aatccagaag    8520
ttctcgtagt atagctcaga ttcatattat ttatttgagt gataagtgat ccaggttatt    8580
actatgttag ctaggttttt tttacaagga taaattatct gtgatcataa ttcttatgaa    8640
agctttatgt ttcctggagg cagtggcatg caatgcatga cagcaacttg atcacaccag    8700
ctgaggtaga tacggtaaca aggttcttaa atctgttcac caaatcattg gagaacacac    8760
atacacattc ttgccagtct tggttagaga aatttcatga caaaatgcca aagctgtctt    8820
gactcttcac ttttggccat gagtcgtgac ttagtttggt ttaatggacc ggttctccta    8880
gcttgttcta ctcaaaactg ttgttgatgc gaataagttg tgatggttga tctctggatt    8940
ttgttttgct ctcaatagtg gacgagatta gatagcctgc aggcccgggg gcgcgcccta    9000
attagctaac ggccaggatc gccgcgtgag ccttttagcaa ctagctagat taattaacgc    9060
aatctgttat taagttgtct aagcgtcaat ttgtttacac cacaatatat cctgccacca    9120
gccagccaac agctccccga ccggcagctc ggcacaaaat caccactcga tacaggcagc    9180
ccatcagaat taattctcat gtttgacagc ttatcatcga ctgcacggtg caccaatgct    9240
tctggcgtca ggcagccatc ggaagctgtg gtatggctgt gcaggtcgta atcactgca    9300 taattcgtgt cgctcaaggc gcactcccgt tctggataat gttttttgcg ccgacatcat    9360
aacggttctg gcaaatattc tgaaatgagc tgttgacaat taatcatccg gctcgtataa    9420
tgtgtggaat tgtgagcgga taacaatttc acacaggaaa cagaccatga gggaagcgtt    9480
gatcgccgaa gtatcgactc aactatcaga ggtagttggc gtcatcgagc gccatctcga    9540
```

```
accgacgttg ctggccgtac atttgtacgg ctccgcagtg gatggcggcc tgaagccaca   9600
cagtgatatt gatttgctgg ttacggtgac cgtaaggctt gatgaaacaa cgcggcgagc   9660
tttgatcaac gaccttttgg aaacttcggc ttcccctgga gagagcgaga ttctccgcgc   9720
tgtagaagtc accattgttg tgcacgacga catcattccg tggcgttatc cagctaagcg   9780
cgaactgcaa tttggagaat ggcagcgcaa tgacattctt gcaggtatct tcgagccagc   9840
cacgatcgac attgatctgg ctatcttgct gacaaaagca agagaacata gcgttgcctt   9900
ggtaggtcca gcggcggagg aactctttga tccggttcct gaacaggatc tatttgaggc   9960
gctaaatgaa accttaacgc tatggaactc gccgcccgac tgggctggcg atgagcgaaa  10020
tgtagtgctt acgttgtccc gcatttggta cagcgcagta accggcaaaa tcgcgccgaa  10080
ggatgtcgct gccgactggg caatggagcg cctgccggcc cagtatcagc ccgtcatact  10140
tgaagctagg caggcttatc ttggacaaga agatcgcttg gcctcgcgcg cagatcagtt  10200
ggaagaattt gttcactacg tgaaaggcga gatcaccaaa gtagtcggca aataaagctc  10260
tagtggatct ccgtacccag ggatctggct cgcggcggac gcacgacgcc ggggcgagac  10320
cataggcgat ctcctaaatc aatagtagct gtaacctcga agcgtttcac ttgtaacaac  10380
gattgagaat ttttgtcata aaattgaaat acttggttcg cattttttgtc atccgcggtc  10440 agccgcaatt ctgacgaact gcccatttag ctggagatga ttgtacatcc ttcacgtgaa  10500
aatttctcaa gcgctgtgaa caagggttca gatttttagat tgaaaggtga gccgttgaaa  10560
cacgttcttc ttgtcgatga cgacgtcgct atgcggcatc ttattattga ataccttacg  10620
atccacgcct tcaaagtgac cgcggtagcc gacagcaccc agttcacaag agtactctct  10680
tccgcgacgg tcgatgtcgt ggttgttgat ctagatttag gtcgtgaaga tgggctcgag  10740
atcgttcgta atctggcggc aaagtctgat attccaatca taattatcag tggcgaccgc  10800
cttgaggaga cggataaagt tgttgcactc gagctaggag caagtgattt tatcgctaag  10860
ccgttcagta tcagagagtt tctagcacgc attcgggttg ccttgcgcgt gcgccccaac  10920
gttgtccgct ccaaagaccg acggtctttt tgttttactg actggacact taatctcagg  10980
caacgtcgct tgatgtccga agctggcggt gaggtgaaac ttacggcagg tgagttcaat  11040
cttctcctcg cgttttttaga gaaaccccgc gacgttctat cgcgcgagca acttctcatt  11100
gccagtcgag tacgcgacga ggaggtttat gacaggagta tagatgttct cattttgagg  11160
ctgcgccgca aacttgaggc agatccgtca agccctcaac tgataaaaac agcaagaggt  11220
gccggttatt tctttgacgc ggacgtgcag gtttcgcacg ggggacgat ggcagcctga  11280 gccaattccc agatccccga ggaatcggcg tgagcggtcg caaaccatcc ggcccggtac  11340
aaatcggcgc ggcgctgggt gatgacctgg tggagaagtt gaaggccgcg caggccgccc  11400
agcggcaacg catcgaggca gaagcacgcc ccggtgaatc gtggcaagcg gccgctgatc  11460
gaatccgcaa agaatcccgg caaccgccgg cagccggtgc gccgtcgatt aggaagccgc  11520
ccaagggcga cgagcaacca gatttttttcg ttccgatgct ctatgacgtg gcacccgcg  11580 atagtcgcag catcatggac gtggccgttt tccgtctgtc gaagcgtgac cgacgagctg  11640
gcgaggtgat ccgctacgag cttccagacg ggcacgtaga ggtttccgca gggccggccg  11700
gcatggccag tgtgtgggat tacgacctgg tactgatggc ggtttcccat ctaaccgaat  11760
ccatgaaccg ataccgggaa gggaagggag acaagcccgg ccgcgtgttc cgtccacacg  11820
ttgcggacgt actcaagttc tgccggcgag ccgatggcgg aaagcagaaa gacgacctgg  11880
tagaaacctg cattcggtta aacaccacgc acgttgccat gcagcgtacg aagaaggcca  11940
```

```
agaacggccg cctggtgacg gtatccgagg gtgaagcctt gattagccgc tacaagatcg   12000
taaagagcga aaccgggcgg ccggagtaca tcgagatcga gctggctgat tggatgtacc   12060
gcgagatcac agaaggcaag aacccggacg tgctgacggt tcaccccgat tacttttttga  12120 tcgatcccgg catcggccgt tttctctacc gcctggcacg ccgcgccgca ggcaaggcag   12180
aagccagatg gttgttcaag acgatctacg aacgcagtgg cagcgccgga gagttcaaga   12240
agttctgttt caccgtgcgc aagctgatcg ggtcaaatga cctgccggag tacgatttga   12300
aggaggaggc ggggcaggct ggcccgatcc tagtcatgcg ctaccgcaac ctgatcgagg   12360
gcgaagcatc cgccggttcc taatgtacgg agcagatgct agggcaaatt gccctagcag   12420
gggaaaaagg tcgaaaaggt ctcttttcctg tggatagcac gtacattggg aacccaaagc  12480
cgtacattgg gaaccggaac ccgtacattg ggaacccaaa gccgtacatt gggaaccggt   12540
cacacatgta agtgactgat ataaaagaga aaaaggcga ttttttccgcc taaaactctt   12600 taaaacttat taaaactctt aaaacccgcc tggcctgtgc ataactgtct ggccagcgca   12660
cagccgaaga gctgcaaaaa gcgcctaccc ttcggtcgct gcgctcccta cgccccgccg   12720
cttcgcgtcg gccatcgcg gccgctggcc gctcaaaaat ggctggccta cggcaggca    12780 atctaccagg gcgcggacaa gccgcgccgt cgccactcga ccgccggcgc tgaggtctgc   12840
ctcgtgaaga aggtgttgct gactcatacc aggcctgaat cgccccatca tccagccaga   12900
aagtgaggga gccacggttg atgagagctt tgttgtaggt ggaccagttg gtgattttga   12960
acttttgctt tgccacggaa cggtctgcgt tgtcgggaag atgcgtgatc tgatccttca   13020
actcagcaaa agttcgattt attcaacaaa gccgccgtcc cgtcaagtca gcgtaatgct   13080
ctgccagtgt tacaaccaat taaccaattc tgattagaaa aactcatcga gcatcaaatg   13140
aaactgcaat ttattcatat caggattatc aataccatat ttttgaaaaa gccgtttctg   13200
taatgaagga gaaactcac cgaggcagtt ccataggatg gcaagatcct ggtatcggtc   13260
tgcgattccg actcgtccaa catcaataca acctattaat ttcccctcgt caaaaataag   13320
gttatcaagt gagaaatcac catgagtgac gactgaatcc ggtgagaatg gcaaaagctc   13380
tgcattaatg aatcggccaa cgcgcgggga gaggcggttt gcgtattggg cgctcttccg   13440
cttcctcgct cactgactcg ctgcgctcgg tcgttcggct gcggcgagcg gtatcagctc   13500
actcaaaggc ggtaatacgg ttatccacag aatcagggga taacgcagga aagaacatgt   13560
gagcaaaagg ccagcaaaag gccaggaacc gtaaaaaggc cgcgttgctg gcgttttttcc  13620 ataggctccg cccccctgac gagcatcaca aaaatcgacg ctcaagtcag aggtggcgaa   13680
acccgacagg actataaaga taccaggcgt ttccccctgg aagctccctc gtgcgctctc   13740
ctgttccgac cctgccgctt accggatacc tgtccgcctt tctcccttcg ggaagcgtgg   13800
cgctttctca tagctcacgc tgtaggtatc tcagttcggt gtaggtcgtt cgctccaagc   13860
tgggctgtgt gcacgaaccc cccgttcagc ccgaccgctg cgccttatcc ggtaactatc   13920
gtcttgagtc aacccggta agacacgact tatcgccact ggcagcagcc actggtaaca   13980
ggattagcag agcgaggtat gtaggcggtg ctacagagtt cttgaagtgg tggcctaact   14040
acggctacac tagaagaaca gtatttggta tctgcgctct gctgaagcca gttaccttcg   14100
gaaaaagagt tggtagctct tgatccggca aacaaaccac cgctggtagc ggtggttttt   14160
ttgtttgcaa gcagcagatt acgcgcagaa aaaaaggatc tcaagaagat cctttgatct   14220
tttctacggg gtctgacgct cagtggaacg aaaactcacg ttaagggatt ttggtcatga   14280
```

| | |
|---|---:|
| gattatcaaa aaggatcttc acctagatcc ttttgatccg aatta | 14326 |

<210> SEQ ID NO 67
<211> LENGTH: 14331
<212> TYPE: DNA
<213> ORGANISM: Artificial Sequence
<220> FEATURE:
<223> OTHER INFORMATION: pRNA21537

<400> SEQUENCE: 67

| | |
|---|---:|
| attcctgtgg ttggcatgca catacaaatg gacgaacgga taaacctttt cacgcccttt | 60 |
| taaatatccg attattctaa taaacgctct tttctcttag gtttacccgc caatatatcc | 120 |
| tgtcaaacac tgatagttta aactggcact agcctaacgg tgttgactaa ctaggccgct | 180 |
| tccctaatta gctaacccgg gggcgcgccg ggacccaagc ttctaattag ctaactgcag | 240 |
| tgcagcgtga cccggtcgtg cccctctcta gagataatga gcattgcatg tctaagttat | 300 |
| aaaaaattac cacatatttt ttttgtcaca cttgtttgaa gtgcagttta tctatcttta | 360 |
| tacatatatt taaactttac tctacgaata atataatcta tagtactaca ataatatcag | 420 |
| tgttttagag aatcatataa atgaacagtt agacatggtc taaaggacaa ttgagtattt | 480 |
| tgacaacagg actctacagt tttatctttt tagtgtgcat gtgttctcct tttttttttgc | 540 |
| aaatagcttc acctatataa tacttcatcc atttttattag tacatccatt tagggtttag | 600 |
| ggttaatggt tttatagac taattttttt agtacatcta ttttattcta ttttagcctc | 660 |
| taaattaaga aaactaaaac tctattttag tttttttatt taataattta gatataaaat | 720 |
| agaataaaat aaagtgacta aaattaaac aaatacccctt taagaaatta aaaaaactaa | 780 |
| ggaaacattt ttcttgtttc gagtagataa tgccagcctg ttaaacgccg ccgacgagtc | 840 |
| taacggacac caaccagcga accagcagcg tcgcgtcggg ccaagcgaag cagacggcac | 900 |
| ggcatctctg tcgctgcctc tggacccctc tcgagagttc cgctccaccg ttggacttgc | 960 |
| tccgctgtcg gcatccagaa attgcgtggc ggagcggcag acgtgagccg gcacggcagg | 1020 |
| cggcctcctc ctcctctcac ggcaccggca gctacggggg attccttttcc caccgctcct | 1080 |
| tcgctttccc ttcctcgccc gccgtaataa atagacaccc cctccacacc ctcttttcccc | 1140 |
| aacctcgtgt tgttcggagc gcacacacac acaaccagat ctcccccaaa tccacccgtc | 1200 |
| ggcacctccg cttcaaggta cgccgctcgt cctccccccc cccccctctc taccttctct | 1260 |
| agatcggcgt tccggtccat agttagggcc cggtagttct acttctgttc atgtttgtgt | 1320 |
| tagatccgtg tttgtgttag atccgtgctg ttagcgttcg tacacggatg cgacctgtac | 1380 |
| gtcagacacg ttctgattgc taacttgcca gtgtttctct ttggggaatc ctgggatggc | 1440 |
| tctagccgtt ccgcagacgg gatcgatttc atgatttttt ttgtttcgtt gcatagggtt | 1500 |
| tggtttgccc ttttccttta tttcaatata tgccgtgcac ttgtttgtcg ggtcatcttt | 1560 |
| tcatgctttt ttttgtcttg gttgtgatga tgtggtctgg ttgggcggtc gttctagatc | 1620 |
| ggagtagaat tctgtttcaa actacctggt ggatttatta attttggatc tgtatgtgtg | 1680 |
| tgccatacat attcatagtt acgaattgaa gatgatggat ggaaatatcg atctaggata | 1740 |
| ggtatacatg ttgatgcggg ttttactgat gcatatacag agatgctttt tgttcgcttg | 1800 |
| gttgtgatga tgtggtgtgg ttgggcggtc gttcattcgt tctagatcgg agtagaatac | 1860 |
| tgttcaaac tacctggtgt atttattaat tttggaactg tatgtgtgtg tcatacatct | 1920 |
| tcatagttac gagtttaaga tggatggaaa tatcgatcta ggataggtat acatgttgat | 1980 |
| gtgggttta ctgatgcata tacatgatgg catatgcagc atctattcat atgctctaac | 2040 |

```
cttgagtacc tatctattat aataaacaag tatgttttat aattattttg atcttgatat    2100
acttggatga tggcatatgc agcagctata tgtggatttt tttagccctg ccttcatacg    2160
ctatttattt gcttggtact gttttcttttg tcgatgctca ccctgttgtt tggtgttact    2220
tctgcaggga tccaacctgg aacaggtcca caaaatcaag acaaaattac gttagaaagc    2280
cggttagcaa cattccaggg ttggccaaag agcattaaac agaggccttc tgagttagct    2340
gaggcgggat tttattacac aggagctggg gaccaaactg tgtgctttta ttgtggtggg    2400
ggattaaaag actgggatga aggagatgat ccttgggagc aacatgccct ttggtttagc    2460
aaatgtgtgt ttctcaattt gaaaaagggc aagaattca tcgatcaagt aaagaggaag     2520
gctgatccac aattttcaat tcctggacct agcggtactc aagccaaaga ggaaccgact    2580
gctactgaat cttcaagtga taaacaaagt gaaacagtga aaacaaaatc agatagggaa    2640
agtttcgcaa ctgacacaac tttgtgcaaa atttgcttta aaaacgaact tggtgttgtt    2700
ttcttgcctt gtggacatat tgttgcttgt gtaggtacca agctgcgaat cttcgttttt    2760
ttaaggaatt ctcgatcttt atggtgtata ggctctgggt tttctgtttt ttgtatctct    2820
taggattttg taaattccag atctttctat ggccacttag tagtatattt caaaaattct    2880
ccaatcgagt tcttcattcg cattttcagt cattttctct tcgacgttgt ttttaagcct    2940
gggtattact cctatttagt tgaactctgc agcaatctta gaaaattagg gttttgaggt    3000
ttcgatttct ctaggtaacc gatctattgc attcatctga atttctgcat atatgtctta    3060
gatttctgat aagcttacga tacgttaggt gtaattgaag tttatttttc aagagtgtta    3120 tttttttgttt ctgaattttt cagtcactcc atggcctagt acacaagcaa caatatgtcc    3180
acaaggcaag aaaacaacac caagttcgtt tttaaagcaa attttgcaca aagttgtgtc    3240
agttgcgaaa cttccctat ctgattttgt tttcactgtt tcactttgtt tatcacttga     3300
agattcagta gcagtcggtt cctctttggc ttgagtaccg ctaggtccag gaattgaaaa    3360
ttgtggatca gccttcctct ttacttgatc gatgaattct ttgccctttt tcaaattgag    3420
aaacacacat ttgctaaacc aaagggcatg ttgctcccaa ggatcatctc cttcatccca    3480 gtctttaat ccccaccac aataaaagca cacagtttgg tccccagctc ctgtgtaata     3540
aaatcccgcc tcagctaact cagaaggcct ctgtttaatg ctctttggcc aaccctggaa    3600
tgttgctaac cggcttttcta acgtaattttt gtcttgattt tgtggacctg ttccaggttg    3660
agctcgccat cagtcgttga agctgctgct gtatctgggt tatctagtgt ctctgccatt    3720
gcccaaggat ggtgctgtct ttcaaagtat ttgtatggtt tgtgtcgtga gtcgtgactg    3780
agctggtttc atggaccagt tgtgttctcg ttacccaaaa ctatcgtgcg accgcatatg    3840
gcttaatcat gaataaatgt tgtttgaatt taaactattc gctgaatatt gttgtttttt    3900
gtcatgtcag ttaatgttac taaattggtt gccttctaat ttttgtttac tggtgttttgt   3960 cgcaccttat ctttttactg tatgtttact tcaggttctg gcagtctcat tttttgtgac    4020
tagttaaaac ttacagctaa aaaaatgcag ttttcatttt tcatttgaag tttgattaga    4080
gctattgata cccggaccat caggttaggt tagttgtgca tagaatcata aatattaatc    4140
atgttttcta tgaattaagt caaacttgaa agtctggctg aatatagttt ctatgaatca    4200
tattgatata catgtttgat tatttgtttt gctattagct atttactttg gtgaatctat    4260
ataggcttat gcagaacctt ttttttttgtt ctatatatcc atatcctagt actcagtagc    4320
tctatgtttt ctggagacta gtggcttgct ttttcgtatg tctaatttttt tgcttgacca   4380
```

```
ttgcaaaaca aaaattacct agtgtaatct cttttttataa taatcttgta atgcgtctac  4440
ctataggtca aagtaggttt tgtttggaac ccttagagct aactgttagc tagttgataa  4500
attattagct gagttaagct agctaatgaa ctagttttga tattagctga ggatgtttga  4560
aacctaataa ttattttta ttagctaact atactaaatt ttagtagaga gattccaaac  4620
aggagttaac atgggatcag attggctatg cgtttgcaat cccatacgga cccggcgcgc  4680
catttaaatg gtaccggacc gcgatcgctt aattaagctt gcatgcctgc agtgcagcgt  4740
gacccggtcg tgcccctctc tagagataat gagcattgca tgtctaagtt ataaaaaatt  4800
accacatatt tttttgtca cacttgtttg aagtgcagtt tatctatctt tatacatata  4860
tttaaacttt actctacgaa taatataatc tatagtacta caataatatc agtgttttag  4920
agaatcatat aaatgaacag ttagacatgg tctaaaggac aattgagtat tttgacaaca  4980
ggactctaca gttttatctt tttagtgtgc atgtgttctc cttttttttt gcaaatagct  5040
tcacctatat aatacttcat ccattttatt agtacatcca tttaggggttt agggttaatg  5100
gtttttatag actaattttt ttagtacatc tatttattc tattttagcc tctaaattaa  5160
gaaaactaaa actctatttt agttttttta tttaataatt tagatataaa atagaataaa  5220
ataaagtgac taaaaattaa acaaataccc tttaagaaat taaaaaaact aaggaaacat  5280
ttttcttgtt tcgagtagat aatgccagcc tgttaaacgc cgccgacgag tctaacggac  5340
accaaccagc gaaccagcag cgtcgcgtcg ggccaagcga agcagacggc acggcatctc  5400
tgtcgctgcc tctggacccc tctcgagagt tccgctccac cgttggactt gctccgctgt  5460
cggcatccag aaattgcgtg gcggagcggc agacgtgagc cggcacggca ggcggcctcc  5520
tcctcctctc acggcaccgg cagctacggg ggattccttt cccaccgctc cttcgctttc  5580
ccttcctcgc ccgccgtaat aaatagacac cccctccaca ccctctttcc ccaacctcgt  5640
gttgttcgga gcgcacacac acacaaccag atctccccca aatccacccg tcggcacctc  5700
cgcttcaagg tacgccgctc gtcctccccc cccccccctc tctaccttct ctagatcggc  5760
gttccggtcc atagttaggg cccggtagtt ctacttctgt tcatgtttgt gttagatccg  5820
tgtttgtgtt agatccgtgc tgttagcgtt cgtacacgga tgcgacctgt acgtcagaca  5880
cgttctgatt gctaacttgc cagtgtttct ctttgggaa tcctgggatg gctctagccg  5940
ttccgcagac gggatcgatt tcatgatttt ttttgtttcg ttgcataggg tttggtttgc  6000
ccttttcctt tatttcaata tatgccgtgc acttgtttgt cgggtcatct tttcatgctt  6060
ttttttgtct tggttgtgat gatgtggtct ggttgggcgg tcgttctaga tcggagtaga  6120
attctgtttc aaactacctg gtggatttat taattttgga tctgtatgtg tgtgccatac  6180
atattcatag ttacgaattg aagatgatgg atggaaatat cgatctagga taggtataca  6240
tgttgatgcg ggttttactg atgcatatac agagatgctt tttgttcgct tggttgtgat  6300
gatgtggtgt ggttgggcgg tcgttcattc gttctagatc ggagtagaat actgtttcaa  6360
actacctggt gtatttatta attttggaac tgtatgtgtg tgtcatacat cttcatagtt  6420
acgagtttaa gatggatgga aatatcgatc taggataggt atacatgttg atgtgggttt  6480
tactgatgca tatacatgat ggcatatgca gcatcattc atatgctcta accttgagta  6540
cctatctatt ataataaaca agtatgtttt ataattattt tgatcttgat atacttggat  6600
gatggcatat gcagcagcta tatgtggatt ttttagccc tgccttcata cgctatttat  6660
ttgcttggta ctgtttcttt tgtcgatgct caccctgttg tttggtgtta cttctgcagg  6720
gatctccgat catgcaaaaa ctcattaact cagtgcaaaa ctatgcctgg ggcagcaaaa  6780
```

```
cggcgttgac tgaactttat ggtatggaaa atccgtccag ccagccgatg gccgagctgt   6840
ggatgggcgc acatccgaaa agcagttcac gagtgcagaa tgccgccgga gatatcgttt   6900
cactgcgtga tgtgattgag agtgataaat cgactctgct cggagaggcc gttgccaaac   6960
gctttggcga actgcctttc ctgttcaaag tattatgcgc agcacagcca ctctccattc   7020
aggttcatcc aaacaaacac aattctgaaa tcggttttgc caaagaaaat gccgcaggta   7080
tcccgatgga tgccgccgag cgtaactata aagatcctaa ccacaagccg agctggtttt   7140
ttgcgctgac gccttttcct tgcgatgaacg cgtttcgtga attttccgag attgtctccc   7200
tactccagcc ggtcgcaggt gcacatccgg cgattgctca cttttttacaa cagcctgatg   7260 ccgaacgttt aagcgaactg ttcgccagcc tgttgaatat gcagggtgaa gaaaaatccc   7320
gcgcgctggc gattttaaaa tcggccctcg atagccagca gggtgaaccg tggcaaacga   7380
ttcgtttaat ttctgaattt tacccggaag acagcggtct gttctccccg ctattgctga   7440
atgtggtgaa attgaaccct ggcgaagcga tgttcctgtt cgctgaaaca ccgcacgctt   7500
acctgcaagg cgtggcgctg gaagtgatgg caaactccga taacgtgctg cgtgcgggtc   7560
tgacgcctaa atacattgat attccggaac tggttgccaa tgtgaaattc gaagccaaac   7620
cggctaacca gttgttgacc cagccggtga acaaggtgc agaactggac ttcccgattc   7680
cagtggatga ttttgccttc tcgctgcatg accttagtga taaagaaacc accattagcc   7740
agcagagtgc cgccattttg ttctgcgtcg aaggcgatgc aacgttgtgg aaaggttctc   7800
agcagttaca gcttaaaccg ggtgaatcag cgtttattgc cgccaacgaa tcaccggtga   7860
ctgtcaaagg ccacggccgt ttagcgcgtg tttacaacaa gctgtaagag cttactgaaa   7920
aaattaacat ctcttgctaa gctgggtcat gggtcgttta agctgccgat gtgcctgcgt   7980
cgtctggtgc cctctctcca tatggaggtt gtcaaagtat ctgctgttcg tgtcatgagt   8040
cgtgtcagtg ttggtttaat aatggaccgg ttgtgttgtg tgtgcgtact acccagaact   8100
atgacaaatc atgaataagt ttgatgtttg aaattaaagc ctgtgctcat tatgttctgt   8160
ctttcagttg tctcctaata tttgcctcca ggtactggct atctaccgtt tcttacttag   8220
gaggtgtttg aatgcactaa aactaatagt tagtggctaa aattagttaa aacatccaaa   8280
caccatagct aatagttgaa ctattagcta ttttttggaaa attagttaat agtgaggtag   8340
ttatttgtta gctagctaat tcaactaaca attttttagcc aactaacaat tagttttcagt   8400 gcattcaaac acccccttaa tgttaacgtg gttctatcta ccgtctccta atatatggtt   8460
gattgttcgg tttgttgcta tgctattggg ttctgattgc tgctagttct tgctgaatcc   8520
agaagttctc gtagtatagc tcagattcat attatttatt tgagtgataa gtgatccagg   8580
ttattactat gttagctagg tttttttttac aaggataaat tatctgtgat cataattctt   8640
atgaaagctt tatgtttcct ggaggcagtg gcatgcaatg catgacagca acttgatcac   8700
accagctgag gtagatacgg taacaaggtt cttaaatctg ttcaccaaat cattggagaa   8760
cacacataca cattcttgcc agtcttggtt agagaaattt catgacaaaa tgccaaagct   8820
gtcttgactc ttcactttttg gccatgagtc gtgacttagt ttggtttaat ggaccggttc   8880
tcctagcttg ttctactcaa aactgttgtt gatgcgaata agttgtgatg gttgatctct   8940
ggattttgtt ttgctctcaa tagtggacga gattagatag cctgcaggcc cgggggcgcg   9000
ccctaattag ctaacggcca ggatcgccgc gtgagccttt agcaactagc tagattaatt   9060
aacgcaatct gttattaagt tgtctaagcg tcaatttgtt tacaccacaa tatatcctgc   9120
```

```
caccagccag ccaacagctc cccgaccggc agctcggcac aaaatcacca ctcgatacag   9180
gcagcccatc agaattaatt ctcatgtttg acagcttatc atcgactgca cggtgcacca   9240
atgcttctgg cgtcaggcag ccatcggaag ctgtggtatg gctgtgcagg tcgtaaatca   9300
ctgcataatt cgtgtcgctc aaggcgcact cccgttctgg ataatgtttt ttgcgccgac   9360
atcataacgg ttctggcaaa tattctgaaa tgagctgttg acaattaatc atccggctcg   9420
tataatgtgt ggaattgtga gcggataaca atttcacaca ggaaacagac catgagggaa   9480
gcgttgatcg ccgaagtatc gactcaacta tcagaggtag ttggcgtcat cgagcgccat   9540
ctcgaaccga cgttgctggc cgtacatttg tacggctccg cagtggatgg cggcctgaag   9600
ccacacagtg atattgattt gctggttacg gtgaccgtaa ggcttgatga acaacgcgg    9660 cgagctttga tcaacgacct tttggaaact tcggcttccc ctggagagag cgagattctc   9720
cgcgctgtag aagtcaccat tgttgtgcac gacgacatca ttccgtggcg ttatccagct   9780
aagcgcgaac tgcaatttgg agaatggcag cgcaatgaca ttcttgcagg tatcttcgag   9840
ccagccacga tcgacattga tctggctatc ttgctgacaa aagcaagaga acatagcgtt   9900
gccttggtag gtccagcggc ggaggaactc tttgatccgg ttcctgaaca ggatctattt   9960
gaggcgctaa atgaaacctt aacgctatgg aactcgccgc ccgactgggc tggcgatgag  10020
cgaaatgtag tgcttacgtt gtcccgcatt tggtacagcg cagtaaccgg caaaatcgcg  10080
ccgaaggatg tcgctgccga ctgggcaatg gagcgcctgc cggcccagta tcagcccgtc  10140
atacttgaag ctaggcaggc ttatcttgga caagaagatc gcttggcctc gcgcgcagat  10200
cagttggaag aatttgttca ctacgtgaaa ggcgagatca ccaaagtagt cggcaaataa  10260
agctctagtg gatctccgta cccagggatc tggctcgcgg cggacgcacg acgccggggc  10320
gagaccatag gcgatctcct aaatcaatag tagctgtaac ctcgaagcgt ttcacttgta  10380
acaacgattg agaatttttg tcataaaatt gaaatacttg gttcgcattt ttgtcatccg  10440
cggtcagccg caattctgac gaactgccca tttagctgga gatgattgta catccttcac  10500
gtgaaaattt ctcaagcgct gtgaacaagg gttcagattt tagattgaaa ggtgagccgt  10560
tgaaacacgt tcttcttgtc gatgacgacg tcgctatgcg gcatcttatt attgaatacc  10620
ttacgatcca cgccttcaaa gtgaccgcgg tagccgacag cacccagttc acaagagtac  10680
tctcttccgc gacggtcgat gtcgtggttg ttgatctaga tttaggtcgt gaagatgggc  10740
tcgagatcgt tcgtaatctg gcggcaaagt ctgatattcc aatcataatt atcagtggcg  10800
accgccttga ggagacggat aaagttgttg cactcgagct aggagcaagt gattttatcg  10860
ctaagccgtt cagtatcaga gagtttctag cacgcattcg ggttgccttg cgcgtgcgcc  10920
ccaacgttgt ccgctccaaa gaccgacggt cttttttgttt tactgactgg acacttaatc  10980
tcaggcaacg tcgcttgatg tccgaagctg gcggtgaggt gaaacttacg gcaggtgagt  11040
tcaatcttct cctcgcgttt ttagagaaac cccgcgacgt tctatcgcgc gagcaacttc  11100
tcattgccag tcgagtacgc gacgaggagg tttatgacag gagtatagat gttctcattt  11160
tgaggctgcg ccgcaaactt gaggcagatc cgtcaagccc tcaactgata aaaacagcaa  11220
gaggtgccgg ttatttcttt gacgcggacg tgcaggtttc gcacgggggg acgatggcag  11280
cctgagccaa ttcccagatc cccgaggaat cggcgtgagc ggtcgcaaac catccggccc  11340
ggtacaaatc ggcgcggcgc tgggtgatga cctggtggag aagttgaagg ccgcgcaggc  11400
cgcccagcgg caacgcatcg aggcagaagc acgccccgt gaatcgtggc aagcggccgc  11460
tgatcgaatc cgcaaagaat cccggcaacc gccggcagcc ggtgcgccgt cgattaggaa  11520
```

```
gccgcccaag ggcgacgagc aaccagattt tttcgttccg atgctctatg acgtgggcac    11580
ccgcgatagt cgcagcatca tggacgtggc cgttttccgt ctgtcgaagc gtgaccgacg    11640
agctggcgag gtgatccgct acgagcttcc agacgggcac gtagaggttt ccgcagggcc    11700
ggccggcatg ccagtgtgt gggattacga cctggtactg atggcggttt cccatctaac    11760
cgaatccatg aaccgatacc gggaagggaa gggagacaag cccggccgcg tgttccgtcc    11820
acacgttgcg gacgtactca agttctgccg gcgagccgat ggcggaaagc agaaagacga    11880
cctggtagaa acctgcattc ggttaaacac cacgcacgtt gccatgcagc gtacgaagaa    11940
ggccaagaac ggccgcctgg tgacggtatc cgagggtgaa gccttgatta gccgctacaa    12000
gatcgtaaag agcgaaaccg ggcggccgga gtacatcgag atcgagctgg ctgattggat    12060
gtaccgcgag atcacagaag gcaagaaccc ggacgtgctg acggttcacc ccgattactt    12120
tttgatcgat cccggcatcg gccgttttct ctaccgcctg gcacgccgcg ccgcaggcaa    12180
ggcagaagcc agatggttgt tcaagacgat ctacgaacgc agtggcagcg ccggagagtt    12240
caagaagttc tgtttcaccg tgcgcaagct gatcgggtca aatgacctgc cggagtacga    12300
tttgaaggag gaggcggggc aggctggccc gatcctagtc atgcgctacc gcaacctgat    12360
cgagggcgaa gcatccgccg gttcctaatg tacggagcag atgctagggc aaattgccct    12420 agcagggga aaaggtcgaa aaggtctctt tcctgtggat agcacgtaca ttgggaaccc    12480
aaagccgtac attgggaacc ggaacccgta cattgggaac ccaaagccgt acattgggaa    12540
ccggtcacac atgtaagtga ctgatataaa agagaaaaaa ggcgattttt ccgcctaaaa    12600
ctctttaaaa cttattaaaa ctcttaaaac ccgcctggcc tgtgcataac tgtctggcca    12660
gcgcacagcc gaagagctgc aaaaagcgcc taccccttcgg tcgctgcgct ccctacgccc    12720
cgccgcttcg cgtcggccta tcgcggccgc tggccgctca aaaatggctg gcctacggcc    12780
aggcaatcta ccagggcgcg gacaagccgc gccgtcgcca ctcgaccgcc ggcgctgagg    12840
tctgcctcgt gaagaaggtg ttgctgactc ataccaggcc tgaatcgccc catcatccag    12900
ccagaaagtg agggagccac ggttgatgag agctttgttg taggtggacc agttggtgat    12960
tttgaacttt tgctttgcca cggaacggtc tgcgttgtcg ggaagatgcg tgatctgatc    13020
cttcaactca gcaaaagttc gatttattca acaaagccgc cgtcccgtca agtcagcgta    13080
atgctctgcc agtgttacaa ccaattaacc aattctgatt agaaaactc atcgagcatc    13140 aaatgaaact gcaatttatt catatcagga ttatcaatac catattttg aaaaagccgt    13200 ttctgtaatg aaggagaaaa ctcaccgagg cagttccata ggatggcaag atcctggtat    13260
cggtctgcga ttccgactcg tccaacatca atacaaccta ttaatttccc ctcgtcaaaa    13320
ataaggttat caagtgagaa atcaccatga gtgacgactg aatccggtga aatggcaaa    13380 agctctgcat taatgaatcg gccaacgcgc ggggagaggc ggtttgcgta ttgggcgctc    13440
ttccgcttcc tcgctcactg actcgctgcg ctcggtcgtt cggctgcggc gagcggtatc    13500
agctcactca aaggcggtaa tacggttatc cacagaatca ggggataacg caggaaagaa    13560
catgtgagca aaaggccagc aaaaggccag gaaccgtaaa aaggccgcgt tgctggcgtt    13620
tttccatagg ctccgccccc ctgacgagca tcacaaaaat cgacgctcaa gtcagaggtg    13680
gcgaaacccg acaggactat aaagatacca ggcgtttccc cctggaagct ccctcgtgcg    13740
ctctcctgtt ccgaccctgc cgcttaccgg atacctgtcc gcctttctcc cttcgggaag    13800
cgtggcgctt tctcatagct cacgctgtag gtatctcagt tcggtgtagg tcgttcgctc    13860
```

```
caagctgggc tgtgtgcacg aacccccgt  tcagcccgac cgctgcgcct tatccggtaa    13920
ctatcgtctt gagtccaacc cggtaagaca cgacttatcg ccactggcag cagccactgg    13980
taacaggatt agcagagcga ggtatgtagg cggtgctaca gagttcttga agtggtggcc    14040
taactacggc tacactagaa gaacagtatt tggtatctgc gctctgctga agccagttac    14100
cttcggaaaa agagttggta gctcttgatc cggcaaacaa accaccgctg gtagcggtgg    14160
tttttttgtt tgcaagcagc agattacgcg cagaaaaaaa ggatctcaag aagatcctt     14220 gatcttttct acggggtctg acgctcagtg gaacgaaaac tcacgttaag ggattttggt    14280
catgagatta tcaaaaagga tcttcaccta gatccttttg atccggaatt a             14331
```

BIOLOGICAL CONTROL OF COLEOPTERAN PESTS

RELATED APPLICATION INFORMATION

This application is a 371 of International Application No. PCT/US2013/046450, filed 19 Jun. 2013, which claims priority to U.S. Provisional Application No. 61/662,958, filed Jun. 22, 2012, the disclosures of which are incorporated by reference herein in their entireties.

STATEMENT REGARDING ELECTRONIC SUBMISSION OF A SEQUENCE LISTING

A Sequence Listing in ASCII test format, submitted under 37 C.F.R. 1.821, entitled "73414_ST25.txt", 111 kilobytes in size, generated on Dec. 10, 2014 and filed via EFS-Web is provided in lieu of a paper copy. This sequence listing is hereby incorporated by reference into the specification for its disclosure.

FIELD OF THE INVENTION

The invention relates generally to the control of pests that cause damage to crop plants by their feeding activities, and more particularly to the control of coleopteran pests by compositions comprising interfering RNA molecules. The invention further relates to the compositions and to methods of using such compositions comprising the interfering RNA molecules.

BACKGROUND

Insect species in the genus *Diabrotica* (corn rootworms and cucumber beetles) are considered some of the most important pests to crop plants. For example, species of corn rootworm, including *Diabrotica virgifera virgifera*, the western corn rootworm (WCR); *D. barberi*, the northern corn rootworm (NCR), *D. undecimpunctata howardi*, the southern corn rootworm (SCR), and *D. virgifera zeae*, the Mexican corn rootworm (MCR), are the most destructive corn pests in North America causing an estimated loss of over $1 billion annually. The western corn rootworm has also invaded Europe and causes an estimated 0.5 billion euros in damage each year. *Diabrotica speciosa* (common names include, among others, leaf beetle, little Brazilian beetle, cucurbit beetle and *chrysanthemum* beetle) is an important pest of corn, soybean and peanuts, in South America.

Most of the damage in corn is caused by larval rootworm feeding. Newly hatched rootworm larvae locate corn roots in the soil and initially begin feeding on the fine root hairs and burrow into root tips of the corn plant. As larvae grow larger, they feed on and tunnel into primary roots. When rootworms are abundant, larval feeding and deterioration of injured roots by root rot pathogens can result in roots being pruned to the base of the stalk. Severe root injury interferes with the roots' ability to transport water and nutrients into the plant, reduces plant growth, and results in reduced grain production. Severe root injury also may result in lodging of corn plants, making mechanical harvest more difficult or impossible. Corn rootworm adults feed primarily on corn silk, pollen, and kernels on exposed ear tips. If corn rootworm adults begin emerging before corn reproductive tissues are present, adults may feed on leaf tissue, scraping away the green surface tissue and leaving a window-pane appearance. Silk feeding by adults can result in pruning of silks at the ear tip, commonly called silk clipping. In field corn, beetle populations may reach a level high enough to cause severe silk clipping during pollen shed, which may interfere with pollination and reduce yield. Thus, unlike lepidopteran pests of corn in which only the larval stages cause damage, both the larval and adult stages of corn rootworm are capable of causing economic damage to corn.

*Diabrotica* insect pests are mainly controlled by intensive applications of chemical pesticides, which may be active against both larval and adult stages, through inhibition of insect growth, prevention of insect feeding or reproduction, or cause death. Good insect control can thus be reached, but these chemicals can sometimes also affect other, beneficial insects. Additional problems occur in areas of high insecticide use where populations of corn rootworm beetles have become resistant to certain insecticides. This has been partially alleviated by various resistance management practices, but there is an increasing need for alternative pest control agents.

Several native Cry proteins from *Bacillus thuringiensis*, or engineered Cry proteins, have been expressed in transgenic crop plants and exploited commercially to control certain lepidopteran and coleopteran insect pests. For example, starting in 2003, transgenic corn hybrids that control corn rootworm by expressing a Cry3Bb1, Cry34Ab1/Cry35Ab1 or modified Cry3A (mCry3A) protein have been available commercially in the US.

The seed industry, university researchers and the US Environmental Protection Agency have worked together to develop management plans to help mitigate the onset of insect resistance to transgenic plants expressing insecticidal proteins. They are based primarily on a high dose and refuge strategy. A high dose strategy is to use corn hybrids that express high enough levels of an insecticidal protein such as a Cry protein to kill even partially resistant insects. The underlying hypothesis is that killing partially resistant insects and preventing their mating greatly delays the development of resistance. The success of a high dose strategy depends in part on the specific activity of the insecticidal protein to the particular insect species and how much of that insecticidal protein can be expressed in the transgenic corn plant. The higher the specific activity of an insecticidal protein to a pest, the less amount of the insecticidal protein is required to be expressed in a transgenic plant to achieve a high dose strategy. For example, corn hybrids expressing the lepidopteran-active Cry protein, Cry1Ab, are considered high-dose against the primary target pest European corn borer (*Ostrinia nubilalis*). Because Cry1Ab is very toxic to European corn borer larvae with an LC50<10 ng/cm$^2$ (i.e. high specific activity), levels of expression of Cry1Ab that are achievable in transgenic plants easily places such corn hybrids in a high dose category. However, unlike the lepidopteran-active products, current rootworm products are not considered high-dose. The proteins they express are not active against adults and have limited activity against late instar larvae. Therefore, the current transgenic rootworm products allow some rootworm larvae to survive and emerge as adults.

Thus, economic levels of silk clipping by corn rootworm adults may still occur even in portions of fields planted to a transgenic corn rootworm hybrid. For example, densities of western corn rootworm adults may exceed economic levels in portions of fields planted to transgenic corn rootworm hybrids due to immigration of beetles as well as direct emergence of adults from transgenic root systems. There have been many reports that confirm western corn rootworm adult emergence from certain corn transgenic rootworm hybrids (Crowder et al. 2005. J. Econ. Entomol. 8:961-975). A recent publication suggests that western corn rootworm adults will exhibit similar feeding behaviors when encountering some transgenic corn plants or non-transgenic corn plants in the field and that it is unlikely that certain insecticidal proteins in transgenic plants will have significant effects on adults that might impact resistance management.

Therefore, indentifying alternative insect control agents with new modes of action would be beneficial. Particularly useful would be new insect control agents that are toxic to multiple life stages of the target insect pest. Such insect control agents may include those that target genetic elements in the target insect pest.

Apoptosis is a physiological cell death process that is critical for the development and maintenance of healthy biological systems in many living organisms. The Inhibitor of Apoptosis (IAP) family of proteins was first discovered in baculoviruses that attack insects and have been shown to be involved in suppressing the insect host cell death (apoptosis) response to baculovirus infection (Crook et al. 1993. J. Virol. 67:2168-2174; Birnbaum et al. 1994. J. Virol. 68:2521-2528). Subsequently, IAP proteins were discovered in other organisms including the yeast *Saccharomyces cerevisiae*, the nematode *Caenorhabditis elegans*, the fly *Drosophila melanogaster*, and several mammalian species. Native IAP acts as an endogenous inhibitor of caspases, the main executioners of apoptosis and IAP family proteins are characterized by an approximately 70 amino acid domain termed the baculoviral IAP repeat (BIR). Up to three tandem copies of the BIR domain can occur within the known IAP family proteins of viruses and animal species. Although membership in the IAP family of proteins requires both the presence of a BIR domain and the ability to suppress apoptosis, many of these BIR-containing proteins are untested with respect to apoptosis suppression. Moreover, as it is debatable as to whether yeast possess an apoptosis program (Zha et al. 1996. Mol Cell Biol. 16:6494-6508), because the presence of BIR-containing proteins in *S. pombe* and *S. cerevisiae* raises the possibility that BIR domains are not devoted exclusively to apoptosis suppression. Rather, they may function as protein interaction domains that may have evolved to suit a variety of purposes.

Therefore, it is not clear that all IAPs are part of life-critical pathways for any given organism, particularly in certain insect species including coleopteran pest species like *Diabrotica* spp. It is also uncertain that IAP proteins in a pest *Diabrotica* species can be targeted as a pest control strategy. Furthermore, it is even more uncertain that the expression of such IAP proteins can be modulated using interfering RNA molecules and that if such protein expression can be modulated, whether such modulation will result in toxicity to the target *Diabrotica* pest.

RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Most plant miRNAs show extensive base pairing to, and guide cleavage of their target mRNAs (Jones-Rhoades et al. (2006) *Annu. Rev. Plant Biol.* 57, 19-53; Llave et al. (2002) *Proc. Natl. Acad. Sci. USA* 97, 13401-13406). In other instances, interfering RNAs may bind to target RNA molecules having imperfect complementarity, causing translational repression without mRNA degradation. The majority of the animal miRNAs studied so far appear to function in this manner.

There is an ongoing need for compositions and methods for using such compositions having insecticidal activity, for instance for use in crop protection or insect-mediated disease control. Novel compositions are required to overcome the problem of resistance to existing insecticides and/or to help mitigate the development of resistance to existing transgenic plant approaches. Ideally such compositions have a high toxicity and are effective when ingested orally by the target pest and have applicability for use against both the larval and adult stages of the pest insect. Thus any invention which provided compositions in which any of these properties was enhanced would represent a step forward in the art.

SUMMARY

The needs outlined above are met by the invention which, in various embodiments, provides new methods of controlling economically important insect pests. The invention in part comprises a method of inhibiting expression of one or more target genes and proteins in insect pests such as members of the genus *Diabrotica*. Specifically, the invention comprises methods of modulating expression of one or more inhibitor of apoptosis (IAP) genes in *Diabrotica* species such as *Diabrotica virgifera virgifera* (western corn rootworm), *Diabrotica barberi* (northern corn rootworm), *Diabrotica undecimpunctata howardi* (southern corn rootworm), *Diabrotica virgifera zeae* (Mexican corn rootworm), *Diabrotica speciosa* (*chrysanthemum* beetle), and related species, that causes cessation of feeding, growth, development and reproduction, and eventually results in the death of the insect. The method comprises introduction of double-stranded RNA (dsRNA) or its modified forms such as small interfering RNA (siRNA) sequences, into cells or into the extracellular environment, such as the midgut, within a pest insect body wherein the dsRNA or siRNA enters the cells and inhibits expression of at least one or more IAP genes and wherein inhibition of the one or more IAP genes exerts a deleterious effect upon the pest insect. It is specifically contemplated that the methods and compositions of the invention will be useful in limiting or eliminating pest insect infestation in or on any plant by providing one or more compositions comprising dsRNA or siRNA molecules in the diet of the pest. The invention also provides interfering RNA molecules that when delivered to an insect pest inhibits, through a toxic effect, the ability of the insect pest to survive, grow, feed and/or reproduce, or to limit pest related damage or loss to crop plants. Such delivery may be through production of the interfering RNA in a transgenic plant, for example corn, or by topically applying a composition comprising the interfering RNA to a plant or plant seed, such as a corn plant or corn seed. The interfering RNA molecule comprises a nucleotide sequence that is complementary to a nucleotide sequence of a mRNA transcribable from a IAP gene or a portion of a nucleotide sequence of a mRNA transcribable from a IAP gene of the pest insect and therefore inhibits expression of the IAP gene, which causes cessation of feeding, growth, development, reproduction and eventually results in death of the pest insect. The invention is further drawn to nucleic acid constructs, nucleic acid molecules and recombinant vectors that comprise at least one strand of a dsRNA molecule of the invention. The invention also provides chimeric nucleic acid molecules comprising an antisense strand of a dsRNA of the invention operably associated with a plant microRNA precursor molecule. The invention also provides artificial plant microRNA precursors comprising an antisense strand of a dsRNA of the invention.

The invention further provides compositions comprising two or more of the dsRNA molecules of the invention wherein the two or more RNA molecules each comprise a different antisense strand, or comprising two or more nucleic acid constructs or nucleic acid molecules or artificial plant microRNA precursors of the invention.

The invention further provides insecticidal compositions for inhibiting the expression of a *Diabrotica* insect IAP gene that comprises a dsRNA of the invention and an agriculturally acceptable carrier. Inhibition of the expression of the *Diabrotica* IAP gene leads to cessation of feeding and growth and ultimately results in the death of the *Diabrotica* insect.

The invention is further drawn to transgenic plants which produce one or more interfering RNA molecules of the invention that are self-protected from insect feeding damage and to methods of using the plants alone or in combination with other insect control strategies to confer maximal insect control capabilities. Plants and/or plant parts producing one or more interfering RNA molecules of the invention or treated with a composition comprising one or more interfering RNA molecules of the invention are highly resistant to insect pest infestation. For example, economically important coleopteran pests in the genus *Diabrotica* can be controlled by a plant that produces an interfering RNA molecule of the invention or by a plant or plant seed that is treated with a composition comprising an interfering RNA molecule of the invention.

The invention also provides a method of controlling a *Diabrotica* insect comprising contacting the *Diabrotica* insect with a nucleic acid molecule that is or is capable of producing an interfering RNA of the invention for inhibiting expression of an IAP gene in the *Diabrotica* insect thereby controlling the *Diabrotica* insect.

In other aspects, the invention provides a method of reducing an adult *Diabrotica* insect population on a transgenic plant expressing a Cry protein, a hybrid Cry protein or modified Cry protein comprising expressing in the transgenic plant a nucleic acid molecule that is or is capable of producing an interfering RNA of the invention capable of inhibiting expression of an IAP gene in an adult *Diabrotica* insect thereby reducing the adult *Diabrotica* insect population.

In other aspects, the invention provides a method of reducing resistance development in a *Diabrotica* insect population to an interfering RNA of the invention, the method comprising expressing in a transgenic plant fed upon by the *Diabrotica* insect population an interfering RNA of the invention that is capable of inhibiting expression of an IAP gene in a larval and adult *Diabrotica* insect, thereby reducing resistance development in the *Diabrotica* insect population compared to a *Diabrotica* insect population exposed to an interfering RNA capable of inhibiting expression of an IAP gene in only the larval stage or adult stage of a *Diabrotica* insect.

In other aspects, the invention provides a method of reducing the level of a target RNA transcribable from a IAP gene in a *Diabrotica* insect comprising contacting the *Diabrotica* insect with a composition comprising a dsRNA molecule of the invention, wherein the dsRNA molecule reduces the level of the target RNA in a cell of the *Diabrotica* insect.

In still other aspects, the invention provides a method of conferring *Diabrotica* insect tolerance to a plant, or part thereof, comprising introducing into the plant, or part thereof, a dsRNA molecule, a nucleic acid construct, a chimeric nucleic acid molecule, an artificial plant microRNA precursor molecule and/or a composition of the invention, thereby conferring tolerance of the plant or part thereof to the *Diabrotica* insect.

In further aspects, the invention provides a method of reducing root damage to a plant fed upon by a *Diabrotica* insect, comprising introducing into cells of the plant a dsRNA, a nucleic acid molecule, a nucleic acid construct, a chimeric nucleic acid molecule, an artificial plant microRNA precursor molecule and/or a composition of the invention, thereby reducing root damage to the plant.

In other aspects, the invention provides a method of producing a transgenic plant cell having toxicity to a *Diabrotica* insect, comprising introducing into a plant cell a dsRNA, a nucleic acid molecule, a nucleic acid construct, a chimeric nucleic acid molecule, an artificial plant microRNA precursor molecule and/or a composition of the invention, thereby producing the transgenic plant cell having toxicity to the *Diabrotica* insect compared to a control plant cell.

In further aspects, the invention provides a method of producing a transgenic plant having enhanced tolerance to *Diabrotica* insect feeding damage, comprising introducing into a plant a dsRNA, a nucleic acid molecule, a nucleic acid construct, a chimeric nucleic acid molecule, an artificial plant microRNA precursor molecule and/or a composition of the invention, thereby producing a transgenic plant having enhanced tolerance to *Diabrotica* insect feeding damage compared to a control plant.

In other aspects, the invention provides a method of enhancing control of a *Diabrotica* insect population comprising providing a transgenic plant or transgenic seed of the invention and applying to the transgenic plant or the transgenic seed a chemical pesticide that is insecticidal to a *Diabrotica* insect, thereby enhancing control of the *Diabrotica* insect population.

In other aspects, the invention provides a method of providing a corn grower with a means of controlling a *Diabrotica* insect pest population in a corn crop comprising (a) selling or providing to the grower at least one bag of corn seed comprising transgenic corn seed that comprises a dsRNA, a nucleic acid molecule, a nucleic acid construct, a chimeric nucleic acid molecule, an artificial plant microRNA precursor molecule and/or a composition of the invention; and (b) advertising to the grower that the transgenic corn seed produces transgenic corn plants capable of controlling a *Diabrotica* insect pest.

These and other aspects of the invention are set forth in more detail in the description of the invention below.

BRIEF DESCRIPTION OF THE DRAWINGS

FIG. 4 is an alignment of *Diabrotica* IAP coding sequences. A "." below a base (A, T, G or C) indicates an identical base as in the reference sequence. Bases that are different from the reference sequence are indicated.

BRIEF DESCRIPTION OF THE SEQUENCES IN THE SEQUENCE LISTING

Figure 1:
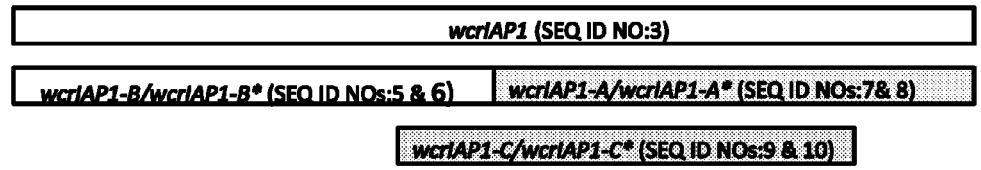
FIG. 1 shows portions of the wcrIAP1 mRNA targeted by the wcrIAP1-A, wcrIAP1-B and wcrIAP1-C dsRNA.

SEQ ID NO:1 is a nucleotide sequence of a western corn rootworm IAP1 cDNA (wcrIAP1) including the 5' and 3' untranslated regions (UTR5).
SEQ ID NO:2 is a nucleotide sequence of the coding region of wcrIAP1 (SEQ ID NO:1).
SEQ ID NO:3 is a nucleotide sequence of a mRNA transcribable from the wcrIAP1 gene.
SEQ ID NO:4 is an antisense sequence of the wcrIAP1 mRNA designated wcrIAP1*.
SEQ ID NO:5 is a sense strand of a dsRNA designated wcrIAP1-B.
SEQ ID NO:6 is an antisense strand of wcrIAP1-8 designated wcrIAP1-8*.
SEQ ID NO:7 is a sense strand of a dsRNA designated wcrIAP1-A.
SEQ ID NO:8 is an antisense strand of wcrIAP1-A designated wcrIAP1-A*.
SEQ ID NO:9 is a sense strand of a dsRNA designated wcrIAP1-C.
SEQ ID NO:10 is an antisense strand of wcrIAP1-C designated wcrIAP1-C*.
SEQ ID NO:11 is a nucleotide sequence from a western corn rootworm IAP2 coding region (wcrIAP2).
SEQ ID NO:12 is a nucleotide sequence of a mRNA transcribable from wcrIAP2.
SEQ ID NO:13 is an antisense sequence of the wcrIAP2 mRNA designated wcrIAP2*.
SEQ ID NO:14 is a nucleotide sequence of a southern corn rootworm IAP1 coding region (scrIAP1).
SEQ ID NO:15 is a nucleotide sequence of a mRNA transcribable from scrIAP1 (SEQ ID NO:14).
SEQ ID NO:16 is an antisense sequence of the scrIAP1 mRNA designated scrIAP1*.
SEQ ID NO:17 is a nucleotide sequence of a northern corn rootworm IAP1 coding region (ncrIAP1)
SEQ ID NO:18 is a nucleotide sequence of a mRNA transcribable from ncrIAP1.
SEQ ID NO:19 is an antisense sequence of the ncrIAP1 mRNA designated ncrIAP1*.
SEQ ID NO:20 is the amino acid sequence encoded by SEQ ID NO:2.
SEQ ID NO:21 is the amino acid sequence encoded by SEQ ID NO:11.
SEQ ID NO:22 is the amino acid sequence encoded by SEQ ID NO:14.
SEQ ID NO:23 is the amino acid sequence encoded by SEQ ID NO:17.
SEQ ID NO:24 is an amino acid sequence of a *Drosophila melanogaster* IAP protein (dmIAP).

SEQ ID NOs:25-28 are examples of 19-mer portions of wcrIAP1 mRNA (SEQ ID NO:3) targetable by siRNA.
SEQ ID NOs:29-32 are examples of 19-mer portions of wcrIAP2 mRNA (SEQ ID NO:12) targetable by siRNA.
SEQ ID NOs:33-36 are examples of 19-mer portions of scrIAP1 mRNA (SEQ ID NO:15) targetable by siRNA.
SEQ ID NOs:37-40 are examples of 19-mer portions of ncrIAP1 mRNA (SEQ ID NO:18) targetable by siRNA.
SEQ ID NOs:41-44 are examples of wcrIAP1* anti-sense 19-mer sequences.
SEQ ID NOs:45-48 are examples of wcrIAP2* anti-sense 19-mer sequences.
SEQ ID NOs:49-52 are examples of scrIAP1* anti-sense 19-mer sequences.
SEQ ID NOs:53-56 are examples of ncrIAP1* anti-sense 19-mer sequences.
SEQ ID NOs:57-62 are primers useful in the invention.
SEQ ID NO:63 is a nucleotide sequence coding for a hairpin RNA (hpRNA) designated hpwcrIAP1-C/wcrIAP1-C*.
SEQ ID NO:64 is a nucleotide sequence coding for a hairpin RNA (hpRNA) designated hpwcrIAP1-Ca/wcrIAP1-Ca*.
SEQ ID NO:65 is a nucleotide sequence of the pRNA21534 expression vector.
SEQ ID NO:66 is a nucleotide sequence of the pRNA21536 expression vector.
SEQ ID NO:67 is a nucleotide sequence of the pRNA21537 expression vector.

DETAILED DESCRIPTION

The following is a detailed description of the invention provided to aid those skilled in the art in practicing the invention. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments of the invention will be apparent to those skilled in the art in light of the instant disclosure, which do not depart from the invention. Hence, the following descriptions are intended to illustrate some particular embodiments of the invention, and not to exhaustively specify all permutations, combinations and variations thereof. Those of ordinary skill in the art may make modifications and variations in the embodiments described herein without departing from the spirit or scope of the invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

For clarity, certain terms used in the specification are defined and presented as follows:

As used herein, "a," "an" or "the" can mean one or more than one. For example, a cell can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, "dsRNA" or "RNAi" refers to a polyribonucleotide structure formed either by a single self-complementary RNA strand or at least by two complementary RNA strands. The degree of complementary, in other words the % identity, need not necessarily be 100%. Rather, it must be sufficient to allow the formation of a double-stranded structure under the conditions employed.

Preferably, the % identity of a polyribonucleotide is determined by GAP (Needleman and Wunsch, 1970) analysis (GCG program) using the default settings, wherein the query sequence is at least about 21 to about 23 nucleotides in length, and the GAP analysis aligns the two sequences over a region of at least about 21 nucleotides. In another embodiment, the query sequence is at least 150 nucleotides in length, and the GAP analysis aligns the two sequences over a region of at least 150 nucleotides. In a further embodiment, the query sequence is at least 300 nucleotides in length and the GAP analysis aligns the two sequences over a region of at least 300 nucleotides. In yet another embodiment, the query sequence corresponds to the full length of the target RNA, for example mRNA, and the GAP analysis aligns the two sequences over the full length of the target RNA.

Conveniently, the dsRNA can be produced from a single open reading frame in a recombinant host cell, wherein the sense and anti-sense sequences are flanked by an unrelated sequence which enables the sense and anti-sense sequences to hybridize to form the dsRNA molecule with the unrelated sequence forming a loop structure. Alternatively, the sense strand and antisense strand can be made without an open reading frame to ensure that no protein will be made in the transgenic host cell. The two strands can also be expressed separately as two transcripts, one encoding the sense strand and one encoding the antisense strand.

RNA duplex formation can be initiated either inside or outside the cell. The dsRNA can be partially or fully double-stranded. The RNA can be enzymatically or chemically synthesized, either in vitro or in vivo.

The dsRNA need not be full length relative to either the primary transcription product or fully processed RNA. Generally, higher identity can be used to compensate for the use of a shorter sequence. Furthermore, the dsRNA can comprise single stranded regions as well, e.g., the dsRNA can be partially or fully double stranded. The double stranded region of the dsRNA can have a length of at least about 18 to about 25 base pairs, optionally a sequence of about 18 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs, up to molecule that is double stranded for its full length, corresponding in size to a full length target RNA molecule.

The dsRNA can contain known nucleotide analogs or modified backbone residues or linkages, which are synthetic, naturally occurring, and non-naturally occurring. Examples of such analogs include, without limitation, phosphorothioates, phosphoramidates, methyl phosphonates, chiralmethyl phosphonates and 2-O-methyl ribonucleotides.

As used herein, the term "specifically reduce the level of a target RNA and/or the production of a target protein encoded by the RNA", and variations thereof, refers to the sequence of a portion of one strand of the dsRNA being sufficiently identical to the target RNA such that the presence of the dsRNA in a cell reduces the steady state level and/or the production of said RNA. In many instances, the target RNA will be mRNA, and the presence of the dsRNA in a cell producing the mRNA will result in a reduction in the production of said protein. Preferably, this accumulation or production is reduced at least 10%, more preferably at least 50%, even more preferably at least 75%, yet even more preferably at least 95% and most preferably 100%, when compared to a wild-type cell.

The consequences of inhibition can be confirmed by examination of the outward properties of the cell or organism or by biochemical techniques such as, but not limited to, Northern hybridization, reverse transcription, gene expression monitoring with a microarray, antibody binding, enzyme linked immunosorbent assay (ELISA), Western blotting, radioimmunoassay (RIA), and other immunoassays.

MicroRNAs (miRNAs) are non-protein coding RNAs, generally of between about 18 to about 25 nucleotides in length (commonly about 20-24 nucleotides in length in plants). These miRNAs direct cleavage in trans of target transcripts, negatively regulating the expression of genes involved in various regulation and development pathways (Bartel, *Cell,* 116:281-297 (2004); Zhang et al. *Dev. Biol.* 289:3-16 (2006)). As such, miRNAs have been shown to be involved in different aspects of plant growth and development as well as in signal transduction and protein degradation. In addition, small endogenous mRNAs including miR-NAs may also be involved in biotic stress responses such as pathogen attack. Since the first miRNAs were discovered in plants (Reinhart et al. *Genes Dev.* 16:1616-1626 (2002), Park et al. *Curr. Biol.* 12:1484-1495 (2002)) many hundreds have been identified. Furthermore, many plant miRNAs have been shown to be highly conserved across very divergent taxa. (Floyd et al. *Nature* 428:485-486 (2004); Zhang et al. *Plant J.* 46:243-259 (2006)). Many microRNA genes (MIR genes) have been identified and made publicly available in a database (miRBase; microrna.sanger.ac.uk/sequences). miRNAs are also described in U.S. Patent Publications 2005/0120415 and 2005/144669A1, the entire contents of which are incorporated by reference herein.

Genes encoding miRNAs yield primary miRNAs (termed a "pri-miRNA") of 70 to 300 bp in length that can form imperfect stem-loop structures. A single pri-miRNA may contain from one to several miRNA precursors. In animals, pri-miRNAs are processed in the nucleus into shorter hairpin RNAs of about 65 nt (pre-miRNAs) by the RNaseIII enzyme Drosha and its cofactor DGCR8/Pasha. The pre-miRNA is then exported to the cytoplasm, where it is further processed by another RNaseIII enzyme, Dicer, releasing a miRNA/miRNA* duplex of about 22 nt in size. In contrast to animals, in plants, the processing of pri-miRNAs into mature miRNAs occurs entirely in the nucleus using a single RNaseIII enzyme, DCL1 (Dicer-like 1). (Zhu. *Proc. Natl. Acad. Sci.* 105:9851-9852 (2008)). Many reviews on microRNA biogenesis and function are available, for example, see, Bartel *Cell* 116:281-297 (2004), Murchison et al. *Curr. Opin. Cell Biol.* 16:223-229 (2004), Dugas et al. *Curr. Opin. Plant Biol.* 7:512-520 (2004) and Kim Nature *Rev. Mol. Cell Biol.* 6:376-385 (2005).

The term "plant microRNA precursor molecule" as used herein describes a small (~70-300 nt) non-coding RNA sequence that is processed by plant enzymes to yield a ~19-24 nucleotide product known as a mature microRNA sequence. The mature sequences have regulatory roles through complementarity to messenger RNA. The term "artificial plant microRNA precursor molecule" describes the non-coding miRNA precursor sequence prior to processing that is employed as a backbone sequence for the delivery of a siRNA molecule via substitution of the endogenous native miRNA/miRNA* duplex of the miRNA precursor molecule with that or a non-native, heterologous miRNA (amiRNA/amiRNA*; e.g. siRNA/siRNA*) that is then processed into the mature miRNA sequence with the siRNA sequence.

In the context of the invention, the term "toxic" used to describe a dsRNA of the invention means that the dsRNA molecules of the invention and combinations of such dsRNA molecules function as orally active insect control agents that have a negative effect on an insect. When a composition of the invention is delivered to the insect, the result is typically death of the insect, or the insect does not feed upon the source that makes the composition available to the insect. Such a composition may be a transgenic plant expressing the dsRNA of the invention.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

The terms "complementary" or "complementarity," as used herein, refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, the terms "substantially complementary" or "partially complementary mean that two nucleic acid sequences are complementary at least about 50%, 60%, 70%, 80% or 90% of their nucleotides. In some embodiments, the two nucleic acid sequences can be complementary at least at 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art To "control" or "controlling" insects means to inhibit, through a toxic effect, the ability of one or more insect pests to survive, grow, feed, and/or reproduce, or to limit insect-related damage or loss in crop plants. To "control" insects may or may not mean killing the insects, although it preferably means killing the insects.

To "deliver" or "delivering" a composition or dsRNA means that the composition or dsRNA comes in contact with an insect, resulting in a toxic effect and control of the insect. The composition or dsRNA can be delivered in many recognized ways, e.g., orally by ingestion by the insect via transgenic plant expression, formulated composition(s), sprayable composition(s), a bait matrix, or any other art-recognized RNA delivery system.

"*Diabrotica*" is a genus of beetles commonly referred to as "corn rootworms" or "cucumber beetles." There are many species of *Diabrotica* that are pests of crop plants, including without limitation, *Diabrotica barberi* (northern corn rootworm; NCR), *D. virgifera virgifera* (western corn rootworm; WCR), *D. undecimpunctata howardii* (southern corn rootworm; SCR) and *D. virgifera zeae* (Mexican corn rootworm; MCR). In the context of the invention, the term "corn rootworm" or "cucumber beetle" is interchangeable with the term "*Diabrotica.*"

A "*Diabrotica* life stage" or "corn rootworm life stage" means the egg, larval, pupal or adult developmental form of a *Diabrotica* species.

"Effective insect-controlling amount" means that concentration of dsRNA that inhibits, through a toxic effect, the ability of insects to survive, grow, feed and/or reproduce, or to limit insect-related damage or loss in crop plants. "Effective insect-controlling amount" may or may not mean a concentration that kills the insects, although it preferably means that it kills the insects.

"Expression cassette" as used herein means a nucleic acid sequence capable of directing expression of a particular nucleic acid sequence in an appropriate host cell, comprising a promoter operably linked to the nucleic acid sequence of interest which is operably linked to termination signals. It also typically comprises sequences required for proper translation of the nucleic acid sequence. The expression cassette comprising the nucleic acid sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleic acid sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

As used herein, the term "grower" means a person or entity that is engaged in agriculture, raising living organisms, such as crop plants, for example corn, for food or raw materials.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Insecticidal" is defined as a toxic biological activity capable of controlling insects, preferably by killing them.

An "isolated" nucleic acid molecule or nucleotide sequence or nucleic acid construct or dsRNA molecule or protein of the invention is generally exists apart from its native environment and is therefore not a product of nature. An isolated nucleic acid molecule or nucleotide sequence or nucleic acid construct or dsRNA molecule or protein may exist in a purified form or may exist in a non-native environment such as, for example, a recombinant host cell such as a transgenic plant.

In the context of the invention, a number in front of the suffix "mer" indicates a specified number of subunits. When applied to RNA or DNA, this specifies the number of bases in the molecule. For example, a 19 nucleotide subsequence of an mRNA having the sequence ACUGGUCGCGUUG-CAUGCU is a "19-mer."

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A corn rootworm "transcriptome" is a collection of all the ribonucleic acid (RNA) transcripts in a corn rootworm cell.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The nomenclature used herein for DNA or RNA bases and amino acids is as set forth in 37 C.F.R. §1.822.

The invention is based on the unexpected discovery that double stranded RNA (dsRNA) or small interfering RNAs (siRNA) designed to target a mRNA transcribable from an IAP gene of a *Diabrotica* insect are toxic to the *Diabrotica* insect pest and can be used to control *Diabrotica* infestation of a plant and impart to a transgenic plant tolerance to a *Diabrotica* infestation. Thus, in some embodiments, the invention provides a double stranded RNA (dsRNA) molecule comprising a sense strand and an antisense strand, wherein a nucleotide sequence of the antisense strand is complementary to a portion of a mRNA polynucleotide transcribable from a *Diabrotica* IAP gene that comprises a IAP coding sequence having at least 90% identity, or at least 91% identity, or at least 92% identity, or at least 93% identity, or at least 94% identity, or at least 95% identity, or least 96% identity, or at least 97% identity, or at least 98% identity, or at least 99% identity to SEQ ID NO:2, and wherein the dsRNA molecule is toxic to a *Diabrotica* insect. In some embodiments the *Diabrotica* IAP gene is from a *Diabrotica* insect selected from the group consisting of *Diabrotica barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (*chrysanthemum* beetle), *D. virgifera zeae* (Mexican corn rootworm), *D. beniensis, D. cristata, D. curvipustulata, D. dissimilis, D. elegantula, D. emorsitans, D. graminea, D. hispanolae, D. lemniscata, D. linsleyi, D. milleri, D. nummularis, D. occlusa, D. porracea, D. scutellata, D. tibialis, D. trifasciata* and *D. viridula.* In further embodiments, the *Diabrotica* insect is *D. virgifera virgifera* (western corn rootworm), *D. undecimpunctata howardi* (southern corn rootworm) or *D. barberi* (northern corn rootworm). In some embodiments, the IAP coding sequence comprises SEQ ID NO:2, SEQ ID NO:11, SEQ ID NO:14 or SEQ ID NO:17.

In some embodiments, the dsRNA molecule can comprise, consist essentially of or consist of from at least 18 to about 25 consecutive nucleotides (e.g. 18, 19, 20, 21, 22, 23, 24 or 25) to at least about 400 consecutive nucleotides. In some embodiments the dsRNA molecule can comprise, consist essentially of or consist of about 500, or about 50 or about 543 consecutive nucleotides. Additional nucleotides can be added at the 3' end, the 5' end or both the 3' and 5' ends to facilitate manipulation of the dsRNA molecule but that do not materially affect the basic characteristics or function of the dsRNA molecule in RNA interference (RNAi).

In some embodiments, the portion of the mRNA polynucleotide transcribable from a *Diabrotica* IAP gene that the antisense strand is complementary to comprises at least 18 consecutive nucleotides of SEQ ID NO:3, SEQ ID NO:12, SEQ ID NO:15 or SEQ ID NO:18. In other embodiments, the portion of mRNA comprises, consists essentially of or consists of at least from 19, 20 or 21 consecutive nucleotides to at least 400 consecutive nucleotides of SEQ ID NO:3, SEQ ID NO:12, SEQ ID NO:15 or SEQ ID NO:18. In other embodiments, the portion of mRNA comprises, consists essentially of or consists of at least about 500, or at least about 507 or at least about 543 consecutive nucleotides of SEQ ID NO:3.

In other embodiments, the portion of the mRNA polynucleotide that is complementary to the antisense strand of a dsRNA of the invention comprises any 19-mer subsequence of SEQ ID NO:3 (wcrIAP1) consisting of N to N+18 nucleotides, wherein N is nucleotide 1 to 1604 of SEQ ID NO:3. In other words, the portion of the mRNA that is targeted comprises any of the 1604 19 consecutive nucleotide subsequences (i.e. 19-mer) of SEQ ID NO:3, for example, bases 1-19 (5'-GAGUAUCGAGUGAGAAAUC-3') (SEQ ID NO:25), bases 2-20 (5'-AGUAUCGAGUGA-GAAAUCG-3') (SEQ ID NO:26), bases 3-21 (5'-GUAUC-GAGUGAGAAAUCGU-3') (SEQ ID NO:27) and so forth to bases 1604-1622 (5'-AUAUAGUAAUUUAUAAUAU-3') (SEQ ID NO:28).

In other embodiments, the portion of the mRNA polynucleotide that is complementary to the antisense strand of a dsRNA of the invention comprises any 19-mer subsequence of SEQ ID NO:12 (wcrIAP2) consisting of N to N+18 nucleotides, wherein N is nucleotide 1 to nucleotide 1444 of SEQ ID NO:12. In other words, the portion of the mRNA that is targeted comprises any of the 1444 19 consecutive nucleotide subsequences (i.e. 19-mers) of SEQ ID NO: 12, for example bases 1-19 (5'-UCAGAAUG-GAAUUAUGGCG-3') (SEQ ID NO:29), bases 2-20 (5'-CAGAAUGGAAUUAUGGCGA-3') (SEQ ID NO:30), bases 3-21 (5'-AGAAUGGAAUUAUGGCGAU-3') (SEQ ID NO:31) and so forth to bases 1444-1462 (5'-AUUAAAAUAAUUGUUUCCU-3') (SEQ ID NO:32).

In other embodiments, the portion of the mRNA polynucleotide that is complementary to the antisense strand of a dsRNA of the invention comprises any 19-mer subsequence of SEQ ID NO:15 (scrIAP1) consisting of N to N+18 nucleotides, wherein N is nucleotide 1 to nucleotide 1018 of SEQ ID NO:15. In other words, the portion of the mRNA that is targeted comprises any of the 1015 19 consecutive nucleotide subsequences (i.e. 19-mer) of SEQ ID NO:15, for example, bases 1-19 (5'-AUGGCAGGUAGUCAAUCAA-3') (SEQ ID NO:33), bases 2-20 (5'-UGGCAGGUAGU-CAAUCAAA-3') (SEQ ID NO:34), bases 3-21 (5'-GGCA-GGUAGUCAAUCAAAU-3') (SEQ ID NO:35) and so forth to bases 1015-1033 (5'-GUCAGAGCGUUUCCUAUCA-3') (SEQ ID NO:36).

In still other embodiments, the portion of the mRNA polynucleotide that is complementary to the antisense strand of a dsRNA of the invention comprises any 19-mer subsequence of SEQ ID NO:18 (ncrIAP1) consisting of N to N+18 nucleotides, wherein N is nucleotide 1 to nucleotide 1020 of SEQ ID NO:18. In other words, the portion of the mRNA that is targeted comprises any of the 1020 19 consecutive nucleotide subsequences (i.e. 19-mer) of SEQ ID NO:18, for example, bases 1-19 (5'-AGUCAAU-CAAAUUACAUUC-3') (SEQ ID NO:37), bases 2-20 (5'-GUCAAUCAAAUUACAUUCA-3') (SEQ ID NO:38), bases 3-21 (5'-UCAAUCAAAUUACAUUCAA-3') (SEQ ID NO:38) and so forth to bases 1020-1038 (5'-AGUCA-GAGCGUUUCCUAUC-3') (SEQ ID NO:40).

In still other embodiments, the portion of the mRNA that is complementary to the antisense sequence of a dsRNA of the invention consists essentially of SEQ ID NO:5, SEQ ID NO:7 or SEQ ID NO:9. In other embodiments, the portion of the mRNA polynucleotide consists essentially of SEQ ID NO:3, SEQ ID NO:12, SEQ ID NO:15 or SEQ ID NO:18.

In further embodiments of the dsRNA molecule of this invention, the nucleotide sequence of the antisense strand can consist essentially of the nucleotide sequence of any 19-mer subsequence of SEQ ID NO:4 (wcrIAP1*) consisting of N to N+18 nucleotides, wherein N is nucleotide 1 to 1603 of SEQ ID NO:4. In other words, the antisense strand consists essentially of any of the 1604 19 consecutive nucleotide subsequences (i.e. 19-mer) of SEQ ID NO:4, for example, bases 1-19 (5'-GAGUAUCGAGUGAGAAAUC-3') (SEQ ID NO:41), bases 2-20 (5'-AGUAUCGAGUGA-GAAAUCG-3') (SEQ ID NO:42), bases 3-21 (5'-GUAUC-GAGUGAGAAAUCGU-3') (SEQ ID NO:43) and so forth to bases 1604-1622 (5'-AUAUAGUAAUUUAUAAUAU-3') (SEQ ID NO:44).

In other embodiments, the nucleotide sequence of the antisense strand can consist essentially of the nucleotide sequence of any 19-mer subsequence of SEQ ID NO:13 (wcrIAP2*) consisting of N to N+18 nucleotides, wherein N is nucleotide 1 to nucleotide 1444 of SEQ ID NO:13. In other words, the antisense strand consists essentially of the 1444 19 consecutive nucleotide subsequences (i.e. 19-mer) of SEQ ID NO:13, for example, bases 1-19 (5'-CGC-CAUAAUUCCAUUCUGA-3') (SEQ ID NO:45), bases 2-20 (5'-UCGCCAUAAUUCCAUUCUG-3') (SEQ ID NO:46), bases 3-21 (5'-AUCGCCAUAAUUCCAUUCU-3') (SEQ ID NO:47) and so forth to bases 1444-1462 (5'-AGGAAACAAUUAUUUUAAU-3') (SEQ ID NO:48).

In other embodiments, the nucleotide sequence of the antisense strand can consist essentially of the nucleotide sequence of any 19-mer subsequence of SEQ ID NO:16 (scrIAP1*) consisting of N to N+18 nucleotides, wherein N is nucleotide 1 to nucleotide 1018 of SEQ ID NO:16. In other words, the antisense strand consists essentially of the nucleotide sequence of any of the 1015 19 consecutive nucleotide subsequences (i.e. 19-mer) of SEQ ID NO:16, for example, bases 1-19 (5'-UUGAUUGACUACCUGCCAU-3') (SEQ ID NO:49), bases 2-20 (5'-UUUGAUUGACUAC-CUGCCA-3') (SEQ ID NO:50), bases 3-21 (5'-AUUUGAUUGACUACCUGCC-3') (SEQ ID NO:51) and so forth to bases 1015-1033 (5'-UGAUAGGAAACGCU-CUGAC-3') (SEQ ID NO:52).

In other embodiments, the nucleotide sequence of the antisense strand can consist essentially of the nucleotide sequence of any 19-mer subsequence of SEQ ID NO:19 (ncrIAP1*) consisting of N to N+18 nucleotides, wherein N is nucleotide 1 to nucleotide 1020 of SEQ ID NO:19. In other words, the antisense strand consists essentially of the nucleotide sequence of any of the 1020 19 consecutive nucleotide subsequences (i.e. 19-mer) of SEQ ID NO:19, for example, bases 1-19 (5'-GAAUGUAAUUUGAUUGACU-3') (SEQ ID NO:53), bases 2-20 (5'-UGAAU-GUAAUUUGAUUGAC-3') (SEQ ID NO:54), bases 3-21 (5'-UUGAAUGUAAUUUGAUUGA-3') (SEQ ID NO:55) and so forth to bases 1015-1033 (5'-GAUAGGAAACGCU-CUGACU-3') (SEQ ID NO:56).

In still other embodiments, the nucleotide sequence of the antisense strand of a dsRNA of the invention that is complementary or substantially complementary to a portion of a mRNA polynucleotide transcribable from a *Diabrotica* insect IAP gene comprises, consists essentially of or consists of the nucleotide sequence of SEQ ID NO:6, SEQ ID NO:8 or SEQ ID NO:10. In other embodiments, the antisense strand comprises, consists essentially of or consists of the nucleotide sequence of SEQ ID NO:5, SEQ ID NO:7, SEQ ID NO:9, SEQ ID NO:12, SEQ ID NO:15 or SEQ ID NO:18. It is to be understood that any of the 19-mer sequences of SEQ ID NO:4, SEQ ID NO:13, SEQ ID NO:16 or SEQ ID NO:19 can have one nucleotide at either the 3' or 5' end deleted or can have up to 6 nucleotides added at the 3' end, the 5' end or both, in any combination to achieve an antisense strand consisting essentially of the 19-mer nucleotide sequence of any of SEQ ID NO:4, SEQ ID NO:13, SEQ ID NO:16 or SEQ ID NO:19, as it would be understood that the deletion of the one nucleotide or the addition of up to the six nucleotides do not materially affect the basic characteristics or function of the double stranded RNA molecule of the invention. Such additional nucleotides can be nucleotides that extend the complementarity of the antisense strand along the target sequence and/or such nucleotides can be nucleotides that facilitate manipulation of the RNA molecule or a nucleic acid molecule encoding the RNA molecule, as would be known to one of ordinary skill in the art. For example, a TT overhang at the 3; end may be present, which is used to stabilize the siRNA duplex and does not affect the specificity of the siRNA.

In some embodiments of this invention, the antisense strand of the double stranded RNA molecule can be fully complementary to the target RNA polynucleotide or the antisense strand can be substantially complementary or partially complementary to the target RNA polynucleotide. By substantially or partially complementary is meant that the antisense strand and the target RNA polynucleotide can be mismatched at about 1, 2, 3, 4, 5, 6, 7, 8, 9, or 10 nucleotide pairings. Such mismatches can be introduced into the antisense strand sequence, e.g., near the 3' end, to enhance processing of the double stranded RNA molecule by Dicer, to duplicate a pattern of mismatches in a siRNA molecule inserted into a chimeric nucleic acid molecule or artificial microRNA precursor molecule of this invention (see Examples section), and the like, as would be known to one of skill in the art. Such modification will weaken the base pairing at one end of the duplex and generate strand asymmetry, therefore enhancing the chance of the antisense strand, instead of the sense strand, being processed and silencing the intended gene (Geng and Ding "Double-mismatched siRNAs enhance selective gene silencing of a mutant ALS-causing Allele1" *Acta Pharmacol. Sin.* 29:211-216 (2008); Schwarz et al. "Asymmetry in the assembly of the RNAi enzyme complex" *Cell* 115:199-208 (2003)). Other such mismatches can be introduced into the antisense strand due to eliminating fortuitous open reading frames created in making dsRNA encoding expression cassettes. Such open reading frames are eliminated by making point mutations in the dsRNA encoding nucleotide sequence thus creating some mismatches in the dsRNA compared to the target gene. In one embodiment of this invention, such mismatches are introduced into a nucleotide sequence encoding the sense strand wcrIAP1-C(SEQ ID NO:9) resulting in a nucleotide sequence encoding a mutated sense strand designated wcrIAP1-Ca (nucleotides 1-500 of SEQ ID NO:64).

In some embodiments of this invention, the dsRNA molecule of the invention is a short hairpin RNA (shRNA) molecule. Expression of shRNA in cells is typically accomplished by delivery of plasmids or recombinant vectors, for example in transgenic plants such as transgenic corn.

The invention encompasses a nucleic acid molecule encoding at least one strand of a dsRNA molecule of the invention. The invention further encompasses a nucleic acid construct comprising at least one strand of a dsRNA molecule of the invention or comprising the nucleic acid molecule encoding the at least one strand of a dsRNA molecule of the invention. In one embodiment of the invention, the nucleic acid molecule encodes a short hairpin RNA. In another embodiment, the nucleic acid molecule that encodes the short hairpin RNA comprises SEQ ID NO:63 or SEQ ID NO:64. In another embodiment, the nucleic acid molecule is a recombinant vector. In yet another embodiment, the recombinant vector comprises, consists essentially of or consists of the nucleotide sequence of SEQ ID NO:65 or SEQ ID NO:67.

The invention further encompasses chimeric nucleic acid molecules comprising an antisense strand of a dsRNA of the invention operably linked with a plant microRNA precursor molecule. In some embodiments, the chimeric nucleic acid molecule comprises an antisense strand having the nucleotide sequence of any of the 19-mer subsequences of SEQ ID NO:4, SEQ ID NO:13, SEQ ID NO:16 or SEQ ID NO:19 operably linked with a plant microRNA precursor molecule. In some embodiments, the plant microRNA precursor molecule is a maize microRNA precursor.

In some embodiments, the invention encompasses an artificial plant microRNA precursor molecule comprising an antisense strand of a dsRNA molecule of the invention. In other embodiments, the artificial plant microRNA precursor molecule comprises an antisense strand having the nucleotide sequence of any of the 19-mer subsequences of SEQ ID NO:4, SEQ ID NO:13, SEQ ID NO:16 or SEQ ID NO:19. The use of artificial plant microRNAs to deliver a nucleotide sequence of interest (e.g an artificial miRNA; siRNA/siRNA*) into a plant is known in the art (see, e.g., Schwab et al. 2006. The Plant Cell 18:1121-1133 and Examples section herein). In the invention, the artificial microRNAs are chimeric or hybrid molecules, having a plant microRNA precursor backbone and an insect (i.e. animal) siRNA sequence inserted therein. As would be understood by one of ordinary skill in the art, it is typically desirable to maintain mismatches that normally occur in the plant microRNA precursor sequence in any nucleotide sequence that is substituted into the plant microRNA precursor backbone. In still other embodiments, the artificial plant microRNA precursor comprises portions of a corn microRNA precursor molecule. Any corn microRNA (miRNA) precursor is suitable for the compositions and methods of the invention. Nonlimiting examples include miR156, miR159, miR160, miR162, miR164, miR166, miR167, miR168, miR169, miR171, miR172, miR319, miR390, miR393, miR394, miR395, miR396, miR397, miR398, miR399, miR408, miR482, miR528, miR529, miR827, miR1432, as well as any other plant miRNA precursors now known or later identified.

In some embodiments, the invention encompasses nucleic acid constructs, nucleic acid molecules or recombinant vectors comprising at least one strand of a dsRNA molecule of the invention, or comprising a chimeric nucleic acid molecule of the invention, or comprising an artificial plant microRNA of the invention. In some embodiments the nucleic acid construct comprises a nucleic acid molecule of the invention. In other embodiments, the nucleic acid construct is a recombinant expression vector.

In some embodiments, the invention encompasses compositions comprising two or more dsRNA molecules of the invention wherein the two or more RNA molecules each comprise a different antisense strand. In some embodiments the two or more dsRNA molecules are present on the same nucleic acid construct, on different nucleic acid constructs or any combination thereof. In other embodiments, the composition comprises an RNA molecule comprising an antisense strand consisting essentially of the nucleotide sequence of SEQ ID NO:6 and an RNA molecule comprising an antisense strand consisting essentially of the nucleotide sequence of SEQ ID NO:8 and/or an RNA molecule comprising an antisense strand consisting essentially of the nucleotide sequence of SEQ ID NO:10. In other embodiments, the composition comprises two or more nucleic acid constructs, two or more nucleic acid molecules, two or more chimeric nucleic acid molecules, two or more artificial plant microRNA precursors of the invention, wherein the two or more nucleic acid constructs, two or more nucleic acid molecules, two or more chimeric nucleic acid molecules, or two or more artificial plant microRNA precursors, each comprise a different antisense strand.

In some embodiments, the invention encompasses an insecticidal composition for inhibiting the expression of a *Diabrotica* insect IAP gene, comprising a dsRNA or siRNA of the invention and an agriculturally acceptable carrier. In some embodiments, the acceptable agricultural carrier is a transgenic organism expressing a dsRNA or siRNA of the invention. In some embodiments the transgenic organism may be a transgenic plant expressing the dsRNA or siRNA of the invention that when fed upon by a target pest causes the target pest to stop feeding, growing or reproducing or causing death of the target pest. In other embodiments, the transgenic plant is a transgenic corn plant and the target pest is a *Diabrotica* insect pest. In still other embodiments, the *Diabrotica* insect pest is selected from the group consisting of *Diabrotica barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (*chrysanthemum* beetle), *D. virgifera zeae* (Mexican corn rootworm).

In other embodiments, the transgenic organism is selected from, but not limited to, the group consisting of: yeast, fungi, algae, bacteria, virus or an arthropod expressing the dsRNA or siRNA of the invention. In some embodiments, the transgenic organism is a virus, for example an insect baculovirus that expresses a dsRNA or siRNA of the invention upon infection of an insect host. Such a baculovirus is likely more virulent against the target insect than the wildtype untransformed baculovirus. In other embodiments the transgenic organism is a transgenic bacterium that is applied to an environment where a target pest occurs or is known to have occurred. In some embodiments, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive dsRNA or siRNA for the same purpose.

In some embodiments, an acceptable agricultural carrier is a formulation useful for applying the composition comprising the dsRNA or siRNA to a plant or seed. In some embodiments, the dsRNA or siRNA molecules are stabilized against degradation because of their double stranded nature and the introduction of Dnase/Rnase inhibitors. For example, the dsRNA or siRNA can be stabilized by including thymidine or uridine nucleotide 3' overhangs. The dsRNA or siRNA contained in the compositions of the invention can be chemically synthesized at industrial scale in large amounts. Methods available would be through chemical synthesis or through the use of a biological agent.

In other embodiments the formulation comprises a transfection promoting agent. In other embodiments, the transfection promoting agent is a lipid-containing compound. In further embodiments, the lipid-containing compound is selected from the group consisting of; Lipofectamine, Cellfectin, DMRIE-C, DOTAP and Lipofectin. In another embodiment, the lipid-containing compound is a Tris cationic lipid.

In some embodiments, the formulation further comprises a nucleic acid condensing agent. The nucleic acid condensing agent can be any such compound known in the art. Examples of nucleic acid condensing agents include, but are not limited to, spermidine (N-[3-aminopropyl]-1,4-butanediamine), protamine sulphate, poly-lysine as well as other positively charged peptides. In some embodiments, the nucleic acid condensing agent is spermidine or protamine sulfate.

In still further embodiments, the formulation further comprises buffered sucrose or phosphate buffered saline.

In some embodiments, the invention encompasses transgenic plants, or parts thereof, comprising a dsRNA molecule, a nucleic acid construct, a chimeric nucleic acid molecule, a artificial plant microRNA precursor molecule and/or a composition of the invention, wherein the transgenic plant has enhanced resistance to a *Diabrotica* insect as compared to a control plant. In other embodiments, the transgenic plant, or part thereof, is a transgenic corn plant, or part thereof. The invention further encompasses transgenic seed of the transgenic plants of the inventions, wherein the transgenic seed comprises a dsRNA molecule, a nucleic acid construct, a chimeric nucleic acid molecule, a artificial plant microRNA precursor molecule and/or a composition of the invention. In some embodiments the transgenic seed is a transgenic corn seed.

Transgenic plants expressing dsRNA or siRNA of the invention are tolerant or resistant to attack by target insect pests. When the insect starts feeding on such a transgenic plant, it also ingests the expressed dsRNA or siRNA. This will deter the insect from further biting into the plant tissue or may even harm or kill the insect. A nucleic acid sequence encoding a dsRNA or siRNA of the invention is inserted into an expression cassette, which is then preferably stably integrated in the genome of the plant. Plants transformed in accordance with the present invention may be monocots or dicots and include, but are not limited to, corn, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees. In further embodiments, the transgenic plant is a transgenic corn plant.

Expression of the dsRNA or siRNA in transgenic plants is driven by promoters that function in plants. The choice of promoter will vary depending on the temporal and spatial requirements for expression, and also depending on the insect target species. Thus, expression of the interfering RNAs of this invention in leaves, in stalks or stems, in ears, in inflorescences (e.g. spikes, panicles, cobs, etc.), in roots, and/or seedlings is contemplated. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the dsRNA or siRNA in the desired cell.

Promoters useful with the invention include, but are not limited to, those that drive expression of a nucleotide sequence constitutively, those that drive expression when induced, and those that drive expression in a tissue- or developmentally-specific manner. These various types of promoters are known in the art.

Examples of constitutive promoters include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), figwort mosaic virus (fmv) promoter (Govindarajulu et al. 2008. *Mol Plant Microbe Interact* 21:1027-35) and the ubiquitin promoter (Ubi). The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926.

In some embodiments, tissue specific/tissue preferred promoters can be used. Tissue specific or preferred expression patterns include, but are not limited to, green tissue specific or preferred, root specific or preferred, stem specific or preferred, and flower specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in roots or particular cells in roots, pith, leaf or pollen. Such promoters are disclosed, for example without limitation, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; and the cestrum yellow leaf curling virus promoter disclosed in WO 01/73087, all incorporated herein by reference.

Additional examples of tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *petunia chalcone* isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612). In some particular embodiments, the nucleotide sequences of the invention are operably associated with a root-preferred promoter. Particularly useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched on at the onset of senescence, such as the SAG promoter from *Arabidopsis* (Gan et al. (1995) *Science* 270:1986-1988).

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in a plant through the application of an exogenous chemical regulator. Regulation of the expression of nucleotide sequences of the invention via promoters that are chemically regulated enables the polypeptides of the invention to be synthesized only when the crop plants are treated with the inducing chemicals. Depending upon the objective, the promoter may be a chemical-inducible promoter, where application of a chemical induces gene expression, or a chemical-repressible promoter, where application of the chemical represses gene expression.

Chemical inducible promoters are known in the art and include, but are not limited to, the maize Int-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid (e.g., the PR1a system), steroid steroid-responsive promoters (see, e.g., the glucocorticoid-inducible promoter in Schena et al. (1991) Proc. Natl. Acad. Sci. USA 88, 10421-10425 and McNellis et al. (1998) Plant J. 14, 247-257) and tetracycline-inducible and tetracycline-repressible promoters (see, e.g., Gatz et al. (1991) Mol. Gen. Genet. 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) Plant J. 11:605-612), and ecdysone-inducible system promoters.

Other non-limiting examples of inducible promoters include ABA- and turgor-inducible promoters, the auxin-binding protein gene promoter (Schwob et al. (1993) Plant J. 4:423-432), the UDP glucose flavonoid glycosyl-transferase promoter (Ralston et al. (1988) Genetics 119:185-197), the MPI proteinase inhibitor promoter (Cordero et al. (1994) Plant J. 6:141-150), and the glyceraldehyde-3-phosphate dehydrogenase promoter (Kohler et al. (1995) Plant Mol. Biol. 29:1293-1298; Martinez et al. (1989) J. Mol. Biol. 208:551-565; and Quigley et al. (1989) J. Mol. Evol. 29:412-421). Also included are the benzene sulphonamide-inducible (U.S. Pat. No. 5,364,780) and alcohol-inducible (Intl Patent Application Publication Nos. WO 97/06269 and WO 97/06268) systems and glutathione S-transferase promoters. Likewise, one can use any of the inducible promoters described in Gatz (1996) Current Opinion Biotechnol. 7:168-172 and Gatz (1997) Annu. Rev. Plant Physiol. Plant Mol. Biol. 48:89-108. Other chemically inducible promoters useful for directing the expression of the nucleotide sequences of this invention in plants are disclosed in U.S. Pat. No. 5,614,395 herein incorporated by reference in its entirety. Chemical induction of gene expression is also detailed in the published application EP 0 332 104 (to Ciba-Geigy) and U.S. Pat. No. 5,614,395. In some embodiments, a promoter for chemical induction can be the tobacco PR-1a promoter.

In further aspects, the nucleotide sequences of the invention can be operably associated with a promoter that is wound inducible or inducible by pest or pathogen infection (e.g., a nematode plant pest). Numerous promoters have been described which are expressed at wound sites and/or at the sites of pest attack (e.g., insect/nematode feeding) or phytopathogen infection. Ideally, such a promoter should be active only locally at or adjacent to the sites of attack, and in this way expression of the nucleotide sequences of the invention will be focused in the cells that are being invaded. Such promoters include, but are not limited to, those described by Stanford et al., Mol. Gen. Genet. 215:200-208 (1989), Xu et al. Plant Molec. Biol. 22:573-588 (1993), Logemann et al. Plant Cell 1:151-158 (1989), Rohrmeier and Lehle, Plant Molec. Biol. 22:783-792 (1993), Firek et al. Plant Molec. Biol. 22:129-142 (1993), Warner et al. Plant J. 3:191-201 (1993), U.S. Pat. No. 5,750,386, U.S. Pat. No. 5,955,646, U.S. Pat. No. 6,262,344, U.S. Pat. No. 6,395,963, U.S. Pat. No. 6,703,541, U.S. Pat. No. 7,078,589, U.S. Pat. No. 7,196,247, U.S. Pat. No. 7,223,901, and U.S. Patent Application Publication 2010043102.

In some embodiments of the present invention, a "minimal promoter" or "basal promoter" is used. A minimal promoter is capable of recruiting and binding RNA polymerase II complex and its accessory proteins to permit transcriptional initiation and elongation. In some embodiments, a minimal promoter is constructed to comprise only the nucleotides/nucleotide sequences from a selected promoter that are required for binding of the transcription factors and transcription of a nucleotide sequence of interest that is operably associated with the minimal promoter including but not limited to TATA box sequences. In other embodiments, the minimal promoter lacks cis sequences that recruit and bind transcription factors that modulate (e.g., enhance, repress, confer tissue specificity, confer inducibility or repressibility) transcription. A minimal promoter is generally placed upstream (i.e., 5') of a nucleotide sequence to be expressed. Thus, nucleotides/nucleotide sequences from any promoter useable with the present invention can be selected for use as a minimal promoter.

In some embodiments, a recombinant nucleic acid molecule of the invention can be an "expression cassette." As used herein, "expression cassette" means a recombinant nucleic acid molecule comprising a nucleotide sequence of interest (e.g., the nucleotide sequences of the invention), wherein the nucleotide sequence is operably associated with at least a control sequence (e.g., a promoter). Thus, some embodiments of the invention provide expression cassettes designed to express nucleotides sequences encoding the dsRNAs or siRNAs of the invention. In this manner, for example, one or more plant promoters operably associated with one or more nucleotide sequences of the invention are provided in expression cassettes for expression in a corn plant, plant part and/or plant cell.

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used.

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of the invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac," pp. 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin, which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of the invention.

An expression cassette of the invention also can include polynucleotides that encode other desired traits. Such desired traits can be other polynucleotides which confer insect resistance, or which confer nematode resistance, or other agriculturally desirable traits. Such polynucleotides can be stacked with any combination of nucleotide sequences to create plants, plant parts or plant cells having the desired phenotype. Stacked combinations can be created by any method including, but not limited to, cross breeding plants by any conventional methodology, or by genetic transformation. If stacked by genetically transforming the plants, nucleotide sequences encoding additional desired traits can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or other composition of the invention, provided by any combination of expression cassettes. For example, if two nucleotide sequences will be introduced, they can be incorporated in separate cassettes (trans) or can be incorporated on the same cassette (cis). Expression of the nucleotide sequences can be driven by the same promoter or by different promoters. It is further recognized that nucleotide sequences can be stacked at a desired genomic location using a site-specific recombination system. See, e.g., Intl Patent Application Publication Nos. WO 99/25821; WO 99/25854; WO 99/25840; WO 99/25855 and WO 99/25853.

Thus, an expression cassette can include a coding sequence for one or more polypeptides for agronomic traits that primarily are of benefit to a seed company, grower or grain processor. A polypeptide of interest can be any polypeptide encoded by a polynucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, and/or fungal resistance. See, e.g., U.S. Pat. Nos. 5,569,823; 5,304,730; 5,495,071; 6,329,504; and 6,337,431.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4:1093-1096 (1986)). For both direct gene transfer and *Agrobacterium*-mediated transfer, transformation is usually (but not necessarily) undertaken with a selectable marker that may provide resistance to an antibiotic (kanamycin, hygromycin or methotrexate) or a herbicide (basta). Plant transformation vectors comprising expression cassettes that encode a short hairpin RNA of the invention may also comprise genes, for example, phosphomannose isomerase (pmi), which provides for positive selection of the transgenic plants as disclosed in U.S. Pat. Nos. 5,767,378 and 5,994,629, herein incorporated by reference, or phosphinotricin acetyltransferase (pat), which provides tolerance to the herbicide phosphinotricin (glufosinate). The choice of selectable marker is not, however, critical to the invention. In one embodiment, the vector suitable for plant transformation comprises, consists essentially of or consists of a nucleotide sequence of SEQ ID NO:65 or SEQ ID NO:67.

In other embodiments, a nucleic acid sequence of the invention is directly transformed into the plastid genome. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleic acid sequence of the present invention is inserted into a plastid-targeting vector and transformed into the plastid genome of a desired plant host. Plants homoplastic for plastid genomes containing a nucleic acid sequence of the present invention are obtained, and are preferentially capable of high expression of the nucleic acid sequence.

Transgenic plants or seed comprising a dsRNA or siRNA of the invention can also be treated with an insecticide or insecticidal seed coating as described in U.S. Pat. Nos. 5,849,320 and 5,876,739, herein incorporated by reference. Where both the insecticide or insecticidal seed coating and the transgenic plant or seed of the invention are active against the same target insect, for example a *Diabrotica* target pest, the combination is useful (i) in a method for further enhancing activity of the composition of the invention against the target insect, and (ii) in a method for preventing development of resistance to the composition of the invention by providing yet another mechanism of action against the target insect. Thus, the invention provides a method of enhancing control of a *Diabrotica* insect population comprising providing a transgenic plant or seed of the invention and applying to the plant or the seed an insecticide or insecticidal seed coating to a transgenic plant or seed of the invention. Examples of such insecticides and/or insecticidal seed coatings include, without limitation, a carbamate, a pyrethroid, an organophosphate, a friprole, a neonicotinoid, an organochloride, a nereistoxin, or a combination thereof. In another embodiment, the insecticide or insecticidal seed coating are selected from the group consisting of carbofuran, carbaryl, methomyl, bifenthrin, tefluthrin, permethrin, cyfluthrin, lambda-cyhalothrin, cypermethrin, deltamethrin, chlorpyrifos, chlorethoxyfos, dimethoate, ethoprophos, malathion, methyl-parathion, phorate, terbufos, tebupirimiphos, fipronil, acetamiprid, imidacloprid, thiacloprid, thiamethoxam, endosulfan, bensultap, and a combination thereof. Commercial products containing such insecticides and insecticidal seed coatings include, without limitation, Furadan®, Lanate®, Sevin®, Talstar®, Force®, Ammo®, Cymbush®, Delta Gold®, Karate®, Ambush®, Pounce®, Brigade®, Capture®, ProShield®, Warrior®, Dursban®, Fortress®, Mocap®, Thimet®, AAstar®, Rampart®, Counter®, Cygon®, Dicap®, Regent®, Cruiser®, Gaucho®, Prescribe®, Poncho® and Aztec®.

The compositions of the invention can also be combined with other biological control agents to enhance control of *Diabrotica* insect populations. Thus, the invention provides a method of enhancing control of a *Diabrotica* insect population by providing a transgenic plant that produces a dsRNA of the invention and further comprises a polynucleotide that encodes a pesticidal agent selected from the group consisting of a patatin, a protease, a *Bacillus thuringiensis* insecticidal protein, a *Xenorhabdus* insecticidal protein or protein complex, a *Photorhabdus* insecticidal protein or protein complex, a *Bacillus laterosporus* insecticidal protein or protein complex, and a *Bacillus sphaericus* insecticidal protein. In some embodiments, the *Bacillus thuringiensis* insecticidal protein is selected from the group consisting of a Cry1 protein, a Cry3 protein, a Cry 7 protein, a Cry8 protein, a Cry 23 protein, a Cry 36 protein, a Cry37 protein, a Cry34 protein together with a Cry35 protein, a modified Cry3A protein, and hybrid proteins made therefrom. In other embodiments, the *Bacillus thuringiensis* insecticidal protein is selected from the group consisting of Cry3Bb1, Cry34Ab1 together with Cry35Ab1, mCry3A and eCry3.1Ab. In another embodiment, the transgenic plant and transgenic seed is a corn plant or corn seed. In another embodiment, the transgenic corn plant is provided by crossing a first transgenic corn plant comprising a dsRNA of the invention with a transgenic corn plant comprising a transgenic event selected from the group consisting of MIR604, Event 5307, DAS51922-7, MON863 and MON88017.

Even where the insecticide or insecticidal seed coating is active against a different insect, the insecticide or insecticidal seed coating is useful to expand the range of insect control, for example by adding an insecticide or insecticidal seed coating that has activity against lepidopteran insects to the transgenic plant or seed of the invention, which has activity against coleopteran insects, the treated plant or coated transgenic seed controls both lepidopteran and coleopteran insect pests.

In further embodiments, the invention encompasses a biological sample from a transgenic plant, seed, or parts thereof, of the invention, wherein the sample comprises a nucleic acid that is or encodes at least one strand of a dsRNA of the invention. In other embodiments, the invention encompasses a commodity product derived from a transgenic plant, seed, or parts thereof, of the invention. In some embodiments, the commodity product is selected from the group consisting of whole or processed seeds, beans, grains, kernels, hulls, meals, grits, flours, sugars, sugars, starches, protein concentrates, protein isolates, waxes, oils, extracts, juices, concentrates, liquids, syrups, feed, silage, fiber, paper or other food or product produced from plants. In other embodiments, the biological sample or commodity product is toxic to insects. In other embodiments, the transgenic plant is transgenic corn plant.

The invention further encompasses a method of controlling a *Diabrotica* insect comprising contacting the *Diabrotica* insect with a nucleic acid molecule that is or is capable of producing an interfering RNA of the invention for inhibiting expression of an IAP gene in the *Diabrotica* insect thereby controlling the *Diabrotica* insect. In some embodiments, the IAP gene comprises a IAP coding sequence having from at least about 90% identity to at least about 99% identity to SEQ ID NO:2. In some embodiments the IAP coding sequence is selected from the group consisting of SEQ ID NO:2, SEQ ID NO:11, SEQ ID NO:14 and SEQ ID NO:17. In other embodiments, the interfering RNA is complementary to a portion of a mRNA polynucleotide transcribable from the IAP gene. In other embodiments, the portion of the mRNA polynucleotide comprises from 18, 19, 20 or 21 consecutive nucleotides to at least about 400 consecutive nucleotides of SEQ ID NO:3, SEQ ID NO:12, SEQ ID NO:15 or SEQ ID NO:18. In some embodiments, the portion of the mRNA polynucleotide consists essentially of (a) any 19-mer subsequence of SEQ ID NO:3 (wcrIAP1) consisting of N to N+18 nucleotides, wherein N is nucleotide 1 to 1603 of SEQ ID NO:3; or (b) any 19-mer subsequence of SEQ ID NO:12 (wcrIAP2) consisting of N to N+18 nucleotides, wherein N is nucleotide 1 to nucleotide 1444 of SEQ ID NO:12; or (c) any 19-mer subsequence of SEQ ID NO:15 (scrIAP1) consisting of N to N+18 nucleotides, wherein N is nucleotide 1 to nucleotide 1018 of SEQ ID NO:15; or (d) any 19-mer subsequence of SEQ ID NO:18 (ncrIAP1) consisting of N to N+18 nucleotides, wherein N is nucleotide 1 to nucleotide 1020 of SEQ ID NO:18. In some embodiments, the portion of the mRNA polynucleotide consists essentially of the nucleotide sequence of SEQ ID NO:3, SEQ ID NO:5, SEQ ID NO:7, SEQ ID NO:9, SEQ ID NO:12, SEQ ID NO:15 or SEQ ID NO:18.

In some embodiments of the method of controlling a *Diabrotica* pest, the nucleotide sequence of the interfering RNA consists essentially of (a) any 19-mer subsequence of SEQ ID NO:4 (wcrIAP1*) consisting of N to N+18 nucleotides, wherein N is nucleotide 1 to 1603 of SEQ ID NO:4; or (b) any 19-mer subsequence of SEQ ID NO:13 (wcrIAP2*) consisting of N to N+18 nucleotides, wherein N is nucleotide 1 to nucleotide 1444 of SEQ ID NO:13; or (c) any 19-mer subsequence of SEQ ID NO:16 (scrIAP1*) consisting of N to N+18 nucleotides, wherein N is nucleotide 1 to nucleotide 1018 of SEQ ID NO:16; or (d) any 19-mer subsequence of SEQ ID NO:19 (ncrIAP1*) consisting of N to N+18 nucleotides, wherein N is nucleotide 1 to nucleotide 1020 of SEQ ID NO:19. In yet further embodiments, the nucleotide sequence of the interfering RNA consists essentially of the nucleotide sequence of SEQ ID NO:4, SEQ ID NO:6, SEQ ID NO:8, SEQ ID NO:10, SEQ ID NO:13, SEQ ID NO:16, or SEQ ID NO:19.

In some embodiments of the method of controlling *Diabrotica*, the *Diabrotica* insect is selected from the group consisting of *D. barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (*chrysanthemum* beetle) and *D. virgifera zeae* (Mexican corn rootworm).

In other embodiments of the method of controlling the *Diabrotica* insect, the contacting comprises (a) planting a transgenic seed capable of producing a transgenic plant that expresses the nucleic acid molecule, wherein the *Diabrotica* insect feeds on the transgenic plant, or part thereof; or (b) applying a composition comprising the nucleic acid molecule to a seed or plant, or part thereof, wherein the *Diabrotica* insect feeds on the seed, the plant, or a part thereof. In some embodiments, the transgenic seed and the transgenic plant is a corn seed or a corn plant. In other embodiments the seed or plant is a corn seed or a corn plant.

The invention also encompasses a method of reducing an adult *Diabrotica* insect population on a transgenic plant expressing a Cry protein, a hybrid Cry protein or modified Cry protein comprising expressing in the transgenic plant a nucleic acid molecule that is or is capable of producing an interfering RNA capable of inhibiting expression of an IAP gene in an adult *Diabrotica* insect thereby reducing the adult *Diabrotica* insect population.

In some embodiments, the invention encompasses a method of reducing the level of a target mRNA transcribable from a IAP gene in a *Diabrotica* insect comprising feeding to the *Diabrotica* insect a composition comprising the dsRNA molecule of the invention, wherein the dsRNA molecule reduces the level of the target mRNA in a cell of the *Diabrotica* insect. In other embodiments, production of a IAP protein encoded by the target mRNA is reduced. In other embodiments, the IAP protein is an IAP1 or IAP2 protein. In other embodiments, the IAP protein comprises an amino acid having at least about 90%, at least about 91%, at least about 92%, at least about 93%, at least about 94%, at least about 95%, at least about 96%, at least about 97%, at least about 98% or at least about 99% identity to SEQ ID NO:20. In other embodiments the IAP protein comprises an amino acid sequence selected from the group consisting of SEQ ID NO:20, SEQ ID NO:21, SEQ ID NO:22 and SEQ ID NO:23. In other embodiments, the dsRNA is contacted with a *Diabrotica* insect through a transgenic organism expressing the dsRNA. In other embodiments, the transgenic organism is a transgenic plant, a transgenic bacterium or a transgenic endophyte. In other embodiments, the dsRNA is contacted with a *Diabrotica* insect by topically applying a dsRNA in an acceptable agricultural carrier to a plant or plant part on which the *Diabrotica* insects feeds. In some embodiments, the dsRNA that reduces the level of a target mRNA transcribable from a IAP gene in a *Diabrotica* insect is lethal to the *Diabrotica* insect. In other embodiments, the *Diabrotica* insect is selected from the group consisting of *D.*

*barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (*chrysanthemum* beetle) and *D. virgifera zeae* (Mexican corn rootworm).

In some embodiments, the invention encompasses a method of conferring *Diabrotica* insect tolerance to a plant, or part thereof, comprising introducing into the plant, or part thereof, a dsRNA molecule, a nucleic acid construct, a chimeric nucleic acid molecule, a artificial plant microRNA precursor molecule and/or a composition of the invention, thereby conferring tolerance of the plant or part thereof to the *Diabrotica* insect. In one embodiment the nucleic acid construct or the chimeric nucleic acid molecule comprises the nucleotide sequence of SEQ ID NO:63 or SEQ ID NO:64. In another embodiment, the chimeric nucleic acid molecule is a vector comprising a nucleotide sequence of SEQ ID NO:65 or SEQ ID NO:67.

In other embodiments, the invention encompasses a method of reducing root damage to a plant fed upon by a *Diabrotica* insect, comprising introducing into cells of the plant a dsRNA, a nucleic acid molecule, a nucleic acid construct, a chimeric nucleic acid molecule, a artificial plant microRNA precursor molecule and/or a composition of any of the respective preceding claims, thereby reducing root damage to the plant. In one embodiment the nucleic acid construct or the chimeric nucleic acid molecule comprises the nucleotide sequence of SEQ ID NO:63 or SEQ ID NO:64. In another embodiment, the chimeric nucleic acid molecule is a vector comprising a nucleotide sequence of SEQ ID NO:65 or SEQ ID NO:67.

In still other embodiments, the invention encompasses a method of producing a transgenic plant cell having toxicity to a *Diabrotica* insect, comprising introducing into a plant cell a dsRNA, a nucleic acid molecule, a nucleic acid construct, a chimeric nucleic acid molecule, a artificial plant microRNA precursor molecule and/or a composition of the invention, thereby producing the transgenic plant cell having toxicity to the *Diabrotica* insect compared to a control plant cell. In some embodiments, the invention encompasses a plurality of transgenic plant cells produced by this method. In other embodiments, the plurality of transgenic plant cells is grown under conditions which include natural sunlight. In one embodiment the nucleic acid construct or the chimeric nucleic acid molecule comprises the nucleotide sequence of SEQ ID NO:63 or SEQ ID NO:64. In another embodiment, the chimeric nucleic acid molecule is a vector comprising a nucleotide sequence of SEQ ID NO:65 or SEQ ID NO:67.

In some embodiments, the invention encompasses a method of producing a transgenic plant having enhanced tolerance to *Diabrotica* insect feeding damage, comprising introducing into a plant a dsRNA, a nucleic acid molecule, a nucleic acid construct, a chimeric nucleic acid molecule, an artificial plant microRNA precursor molecule and/or a composition of the invention, thereby producing a transgenic plant having enhanced tolerance to *Diabrotica* insect feeding damage compared to a control plant. In other embodiments, the introducing step is performed by transforming a plant cell and producing the transgenic plant from the transformed plant cell. In still other embodiments, the introducing step is performed by breeding two plants together.

In some embodiments, the invention encompasses a method of providing a corn grower with a means of controlling a *Diabrotica* insect pest population in a corn crop comprising (a) selling or providing to the grower at least one bag of corn seed comprising transgenic corn seed that comprises a dsRNA, a nucleic acid molecule, a nucleic acid construct, a chimeric nucleic acid molecule, an artificial plant microRNA precursor molecule and/or a composition of the invention; and (b) advertising to the grower that the transgenic corn seed produces transgenic corn plants that control a *Diabrotica* pest population.

EXAMPLES

The invention will be further described by reference to the following detailed examples. These examples are provided for the purposes of illustration only, and are not intended to be limiting unless otherwise specified.

Example 1

Identification of IAP Genes in *Diabrotica*

This example describes the cloning and sequencing of inhibitor of apoptosis (iap) genes and coding sequences from *Diabrotica* insects.

*Diabrotica virgifera virgifera* (Western Corn Rootworm; WCR)

A whole-body neonate WCR transcriptome was sequenced by pyrosequencing on a 454 platform (454 Life Sciences, Branford, Conn.) essentially according to the manufacturer's instructions. The resulting reads (i.e., short fragments of nucleic acid sequence) were trimmed and assembled using a MIRA assembler (See, for example, Chevreux et al. 2004. Genome Res. 14:1147-1159, incorporated herein by reference). The resulting contigs were used to make a BLAST database (Attschul et al. 1990. J. Mol. Biol. 215:403-410) using formatdb (NCBI, Bethesda, Md.).

To identify assembled contigs with similarity to a known insect iap gene, a *Drosophila melanogaster* IAP1 (dmIAP1) amino acid sequence (Genbank Accession No. NP730097; SEQ ID NO:24) was used as a query against the WCR transcriptome BLAST database using tblastn (protein query vs. translated nucleotide database). An expect value cutoff of 1e-05 was used. Fifteen WCR sequences were identified and used in an assembly using Contig Express (Vector NTI version 11, Invitrogen, Carlsbad, Calif.) with default parameters. Three contiguous sequences were assembled and the resulting sequences were compared to the Genbank NR database by blastx. A first contig (contg1) was assembled using five 454 contigs sequences and was found to be similar to dmIAP1. The assembly of contig 1 was edited manually to remove low quality base calls and to resolve discrepancies between 454 contigs. The final sequence (wcrIAP1; SEQ ID NO:1) was confirmed by sequencing with the primers shown in Table 1 using standard Sanger sequencing methods. The wcrIAP1 gene is 1622 nucleotides in length and comprises a 145 bp 5' UTR, 1050 bp coding region (position 146 to 1195), and a 427 bp 3' UTR. The encoded WCR-IAP1 amino acid sequence is shown in SEQ ID NO:20.

TABLE 1

Primers used to sequence wcrIAP1

| Primer Name | Sequence (5'→3') | Sequence Identifier |
|---|---|---|
| WCR_IAP_FP01 | AGAGCATTAAACAGAGGCCTTC | SEQ ID NO: 57 |
| WCR_IAP_RP01 | TGATAGGAACGCTCTGACTGTG | SEQ ID NO: 58 |

TABLE 1-continued

Primers used to sequence wcrIAP1

| Primer Name | Sequence (5'→3') | Sequence Identifier |
|---|---|---|
| WCR_IAP_FP02 | ATGGCAGTAGTTCAATCAAATT ACATT | SEQ ID NO: 59 |
| WCR_IAP_RP02 | GCCAACCCTGGAATGTTGC | SEQ ID NO: 60 |
| WCR_IAP_FP03 | TTGTGGTGGGGGATTAAAAG | SEQ ID NO: 61 |
| WCR_IAP_RP03 | CATTTGCTAAACCAAAGGGC | SEQ ID NO: 62 |

A second contig (contig2) was assembled using three 454 contigs and was also manually edited as with contig1. The final assembled sequence is 1462 bp in length and designated wcrIAP2 (SEQ ID NO:11), which contains an incomplete coding sequence at the 5' end. The last 31 bp of wcrIAP2 belongs to the 3' untranslated region (UTR). The encoded WCR-IAP2 amino acid sequence is shown in SEQ ID NO:21.

*Diabrotica undecimpunctata howardi* (Southern Corn Rootworm; SCR)

Commercially-available SCR eggs were purchased (Crop Characteristics, Inc, Farmington, Minn.) and incubated at approximately 30° C. and ambient relative humidity. Newly emerged neonate SCR were collected (approximately 100-200) and total RNA was extracted with a PicoPure™ RNA Isolation Kit (Life Technologies, Carlsbad, Calif.) essentially according to the manufacturer's instructions. RNA concentration was measured by spectrophotometry and purity was assessed by absorbance ratios $A_{260/280}$ and $A_{260/230}$.

SCR total RNA was reverse transcribed to cDNA using an anchored oligo $(dT)_{17}$ primer (Sigma Aldrich, St. Louis, Mo.) and Superscript III reverse transcriptase (Cat. No. 18080-051; Invitrogen, Carlsbad, Calif.) essentially according to the manufacturers' instructions. The reaction was incubated at about 50° C. for 1 h, followed by about 70° C. for 15 min and then diluted with 80 µl ddH₂O and stored at −20° C.

Primers to the wcrIAP1 gene were used to amplify an IAP gene from SCR. The reaction conditions for all amplifications were as follows: 95° C. for 5 min, followed by 35 cycles of 95° C. for 30 s, 50° C. for 30 s, 72° C. for 90 s, and then a final step of 72° C. for 2 min. The entire coding sequence of the SCR IAP gene was amplified with FP02: 5'-ATGGCAGTAGTTCAATCAAATTACATT-3' (SEQ ID NO:59) and RP01: 5'-TGATAGGAACGCTCTGACTGTG-3' (SEQ ID NO:58) and analyzed on a 1% agarose gel. The PCR product was purified using a MinElute PCR Purification Kit (Qiagen, Valencia, Calif.) essentially according to the manufacturer's instructions. The resulting PCR product was 1033 bp long. Using the 3 forward and 3 reverse primers shown in Table 5, the entire amplicon was sequenced using standard Sanger sequencing methods.

Individual sequences were assembled using ContigExpress (Vector NTI, Invitrogen) using default parameters. The resulting full-length scrIAP1 coding sequence is shown in SEQ ID NO:14. The encoded SCR-IAP1 amino acid sequence is shown in SEQ ID NO:22.

*Diabrotica barberi* (Northern Corn Rootworm; NCR)

NCR eggs were obtained from the insect rearing facility at the USDA ARS NCARL (Brookings, S. Dak.) and incubated at about 30° C. and ambient relative humidity. Newly emerged neonates were collected (~20 total) and total RNA was extracted with a PicoPure™ RNA Isolation Kit (Life Technologies, Carlsbad, Calif.) essentially according to the manufacturer's instructions. RNA concentration was measured by spectrophotometry and purity was assessed by $A_{260/280}$ and $A_{260/230}$ ratios.

NCR total RNA was reverse transcribed to cDNA using an anchored oligo $(dT)_{17}$ primer (Sigma-Aldrich, St. Louis, Mo.) and Superscript II reverse transcriptase (Invitrogen, Carlsbad, Calif.) according to the manufacturers' recommendations. The reaction was incubated at about 42° C. for 50 min, followed by 70° C. for 15 min. RNA was removed by treatment with 2 µl RNase H (Invitrogen) and incubate at about 37° C. for 20 min followed by 65° C. for 20 min, and then diluted with 80 µl ddH₂O and stored at −20° C.

Primers to the wcrIAP1 gene described above (Table 1) were used to amplify a NCR IAP gene. The reaction conditions for all amplifications were as follows: 95° C. for 5 min, followed by 35 cycles of 95° C. for 30 s, 50° C. for 30 s, 72° C. for 90 s, and then a final step of 72° C. for 10 min. The entire coding sequence of the NCR IAP gene was amplified with primer FP02 (SEQ ID NO:64) and primer RP01 (SEQ ID NO:63) and analyzed on a 1% agarose gel. The PCR product was purified using a Qiagen (Valencia, Calif.) MinElute kit essentially according to the manufacturer's instructions. The PCR product was 1038 bp long. Using the 3 forward and 3 reverse primers shown in Table 1, the entire amplicon was sequenced using standard Sanger sequencing methods.

Individual sequences are assembled using ContigExpress (Vector NTI, Invitrogen) using default parameters. The assembly was manually edited to produce a final contiguous sequence, designated ncrIAP1 (SEQ ID NO:17) that comprises 1038 bp of the coding sequence. The encoded NCR-IAP1 amino acid sequence is shown in SEQ ID NO:23.

The wcrIAP1, scrIAP1 and ncrIAP1 coding sequences were aligned using Vector NTI Advance™ 11.1.0 (Invitrogen). The scrIAP1 (SEQ ID NO:14) and the ncrIAP1 (SEQ ID NO:17) coding sequences have 95% identity and 97% identity, respectively, with the wcrIAP1 coding sequence (SEQ ID NO:2). The scrIAP1 coding sequence has 94% identity with the ncrIAP1 coding sequence. An alignment of the three coding sequences is shown in FIG. 4 wherein the wcrIAP1 coding sequence (SEQ ID NO:2) was used as the reference sequence.

Figure 5:
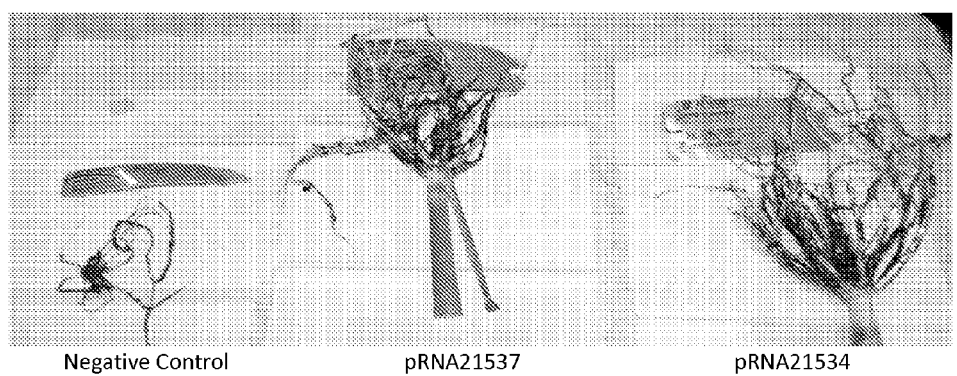
FIG. 5 is a drawing comparing the root mass from transgenic corn plants expressing nucleic acids encoding dsRNA of the invention with control plants.

The WCR-IAP1, SCR-IAP1 and NCR-IAP1 amino acid sequences were aligned using Vector NTI Advance™ 11.1.0 (Invitrogen). The SCR-IAP1 (SEQ ID NO:22) and the NCR-IAP1 (SEQ ID NO:23) amino acid sequences have 95% identity and 97% identity, respectively, with the WCR-IAP1 amino acid sequence (SEQ ID NO:20). The SCR-IAP1 amino acid sequence has 94% identity with the NCR-IAP1 amino acid sequence. An alignment of the three amino sequences is shown in FIG. 5 wherein the WCR-IAP1 amino acid sequence (SEQ ID NO:20) was used as the reference sequence. The WCR-IAP1 and the WCR-IAP2 amino acid sequences have 28% identity.

Example 2

Detection of IAP1 in Different Life Stages

This example describes the detection of wcrIAP1 gene in different life stages of *Diabrotica virgifera* (western corn rootworm).

Total RNA was isolated from larvae and adults of western corn rootworm using standard RNA extraction methods.

Figure 2:
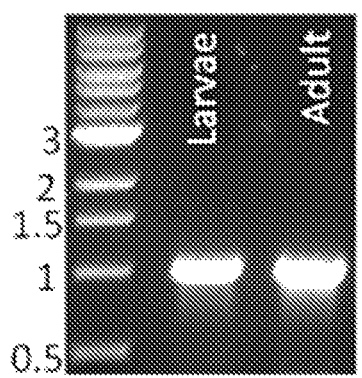
FIG. 2 is an agarose gel of PCR products showing that the identical IAP1 gene is detected in larval stages and adult stage of *Diabrotica virgifera virgifera* (western corn rootworm).
Figure 3:
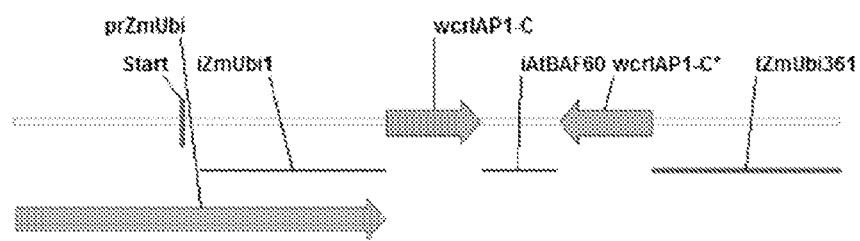
FIG. 3 is a map of an expression vector comprising a nucleic acid molecule that encodes a dsRNA of the invention.

Reverse transcription of mRNA to cDNA was carried out as described above. IAP1-specific PCR primers from those listed in Table 1 above were used in PCR reactions with the larval and adult DNA to detect the presence of IAP1. The results shown in FIG. 2 demonstrate that adult western corn rootworm have the same or substantially the same IAP1 as the larval stages indicating that wcrIAP1 in the adult stage can be targeted with the same or similar dsRNA as that used to target IAP1 in the larval stages. As a consequence, expression of an IAP dsRNA in both above and below ground tissues of a corn plant may affect both larvae and adults and provide increased protection over technologies that target only larval stages.

Example 3

Construction of Interfering RNA Molecules

This example describes the construction of interfering RNA molecules designed to target mRNA transcribable from *Diabrotica* IAP1 genes.

Constructing wcrIAP1 dsRNA

Double stranded RNA (dsRNA) molecules were designed to hybridize to at least three different targets on the wcrIAP1 mRNA (SEQ ID NO:3). wcrIAP1-B (sense strand, SEQ ID NO:5)/wcrIAP-B* (antisense strand, SEQ ID NO:6), wcrIAP1-A (sense strand, SEQ ID NO:7)/wcrIAP1-A* (antisense strand, SEQ ID NO:8) and wcrIAP1-C (sense strand, SEQ ID NO:9)/wcrIAP-C* (antisense strand, SEQ ID NO:10) target base pairs 693-1192, 146-689 and 473-972 of SEQ ID NO:3, respectively. Synthesis of dsRNA was performed using a AmpliScribe™ T7-Flash™ Transcription Kit (Epicentre, Madison, Wis.) essentially according to the manufacturer's instructions. Briefly, 1 μg of template DNA with opposing T7 promoters was used in each 20 μl reaction. Each sample was treated with DNase and precipitated with an equal volume of 5 M ammonium acetate and then washed with 500 μl ice-cold 70% ethanol. The dsRNA was checked for integrity on a 1% agarose gel.

Constructing scrIAP1 dsRNA

Double stranded RNA (dsRNA) molecules were designed to hybridize to the entire southern corn rootworm IAP1 mRNA (SEQ ID NO:15). Synthesis of dsRNA was performed using a AmpliScribe™ T7-Flash™ Transcription Kit (Epicentre, Madison, Wis.) essentially according to the manufacturer's instructions. Briefly, 1 μg of template DNA with opposing T7 promoters was used in each 20 μl reaction. Each sample was treated with DNase and precipitated with an equal volume of 5 M ammonium acetate and then washed with 500 μl ice-cold 70% ethanol. The dsRNA was checked for integrity on a 1% agarose gel. Sequence of the sense strand and antisense strand is shown in SEQ ID NOs: 15 and 16, respectively.

Example 4

Bioassay of Interfering RNA Molecules

This example describes testing dsRNAs of the invention for biological activity against *Diabrotica* insects.

The dsRNA molecules described above were tested for toxicity against several *Diabrotica* species in laboratory bioassays. Bioassays were performed using an RNA-treated artificial diet method. Briefly, molten artificial diet, modified from the diet of Marrone et al. 1985. J. Econ. Entomol. 78:290-293, was poured into each well of 24-well plates and allowed to solidify. dsRNA molecules were diluted to appropriate concentration so that 60 μl of solution was added to the surface of the diet in each well, with a final overlay concentration of 100 ng dsRNA/cm$^2$. One *Diabrotica* larva was added to each well and each 24-well plate was maintained at approximately 28° C. and 16:8 light:dark photoperiod. Mortality was recorded at 7 d post-infestation. dsRNA designed to target green florescent protein (GFP) was used in all bioassays as a negative control. The bioassay was repeated three times.

Double stranded RNAs designed to target different portions of *Diabrotica virgifera* (western corn rootworm) IAP1 mRNA were tested against western corn rootworm larvae. The results, shown in Table 2, demonstrate that a dsRNA molecule designed to target a portion of a mRNA transcribable from a *Diabrotica* insect IAP gene is highly toxic to *Diabrotica virgifera* (western corn rootworm). Both wcrIAP1-A/wcrIAP1-A* (SEQ ID NO:7/SEQ ID NO:8) and wcrIAP1-8/wcrIAP1-8* (SEQ ID NO:5/SEQ ID NO:6) produced a mean of about 90% mortality after 7d.

TABLE 2

Activity of dsRNA against *Diabrotica virgifera* (western corn rootworm).

| | Sample Size | | | % WCR Mortality | | | |
|---|---|---|---|---|---|---|---|
| dsRNA Treatment | Rep 1 | Rep 2 | Rep 3 | Rep 1 | Rep 2 | Rep 3 | Mean |
| wcrIAP1-A/ wcrIAP1-A* | 30 | 48 | 48 | 77 | 96 | 94 | 89 |
| wcrIAP1-B/ wcrIAP1-B* | 30 | 48 | 24 | 87 | 92 | 88 | 89 |
| GFP | 30 | 48 | 24 | 3 | 22 | 20 | 15 |

The wcrIAP1-A/wcrIAP1-A* dsRNA was also tested against *Diabrotica undecimpunctata* (southern corn rootworm) and produced 100% mortality in this species compared to 12% mortality in a GFP control. The results of this bioassay demonstrates that a dsRNA designed to target one *Diabrotica*'s IAP1 mRNA is toxic to a different *Diabrotica* species.

Example 5

Interaction Between Interfering RNA Molecules and Insecticidal Proteins

This example describes the synergistic interaction, with regard to insecticidal activity, between a dsRNA that targets mRNA transcribable from *Diabrotica* IAP genes and insecticidal proteins with activity against *Diabrotica* insects.

The effects of the insecticidal proteins mCry3A or eCry3.1Ab on the sensitive pest species *Diabrotica virgifera* (western corn rootworm; WCR) are investigated in the presence and absence of wcrIAP1-A/wcrIAP1-A*, wcrIAP1-B/wcrIAP1-B*, wcrIAP1-C/wcrIAP1-C*, scrIAP1/scrIAP1* and/or ncrIAP1/ncrIAP1* dsRNA. First instar larvae are used to conduct the WCR diet incorporation bioassay. WCR percent mortality is assessed at approximately 4-7 days after infestation. Approximately two concentrations of mCry3A and eCry3.1Ab giving intermediate level of response are chosen from a dose-response curve to conduct the interaction bioassay. The results indicate a higher WCR percent mortality when wcrIAP1-A/wcrIAP1-A*, wcrIAP1-B/wcrIAP1-B*, wcrIAP1-C/wcrIAP1-C*, scrIAP1/scrIAP1* and/or ncrIAP1/ncrIAP1* dsRNA is present, indicating potential elevated efficacy between dsRNA of the invention and an insecticidal protein when used in combination based upon WCR bioassay. Similar results are observed when mCry3A or eCry3.1Ab is tested in the presence of wcrIAP1-A/wcrIAP1-A*, wcrIAP1-B/wcrIAP1-B*, wcrIAP1-C/wcrIAP1-C*, scrIAP1/scrIAP1* and/or ncrIAP1/ncrIAP1* dsRNA against *Diabrotica barberi* (northern corn rootworm).

Example 6

Activity of dsRNA Expressed in a Plant Cells

This example describes the expression of dsRNA molecules in corn cells.

Vector Construction.

Expression vectors for transforming plant cells generally comprised two expression cassettes, a first expression cassette comprising a Ubi1 promoter operably linked to a nucleotide sequence designed to produce a hairpin RNA (hpRNA) which was operably linked to a Ubi361 terminator; and a second expression cassette comprising a Ubi1 promoter operably linked to a pmi (phosphomannose isomerase) selected marker coding sequence, which was operably linked to a Ubi1 terminator. The nucleotide sequence in the first expression cassette designed to form a hairpin RNA comprised a nucleotide sequence coding for a sense RNA strand fused to an intron spacer, which functions to form a loop sequence, fused to a nucleotide sequence coding for an antisense RNA strand, an example of which is shown in FIG. 3, and having the general formula, sense strand-intron spacer-antisense strand.

Three such expression vectors were constructed to test in plants, 1) pRNA21537—in which the hpRNA encoding nucleotide sequence was designated hpwcrIAP1-C/wcrIAP1-C* SEQ ID NO:63), designed to target a corn rootworm IAP gene; 2) pRNA21534—in which the hpRNA encoding nucleotide sequence was designated hpwcrIAP1-Cα/wcrIAP1-Cα* (SEQ ID NO:64), designed to target a corn rootworm IAP gene; and 3) pRNA21536—in which the hpRNA encoding nucleotide sequence was designated hpNC/NC*, which functioned as a negative control having no known homology to corn rootworm or to corn plant DNA. The vectors also contained selectable markers for selection in bacteria.

To ensure that no unintended proteins were produced in transgenic plants transformed with a vector of the invention, all fortuitous open reading frames in the pRNA21534 vector were disrupted by making single nucleotide point mutations in the hpRNA encoding nucleotide sequence. Eight such point mutations were made. Therefore, the hpRNA encoding sequences in pRNA21537 and pRNA21534 are identical except for the eight point mutations in pRNA21534.

*Agrobacterium* Preparation.

The resulting vectors containing the hairpin RNA encoding expression cassette described above can first be tested in a corn cell culture system such as black Mexican sweet (BMS) corn cells or calli. The vectors are transformed into *Agrobacterium tumefaciens* using standard molecular biology techniques known to those skilled in the art. To prepare the *Agrobacteria* for transformation, cells are suspended in BMS culture media and the density is adjusted to an OD600 of ~0.45. Alternatively, the *Agrobacteria* are cultured in liquid YPC media at 28° C. and 220 rpm overnight. Approximately, four hours prior to BMS transformation, acetosyringone is added to a concentration of 100 μM and the cell density adjusted to an OD600 of ~0.45.

BMS Cell Preparation.

Approximately 3 to 4 d prior to plant cell transformation, the BMS cells are split into new cell culture media by adding 5 ml of BMS cells to 45 ml AW5 media in 125 ml flasks and culture at 25° C., shaking at 125 rpm and no light. Next approximately 1.4 ml of BMS cells culture is pelleted by centrifugation at 2300×g for 5 min at room temperature. The cells are washed once with AW5 media and the cells are pelleted again under the same conditions. The cells are heat shocked for 5 min at 45° C.

BMS Cell Transformation.

Approximately 1 ml of *Agrobacterium* suspension is added to heat shocked BMS cells. The tube is shaken at 80 rpm for 15 min, briefly centrifuged and the *Agrobacterium* media is removed. The BMS cells are spread onto M11/02K media plates with sterile filter paper or nylon netting and cultured at room temperature for 3 d without light. The cells are then transferred to media plates containing the antibiotic timentin and cultured at room temperature for 7 d without light to eliminate *Agrobacterium*. Cells are transferred to media plates containing mannose for selection and cultured at room temperature for 2 to 3 wk without light. The cells are finally transferred to fresh selectable media plates or liquid media and allowed to grow for another 2 wks.

Example 7

Insecticidal Activity of Corn Cells Expressing IAP dsRNA

This example describes testing transformed corn cells expressing IAP dsRNA for bioactivity against *Diabrotica*.

Assays for insect toxicity are performed by feeding transformed black Mexican sweet calli described in Example 6 to western corn rootworm larvae (*Diabrotica virgifera*). Alternatively, an extract containing the interfering RNA is prepared from transformed maize cells and this extract is incorporated into an appropriate insect diet which is fed to *Diabrotica* larvae. Rootworm larvae feeding on transformed calli or extracts of such calli are negatively impacted from the effects of the dsRNA compared to larvae feeding on non-transformed calli or extracts from non-transformed calli.

Example 8

Insecticidal Activity of Transgenic Corn Plants Expressing dsRNA

The vectors described in Example 6 were transformed into maize plants. *Agrobacterium* transformation of immature maize embryos was performed essentially as described in Negrotto et al., 2000, Plant Cell Reports 19: 798-803. For this example, all media constituents were essentially as described in Negrotto et al., supra. However, various media constituents known in the art may be substituted.

Briefly, *Agrobacterium* strain LBA4404 (pSB1) containing a plant transformation plasmid was grown on YEP (yeast extract (5 g/L), peptone (10 g/L), NaCl (5 g/L), 15 g/l agar, pH 6.8) solid medium for 2-4 days at 28° C. Approximately $0.8\times10^9$ *Agrobacterium* were suspended in LS-inf media supplemented with 100 μM As (Negrotto et al., supra). Bacteria were pre-induced in this medium for 30-60 minutes.

Immature embryos from a suitable genotype were excised from 8-12 day old ears into liquid LS-inf+100 μM As. Embryos were rinsed once with fresh infection medium. *Agrobacterium* solution was then added and embryos were vortexed for 30 seconds and allowed to settle with the bacteria for 5 minutes. The embryos were then transferred scutellum side up to LSAs medium and cultured in the dark for two to three days. Subsequently, between 20 and 25 embryos per petri plate were transferred to LSDc medium supplemented with cefotaxime (250 mg/l) and silver nitrate (1.6 mg/l) and cultured in the dark for 28° C. for 10 days.

Immature embryos, producing embryogenic callus were transferred to LSD1M0.55 medium. The cultures were selected on this medium for about 6 weeks with a subculture step at about 3 weeks. Surviving calli was transferred to Reg1 medium supplemented with mannose. Following culturing in the light (16 hour light/8 hour dark regiment), green tissues were then transferred to Reg2 medium without growth regulators and incubated for about 1-2 weeks. Plantlets were transferred to Magenta GA-7 boxes (Magenta Corp, Chicago Ill.) containing Reg3 medium and grown in the light. After about 2-3 weeks, plants were tested for the presence of the pmi gene and hpRNA encoding sequences by qRT-PCR. Positive plants from the PCR assay were transferred to the greenhouse and subsequently tested for resistance to at least *Diabrotica virgifera* (western corn rootworm) using a root excision assay and/or a whole plant assay.

Root Excision Assay

Roots were excised from transgenic plants comprising the constructs described in Example 6. The excised root was placed on moistened sterile germination paper in small snap-cap petri dishes. Ten corn rootworm first-instar larvae were added to each dish. Data were collected at 48, 72 and 96 hours post-infestation. Roots were scored by counting the number of entry wounds caused by CRW and root scaring severity on a scale from 0-10, with 0 being "no scaring" and 10 being "severe scaring." A scaring score of 0 to about 6 indicated that an hpRNA-IAP plant was positive compared to a negative control hpRNA plant.

Whole Plant Assay

Corn plants growing in 3" pots were infested with at least ~30-75 neonate corn rootworm larvae per plant. For each assay, 3 plants were used as uninfested controls, which typically were a heterozygous plant that performed well in the root excision bioassay, a homozygous plant not tested in the root excision bioassay and negative control plant. These plants acted as controls for growth conditions during the course of the assay. Data were collected 10-14 days after infestation. Evaluations were primarily subjective measures comparing infested test plants to those of uninfested and infested control plants. One key visual evaluation that was made was whether the plants showed signs of lodging, a condition indicative of severe damage caused by extensive corn rootworm feeding on the root system.

Bioassay Results

Although bioassay results did not correlate 100% with the levels of hpRNA-encoding nucleic acids in the transgenic plants, results from the root-excision assay indicated that roots from plants transformed with both the pRNA21534 and pRNA21537 vectors were active against *Diabrotica*, corn rootworm. Positive roots from plants transformed with either vector caused CRW mortality and had the lowest number of entry wounds at about 1.3/root compared to negative plants which had as many as to 8.3 wounds/root. In general, many roots from pRNA21534 and pRNA21537 transformed plants had lower scaring severity compared to controls indicating that the dsRNA-treated larvae were negatively impacted by targeting the IAP gene.

Results of the whole plant assay indicated that the level of corn rootworm infestation was high enough to cause severe lodging in many of the negative control plants, whereas only one positive plant transformed with either of the pRNA21534 and pRNA21537 vectors was lodged during the same time period. When plants were removed from the soil at the end of the whole-plant bioassay period to inspect the roots for damage and the root systems compared, the root systems on plants transformed with pRNA21534 and pRNA21537 were generally far more extensive than the control root mass (See FIG. 5 for example), indicating that the expression of a dsRNA targeted at the corn rootworm IAP gene was sufficient to protect the plant from economically significant damage.

Although not all events transformed with the vectors encoding hpRNA targeted at the corn rootworm IAP gene provided good corn rootworm control, the results observed in many of the events clearly showed that expression of nucleic acids encoding such dsRNA that target a corn rootworm IAP gene in transgenic corn is a viable way to control corn rootworm and protect the plant from corn rootworm feeding damage.

It should be understood that the examples and embodiments described herein are for illustrative purposes only and that various modifications or changes in light thereof of the description will be suggested to persons skilled in the art and are to be included within the spirit and purview of this application and the scope of the appended claims.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

What is claimed is:

1. A double stranded RNA (dsRNA) molecule comprising a sense strand and an antisense strand, wherein at least 20 consecutive nucleotides of the antisense strand is complementary to a portion of a mRNA polynucleotide transcribable from a *Diabrotica* insect IAP gene wherein the mRNA polynucleotide comprises at least 20 consecutive nucleotides of SEQ ID NO: 3, and wherein the dsRNA molecule is toxic to a *Diabrotica* insect.

2. The dsRNA molecule of claim 1, wherein the IAP coding sequence comprises SEQ ID NO:2.

3. The dsRNA molecule of claim 1, wherein the portion of the mRNA polynucleotide comprises at least 20 consecutive nucleotides of SEQ ID NO:3.

4. The dsRNA molecule of claim 3, wherein the portion of the mRNA polynucleotide comprises from 20 or 21 consecutive nucleotides to at least 400 consecutive nucleotides of SEQ ID NO:3.

5. The dsRNA of claim 4, wherein the portion of the mRNA polynucleotide consists essentially of any 20-mer subsequence of SEQ ID NO:3 (wcrIAP1) consisting of N to N+19 nucleotides, wherein N is nucleotide 1 to 1602 of SEQ ID NO:3.

6. The dsRNA molecule of claim 4, wherein the portion of the mRNA polynucleotide consists essentially of the nucleotide sequence of SEQ ID NO:3, SEQ ID NO:5, SEQ ID NO:7, or SEQ ID NO:9.

7. The dsRNA molecule of claim 1, wherein the nucleotide sequence of the antisense strand consists essentially of (a) any 20-mer subsequence of SEQ ID NO:4 (wcrIAP1*) consisting of N to N+19 nucleotides, wherein N is nucleotide 1 to 1602 of SEQ ID NO:4.

8. The dsRNA molecule of claim 6, wherein the nucleotide sequence of the antisense strand consists essentially of the nucleotide sequence of SEQ ID NO:4, SEQ ID NO:6, SEQ ID NO:8, or SEQ ID NO:10.

9. The dsRNA molecule of claim 1, wherein the nucleotide sequence of the sense strand is substantially complementary to the nucleotide sequence of the antisense strand.

10. The dsRNA molecule of claim 1, wherein the nucleotide sequence of the sense strand is fully complementary to the nucleotide sequence of the antisense strand.

11. The dsRNA molecule of claim 1, wherein the double stranded RNA molecule is a short hairpin RNA (shRNA) molecule.

12. The dsRNA molecule of claim 1, wherein the *Diabrotica* insect is selected from the group consisting of *D. barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (*chrysanthemum* beetle) and *D. virgifera zeae* (Mexican corn rootworm).

13. A nucleic acid molecule encoding the dsRNA molecule of claim 1.

14. A recombinant vector comprising a regulatory sequence operably linked to a nucleotide sequence that encodes the dsRNA of claim 1.

15. A composition comprising two or more of the dsRNA molecules of claim 1 wherein the two or more RNA molecules each comprise a different antisense strand.

16. The composition of claim 15, comprising an RNA molecule comprising an antisense strand consisting essentially of the nucleotide sequence of SEQ ID NO:6 and an RNA molecule comprising an antisense strand consisting essentially of the nucleotide sequence of SEQ ID NO:8 and/or an RNA molecule comprising an antisense strand consisting essentially of the nucleotide sequence of SEQ ID NO:10.

17. A composition comprising two or more of the nucleic acid molecules of claim 13, wherein the two or more nucleic acid molecules each encode a different antisense strand.

* * * * *